United States Patent [19]
Rambosek et al.

[11] Patent Number: 5,578,478
[45] Date of Patent: Nov. 26, 1996

[54] RECOMBINANT DNA ENCODING A DESULFURIZATION BIOCATALYST

[75] Inventors: John Rambosek; Chris S. Piddington; Brian R. Kovacevich, all of Seattle, Wash.; Kevin D. Young, Grand Forks, N. Dak.; Sylvia A. Denome, Thompson, N. Dak.

[73] Assignee: Energy BioSystems Corporation, The Woodlands, Tex.

[21] Appl. No.: 421,754

[22] Filed: Apr. 14, 1995

Related U.S. Application Data

[62] Division of Ser. No. 304,081, Sep. 1, 1994, which is a division of Ser. No. 89,755, Jul. 9, 1993, Pat. No. 5,356,801, which is a continuation-in-part of Ser. No. 911,845, Jul. 10, 1992, abandoned.

[51] Int. Cl.$^6$ ............... C12N 9/14; C12N 1/20; C12P 21/06; C07H 19/00
[52] U.S. Cl. ............. 435/195; 435/69.1; 435/252.3; 536/22.1; 536/23.1; 536/23.2; 536/23.7
[58] Field of Search ............... 435/195, 252.3, 435/69.1; 536/22.1, 23.1, 23.2, 23.7

[56] References Cited

U.S. PATENT DOCUMENTS

| | | | |
|---|---|---|---|
| 5,002,888 | 3/1991 | Kilbane, II | 435/252.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |

*Primary Examiner*—Robert A. Wax
*Assistant Examiner*—Hyosuk Kim
*Attorney, Agent, or Firm*—Hamilton, Brook, Smith & Reynolds, P.C.

[57] ABSTRACT

This invention relates to a recombinant DNA molecule containing a gene or genes which encode a biocatalyst capable of desulfurizing a fossil fuel which contains organic sulfur molecules. For example, the present invention encompasses a recombinant DNA molecule containing a gene or genes of a strain of *Rhodococcus rhodochrous*.

8 Claims, 12 Drawing Sheets

NdeI CATATGCATTTAAAGGACGCATACGCGATGACTCAACAACGACACAATGCATCTGGCCGG
      GTATACGTAAATTTCCTGCGTATGCGCTACTGAGTTGTTGCTGTTACGTAGACCGGCC NsiI

Beginning of ORF 1

(Synthetic Linkers in bold)

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 5535 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 790..2151

( i x ) FEATURE:
        ( A ) NAME/KEY: CDS
        ( B ) LOCATION: 3256..4506

( x i ) SEQUENCE DESCRIPTION: SEQ ID NO:1:

```
GCATGCACGT  CGCGCCGACG  CATTTGCGCG  CACGGCTCCG  GGCAGTTCTC  GCGGCGCTGG        60

AGGCACGGAT  GGGCACCCTC  AACGAACTCA  CCCAAACCAC  GCCGATAGCG  ATCCTCGCCG       120

AAACCCTCGG  CTACAGCCCT  CAGACATTGG  AAGCTCATGC  GCGACGCATC  CGGATCGACC       180

TTTGCACGCT  ACGTGGCGAC  GCGGCTGGAC  TGACGCTGGA  GGTCCGACCC  GACGTGTGTG       240

GTGTAGCGCC  GCTTAACGGG  TGCGCACGGC  GGGACATCGG  CCAGCTGGCT  TGCCCCTCCT       300

CCGCAGGTAG  TCGACCACCC  CTTCCCGCAG  CGGTCGGAGG  TGATCGACCG  TTAGGGTCAT       360

TTGCTCGCAG  ATCGGCTGAT  GTTGCCGATC  GACGTGGTCG  ACGGGACACG  CTCGCGATTG       420

GCATGGCGTC  CGGTGCATAC  ACGACGATCT  AACCAGATCG  ACGGTTTTGA  GCGTCGGTCA       480

ACGTCGACTC  GATGCGCCGT  GCGAGTGAGA  TCCTTTGTGG  TGCTTGGCTA  TTGACCTCGA       540

CAAGGATAGA  GATTCGAAGG  ACCTCGGATC  GACCCAAATG  CGGACGGCCG  GCAGCGGCGA       600

AGGCGGCCAA  GTCATCGGCA  CCGTCACCGT  CACCTTGACC  CGACGTGCCC  CGTGGTTCAA       660

GGCCTGAATT  TGGCTGGTGG  AGCATTGAAA  TCAGGTGAAG  TTTAACGGTG  GGCACACCCC       720

GGGGGTGGGG  GTGAGACTGC  TTAGCGACAG  GAATCTAGCC  ATGATTGACA  TTTAAAGGAC       780

GCATACGCG  ATG  ACT  CAA  CAA  CGA  CAA  ATG  CAT  CTG  GCC  GGT  TTC  TTC    828
           Met  Thr  Gln  Gln  Arg  Gln  Met  His  Leu  Ala  Gly  Phe  Phe
            1                 5                          10

TCG  GCC  GGC  AAT  GTG  ACT  CAT  GCA  CAT  GGG  GCG  TGG  CGG  CAC  ACG  GAC    876
Ser  Ala  Gly  Asn  Val  Thr  His  Ala  His  Gly  Ala  Trp  Arg  His  Thr  Asp
      15                 20                          25

GCG  TCG  AAT  GAC  TTT  CTG  TCG  GGG  AAG  TAC  TAC  CAA  CAC  ATC  GCC  CGT    924
Ala  Ser  Asn  Asp  Phe  Leu  Ser  Gly  Lys  Tyr  Tyr  Gln  His  Ile  Ala  Arg
 30                      35                      40                      45

ACT  CTG  GAG  CGC  GGC  AAG  TTC  GAT  CTG  TTG  TTT  CTG  CCT  GAC  GGG  TTG    972
```

```
Thr Leu Glu Arg Gly Lys Phe Asp Leu Leu Phe Leu Pro Asp Gly Leu
            50                  55                  60

GCC GTC GAG GAC AGC TAC GGG GAC AAC CTG GAC ACC GGT GTC GGC CTG    1020
Ala Val Glu Asp Ser Tyr Gly Asp Asn Leu Asp Thr Gly Val Gly Leu
            65                  70                  75

GGC GGG CAG GGT GCA GTC GCC TTG GAG CCG GCC AGT GTG GTC GCA ACC    1068
Gly Gly Gln Gly Ala Val Ala Leu Glu Pro Ala Ser Val Val Ala Thr
            80                  85                  90

ATG GCC GCG GTG ACC GAG CAC CTG GGT CTT GGG GCA ACC ATT TCG GCG    1116
Met Ala Ala Val Thr Glu His Leu Gly Leu Gly Ala Thr Ile Ser Ala
    95                  100                 105

ACC TAC TAT CCC CCG TAT CAC GTT GCT CGG GTG TTC GCG ACG CTC GAT    1164
Thr Tyr Tyr Pro Pro Tyr His Val Ala Arg Val Phe Ala Thr Leu Asp
110                 115                 120                 125

CAG TTG TCA GGG GGT CGG GTG TCC TGG AAC GTC GTC ACC TCG CTC AAC    1212
Gln Leu Ser Gly Gly Arg Val Ser Trp Asn Val Val Thr Ser Leu Asn
            130                 135                 140

GAC GCT GAA GCG CGC AAC TTC GGC ATT AAT CAG CAT CTG GAA CAC GAC    1260
Asp Ala Glu Ala Arg Asn Phe Gly Ile Asn Gln His Leu Glu His Asp
            145                 150                 155

GCC CGC TAT GAC CGC GCC GAT GAG TTC TTG GAA GCG GTC AAG AAA CTC    1308
Ala Arg Tyr Asp Arg Ala Asp Glu Phe Leu Glu Ala Val Lys Lys Leu
            160                 165                 170

TGG AAC AGC TGG GAC GAG GAC GCC CTC GTG CTG GAC AAG GCG GCC GGC    1356
Trp Asn Ser Trp Asp Glu Asp Ala Leu Val Leu Asp Lys Ala Ala Gly
    175                 180                 185

GTG TTC GCC GAT CCC GCG AAG GTG CAC TAC GTC GAT CAC CAC GGG GAG    1404
Val Phe Ala Asp Pro Ala Lys Val His Tyr Val Asp His His Gly Glu
190                 195                 200                 205

TGG CTG AAT GTG CGC GGA CCT CTG CAG GTA CCG CGT TCA CCT CAG GGT    1452
Trp Leu Asn Val Arg Gly Pro Leu Gln Val Pro Arg Ser Pro Gln Gly
            210                 215                 220

GAG CCG GTG ATC CTG CAG GCC GGC CTG TCG CCC CGG GGT CGG CGC TTC    1500
Glu Pro Val Ile Leu Gln Ala Gly Leu Ser Pro Arg Gly Arg Arg Phe
            225                 230                 235

GCC GGG AAG TGG GCC GAG GCC GTC TTC AGT CTT GCA CCC AAC CTC GAG    1548
Ala Gly Lys Trp Ala Glu Ala Val Phe Ser Leu Ala Pro Asn Leu Glu
            240                 245                 250

GTG ATG CAG GCC ACC TAC CAG GGC ATC AAA GCC GAG GTC GAC GCT GCG    1596
Val Met Gln Ala Thr Tyr Gln Gly Ile Lys Ala Glu Val Asp Ala Ala
    255                 260                 265

GGG CGC GAT CCC GAT CAG ACG AAA ATC TTC ACC GCC GTG ATG CCG GTA    1644
Gly Arg Asp Pro Asp Gln Thr Lys Ile Phe Thr Ala Val Met Pro Val
270                 275                 280                 285

CTC GGC GAA AGC CAG GCG GTG GCA CAG GAA CGA CTG GAA TAT CTC AAC    1692
Leu Gly Glu Ser Gln Ala Val Ala Gln Glu Arg Leu Glu Tyr Leu Asn
            290                 295                 300

AGT CTG GTC CAT CCG GAA GTG GGA CTG TCG ACG CTA TCC AGT CAC ACC    1740
Ser Leu Val His Pro Glu Val Gly Leu Ser Thr Leu Ser Ser His Thr
            305                 310                 315

GGC ATC AAC CTG GCG GCG TAC CCT CTC GAC ACT CCG ATC AAG GAC ATC    1788
Gly Ile Asn Leu Ala Ala Tyr Pro Leu Asp Thr Pro Ile Lys Asp Ile
            320                 325                 330

CTG CGG GAT CTG CAG GAT CGG AAT GTC CCG ACG CAA CTG CAC ATG TTC    1836
Leu Arg Asp Leu Gln Asp Arg Asn Val Pro Thr Gln Leu His Met Phe
    335                 340                 345

GCC GCC GCA ACG CAC AGC GAA GAG CTC ACG CTG GCG GAA ATG GGT CGG    1884
Ala Ala Ala Thr His Ser Glu Glu Leu Thr Leu Ala Glu Met Gly Arg
350                 355                 360                 365

CGC TAT GGA ACC AAC GTG GGG TTC GTT CCT CAG TGG GCC GGT ACC GGG    1932
```

|     |     |     |     |     |     |     |     |     |     |     |     |     |     |     |      |
|-----|-----|-----|-----|-----|-----|-----|-----|-----|-----|-----|-----|-----|-----|-----|------|
| Arg | Tyr | Gly | Thr | Asn | Val | Gly | Phe | Val | Pro | Gln | Trp | Ala | Gly | Thr | Gly  |
|     |     |     |     | 370 |     |     |     |     | 375 |     |     |     |     | 380 |      |
| GAG | CAG | ATC | GCT | GAC | GAG | CTG | ATC | CGC | CAC | TTC | GAG | GGC | GGC | GCC | GCG  | 1980 |
| Glu | Gln | Ile | Ala | Asp | Glu | Leu | Ile | Arg | His | Phe | Glu | Gly | Gly | Ala | Ala  |
|     |     |     |     | 385 |     |     |     |     | 390 |     |     |     |     | 395 |      |
| GAT | GGT | TTC | ATC | ATC | TCT | CCG | GCC | TTC | CTG | CCG | GGC | TCC | TAC | GAC | GAG  | 2028 |
| Asp | Gly | Phe | Ile | Ile | Ser | Pro | Ala | Phe | Leu | Pro | Gly | Ser | Tyr | Asp | Glu  |
|     |     |     |     | 400 |     |     |     |     | 405 |     |     |     |     | 410 |      |
| TTC | GTC | GAC | CAG | GTG | GTT | CCG | GTT | CTG | CAG | GAT | CGC | GGC | TAC | TTC | CGC  | 2076 |
| Phe | Val | Asp | Gln | Val | Val | Pro | Val | Leu | Gln | Asp | Arg | Gly | Tyr | Phe | Arg  |
|     |     |     | 415 |     |     |     |     | 420 |     |     |     | 425 |     |     |      |
| ACC | GAG | TAC | CAG | GGC | AAC | ACT | CTG | CGC | GAC | CAC | TTG | GGT | CTG | CGC | GTA  | 2124 |
| Thr | Glu | Tyr | Gln | Gly | Asn | Thr | Leu | Arg | Asp | His | Leu | Gly | Leu | Arg | Val  |
| 430 |     |     |     |     | 435 |     |     |     |     | 440 |     |     |     |     | 445  |
| CCA | CAA | CTG | CAA | GGA | CAA | CCT | TCA | TGACAAGCCG | CGTCGACCCC | GCAAACCCG |  | | | | | 2178 |
| Pro | Gln | Leu | Gln | Gly | Gln | Pro | Ser |     |     |     |     |     |     |     |      |
|     |     |     |     | 450 |     |     |     |     |     |     |     |     |     |     |      |

```
GTTCAGAACT CGATTCCGCC ATCCGCGACA CACTGACCTA CAGCAACTGC CCGGTACCCA   2238
ACGCTCTGCT CACGGCATCG GAATCGGGCT TCCTCGACGC CGCCGGCATC GAACTCGACG   2298
TCCTCAGCGG CCAGCAGGGC ACGGTTCATT TCACCTACGA CCAGCCTGCC TACACCCGTT   2358
TTGGGGGTGA GATCCCGCCA CTGCTCAGCG AGGGGTTGCG GGCACCTGGG CGCACGCGTC   2418
TACTCGGCAT CACCCCGCTC TTGGGGCGCC AGGGCTTCTT TGTCCGCGAC GACAGCCCGA   2478
TCACAGCGGC CGCCGACCTT GCCGGACGTC GAATCGGCGT CTCGGCCTCG GCAATTCGCA   2538
TCCTGCGCGG CCAGCTGGGC GACTACCTCG AGTTGGATCC CTGGCGGCAA ACGCTGGTAG   2598
CGCTGGGCTC GTGGGAGGCG CGCGCCTTGT TGCACACCCT TGAGCACGGT GAACTGGGTG   2658
TGGACGACGT CGAGCTGGTG CCGATCAGCA GTCCTGGTGT CGATGTTCCC GCTGAGCAGC   2718
TCGAAGAATC GGCGACCGTC AAGGGTGCGG ACCTCTTTCC CGATGTCGCC CGCGGTCAGG   2778
CCGCGGTGTT GGCCAGCGGA GACGTTGACG CCCTGTACAG TTGGCTGCCC TGGGCCGGGG   2838
AGTTGCAAGC CACCGGGGCC CGCCCAGTGG TGGATCTCGG CCTCGATGAG CGCAATGCCT   2898
ACGCCAGTGT GTGGACGGTC AGCAGCGGGC TGGTTCGCCA GCGACCTGGC CTTGTTCAAC   2958
GACTGGTCGA CGCGGCCGTC GACGCCGGGC TGTGGGCACG CGATCATTCC GACGCGGTGA   3018
CCAGCCTGCA CGCCGCGAAC CTGGGCGTAT CGACCGGAGC AGTAGGCCAG GGCTTCGGCG   3078
CCGACTTCCA GCAGCGTCTG GTTCCACGCC TGGATACGA CGCCCTCGCC CTCCTGGAGC   3138
GCACACAGCA ATTCCTGCTC ACCAACAACT TGCTGCAGGA ACCCGTCGCC CTCGATCAGT   3198
GGGCGGCTCC GGAATTTCTG AACAACAGCC TCAATCGCCA CCGATAGGAA CATCCGC      3255
```

|     |     |     |     |     |     |     |     |     |     |     |     |     |     |     |      |
|-----|-----|-----|-----|-----|-----|-----|-----|-----|-----|-----|-----|-----|-----|-----|------|
| ATG | ACA | CTG | TCA | CCT | GAA | AAG | CAG | CAC | GTT | CGA | CCA | CGC | GAC | GCC | GCC  | 3303 |
| Met | Thr | Leu | Ser | Pro | Glu | Lys | Gln | His | Val | Arg | Pro | Arg | Asp | Ala | Ala  |
| 1   |     |     |     | 5   |     |     |     |     | 10  |     |     |     |     | 15  |      |
| GAC | AAC | GAT | CCC | GTC | GCG | GTT | GCC | CGT | GGG | CTA | GCC | GAA | AAG | TGG | CGA  | 3351 |
| Asp | Asn | Asp | Pro | Val | Ala | Val | Ala | Arg | Gly | Leu | Ala | Glu | Lys | Trp | Arg  |
|     |     |     | 20  |     |     |     |     | 25  |     |     |     |     | 30  |     |      |
| GCC | ACC | GCC | GTC | GAG | CGT | GAT | CGC | GCC | GGG | GGT | TCG | GCA | ACA | GCC | GAG  | 3399 |
| Ala | Thr | Ala | Val | Glu | Arg | Asp | Arg | Ala | Gly | Gly | Ser | Ala | Thr | Ala | Glu  |
|     |     | 35  |     |     |     |     | 40  |     |     |     |     | 45  |     |     |      |
| CGC | GAA | GAC | CTG | CGC | GCG | AGC | GCG | CTG | CTG | TCG | CTC | CTC | GTC | CCG | CGC  | 3447 |
| Arg | Glu | Asp | Leu | Arg | Ala | Ser | Ala | Leu | Leu | Ser | Leu | Leu | Val | Pro | Arg  |
|     | 50  |     |     |     | 55  |     |     |     |     | 60  |     |     |     |     |      |
| GAA | TAC | GGC | GGC | TGG | GGC | GCA | GAC | TGG | CCC | ACC | GCC | ATC | GAG | GTC | GTC  | 3495 |
| Glu | Tyr | Gly | Gly | Trp | Gly | Ala | Asp | Trp | Pro | Thr | Ala | Ile | Glu | Val | Val  |
| 65  |     |     |     | 70  |     |     |     |     | 75  |     |     |     |     | 80  |      |
| CGC | GAA | ATC | GCG | GCA | GCC | GAT | GGA | TCT | TTG | GGA | CAC | CTG | TTC | GGA | TAC  | 3543 |

|  |  |  |  |  |  |  |  |  |  |  |  |  |  |  |  |
|---|---|---|---|---|---|---|---|---|---|---|---|---|---|---|---|
| Arg | Glu | Ile | Ala | Ala 85 | Ala | Asp | Gly | Ser | Leu 90 | Gly | His | Leu | Phe | Gly 95 | Tyr |

| CAC | CTC | ACC | AAC | GCC | CCG | ATG | ATC | GAA | CTG | ATC | GGC | TCG | CAG | GAA | CAA | 3591 |
|---|---|---|---|---|---|---|---|---|---|---|---|---|---|---|---|---|
| His | Leu | Thr | Asn | Ala | Pro | Met | Ile | Glu | Leu | Ile | Gly | Ser | Gln | Glu | Gln |  |
|  |  |  | 100 |  |  |  | 105 |  |  |  |  |  | 110 |  |  |  |

| GAA | GAA | CAC | CTG | TAC | ACC | CAG | ATC | GCG | CAG | AAC | AAC | TGG | TGG | ACC | GGA | 3639 |
|---|---|---|---|---|---|---|---|---|---|---|---|---|---|---|---|---|
| Glu | Glu | His | Leu | Tyr | Thr | Gln | Ile | Ala | Gln | Asn | Asn | Trp | Trp | Thr | Gly |  |
|  |  | 115 |  |  |  |  | 120 |  |  |  |  | 125 |  |  |  |  |

| AAT | GCC | TCC | AGC | GAG | AAC | AAC | AGC | CAC | GTG | CTG | GAC | TGG | AAG | GTC | AGC | 3687 |
|---|---|---|---|---|---|---|---|---|---|---|---|---|---|---|---|---|
| Asn | Ala | Ser | Ser | Glu | Asn | Asn | Ser | His | Val | Leu | Asp | Trp | Lys | Val | Ser |  |
|  | 130 |  |  |  |  | 135 |  |  |  |  | 140 |  |  |  |  |  |

| GCC | ACC | CCG | ACC | GAA | GAC | GGC | GGC | TAC | GTG | CTC | AAT | GGC | ACG | AAG | CAC | 3735 |
|---|---|---|---|---|---|---|---|---|---|---|---|---|---|---|---|---|
| Ala | Thr | Pro | Thr | Glu | Asp | Gly | Gly | Tyr | Val | Leu | Asn | Gly | Thr | Lys | His |  |
| 145 |  |  |  |  | 150 |  |  |  |  | 155 |  |  |  |  | 160 |  |

| TTC | TGC | AGC | GGC | GCC | AAG | GGG | TCG | GAC | CTG | CTG | TTC | GTG | TTC | GGC | GTC | 3783 |
|---|---|---|---|---|---|---|---|---|---|---|---|---|---|---|---|---|
| Phe | Cys | Ser | Gly | Ala | Lys | Gly | Ser | Asp | Leu | Leu | Phe | Val | Phe | Gly | Val |  |
|  |  |  |  | 165 |  |  |  |  | 170 |  |  |  |  | 175 |  |  |

| GTC | CAG | GAT | GAT | TCT | CCG | CAG | CAG | GGT | GCG | ATC | ATT | GCT | GCC | GCT | ATC | 3831 |
|---|---|---|---|---|---|---|---|---|---|---|---|---|---|---|---|---|
| Val | Gln | Asp | Asp | Ser | Pro | Gln | Gln | Gly | Ala | Ile | Ile | Ala | Ala | Ala | Ile |  |
|  |  |  | 180 |  |  |  |  | 185 |  |  |  |  | 190 |  |  |  |

| CCG | ACA | TCG | CGG | GCT | GGC | GTT | ACG | CCC | AAC | GAC | GAC | TGG | GCC | GCC | ATC | 3879 |
|---|---|---|---|---|---|---|---|---|---|---|---|---|---|---|---|---|
| Pro | Thr | Ser | Arg | Ala | Gly | Val | Thr | Pro | Asn | Asp | Asp | Trp | Ala | Ala | Ile |  |
|  |  | 195 |  |  |  |  | 200 |  |  |  |  | 205 |  |  |  |  |

| GGC | ATG | CGG | CAG | ACC | GAC | AGC | GGT | TCC | ACG | GAC | TTC | CAC | AAC | GTC | AAG | 3927 |
|---|---|---|---|---|---|---|---|---|---|---|---|---|---|---|---|---|
| Gly | Met | Arg | Gln | Thr | Asp | Ser | Gly | Ser | Thr | Asp | Phe | His | Asn | Val | Lys |  |
|  | 210 |  |  |  |  | 215 |  |  |  |  | 220 |  |  |  |  |  |

| GTC | GAG | CCT | GAC | GAA | GTG | CTG | GGC | GCG | CCC | AAC | GCC | TTC | GTT | CTC | GCC | 3975 |
|---|---|---|---|---|---|---|---|---|---|---|---|---|---|---|---|---|
| Val | Glu | Pro | Asp | Glu | Val | Leu | Gly | Ala | Pro | Asn | Ala | Phe | Val | Leu | Ala |  |
| 225 |  |  |  |  | 230 |  |  |  |  | 235 |  |  |  |  | 240 |  |

| TTC | ATA | CAA | TCC | GAG | CGC | GGC | AGC | CTC | TTC | GCG | CCC | ATA | GCG | CAA | TTG | 4023 |
|---|---|---|---|---|---|---|---|---|---|---|---|---|---|---|---|---|
| Phe | Ile | Gln | Ser | Glu | Arg | Gly | Ser | Leu | Phe | Ala | Pro | Ile | Ala | Gln | Leu |  |
|  |  |  |  | 245 |  |  |  |  | 250 |  |  |  |  | 255 |  |  |

| ATC | TTC | GCC | AAC | GTC | TAT | CTG | GGG | ATC | GCG | CAC | GGC | GCA | CTC | GAT | GCC | 4071 |
|---|---|---|---|---|---|---|---|---|---|---|---|---|---|---|---|---|
| Ile | Phe | Ala | Asn | Val | Tyr | Leu | Gly | Ile | Ala | His | Gly | Ala | Leu | Asp | Ala |  |
|  |  |  | 260 |  |  |  |  | 265 |  |  |  |  | 270 |  |  |  |

| GCC | AGG | GAG | TAC | ACC | CGT | ACC | CAG | GCG | AGG | CCC | TGG | ACA | CCG | GCC | GGT | 4119 |
|---|---|---|---|---|---|---|---|---|---|---|---|---|---|---|---|---|
| Ala | Arg | Glu | Tyr | Thr | Arg | Thr | Gln | Ala | Arg | Pro | Trp | Thr | Pro | Ala | Gly |  |
|  |  | 275 |  |  |  |  | 280 |  |  |  |  | 285 |  |  |  |  |

| ATT | CAA | CAG | GCA | ACC | GAG | GAT | CCC | TAC | ACC | ATC | CGC | TCC | TAC | GGT | GAG | 4167 |
|---|---|---|---|---|---|---|---|---|---|---|---|---|---|---|---|---|
| Ile | Gln | Gln | Ala | Thr | Glu | Asp | Pro | Tyr | Thr | Ile | Arg | Ser | Tyr | Gly | Glu |  |
|  | 290 |  |  |  |  | 295 |  |  |  |  | 300 |  |  |  |  |  |

| TTC | ACC | ATC | GCA | TTG | CAG | GGA | GCT | GAC | GCC | GCC | GCC | CGT | GAA | GCG | GCC | 4215 |
|---|---|---|---|---|---|---|---|---|---|---|---|---|---|---|---|---|
| Phe | Thr | Ile | Ala | Leu | Gln | Gly | Ala | Asp | Ala | Ala | Ala | Arg | Glu | Ala | Ala |  |
| 305 |  |  |  |  | 310 |  |  |  |  | 315 |  |  |  |  | 320 |  |

| CAC | CTG | CTG | CAG | ACG | GTG | TGG | GAC | AAG | GGC | GAC | GCG | CTC | ACC | CCC | GAG | 4263 |
|---|---|---|---|---|---|---|---|---|---|---|---|---|---|---|---|---|
| His | Leu | Leu | Gln | Thr | Val | Trp | Asp | Lys | Gly | Asp | Ala | Leu | Thr | Pro | Glu |  |
|  |  |  |  | 325 |  |  |  |  | 330 |  |  |  |  | 335 |  |  |

| GAC | CGC | GGC | GAA | CTG | ATG | GTG | AAG | GTC | TCG | GGA | GTC | AAA | GCG | TTG | GCC | 4311 |
|---|---|---|---|---|---|---|---|---|---|---|---|---|---|---|---|---|
| Asp | Arg | Gly | Glu | Leu | Met | Val | Lys | Val | Ser | Gly | Val | Lys | Ala | Leu | Ala |  |
|  |  |  |  | 340 |  |  |  |  | 345 |  |  |  |  | 350 |  |  |

| ACC | AAC | GCC | GCC | CTC | AAC | ATC | AGC | AGC | GGC | GTC | TTC | GAG | GTG | ATC | GGC | 4359 |
|---|---|---|---|---|---|---|---|---|---|---|---|---|---|---|---|---|
| Thr | Asn | Ala | Ala | Leu | Asn | Ile | Ser | Ser | Gly | Val | Phe | Glu | Val | Ile | Gly |  |
|  |  | 355 |  |  |  |  | 360 |  |  |  |  | 365 |  |  |  |  |

| GCG | CGC | GGA | ACA | CAT | CCC | AGG | TAC | GGT | TTC | GAC | CGC | TTC | TGG | CGC | AAC | 4407 |
|---|---|---|---|---|---|---|---|---|---|---|---|---|---|---|---|---|
| Ala | Arg | Gly | Thr | His | Pro | Arg | Tyr | Gly | Phe | Asp | Arg | Phe | Trp | Arg | Asn |  |
|  | 370 |  |  |  |  | 375 |  |  |  |  | 380 |  |  |  |  |  |

| GTG | CGC | ACC | CAC | TCC | CTG | CAC | GAC | CCG | GTG | TCC | TAC | AAG | ATC | GCC | GAC | 4455 |
|---|---|---|---|---|---|---|---|---|---|---|---|---|---|---|---|---|
| Val | Arg | Thr | His | Ser | Leu | His | Asp | Pro | Val | Ser | Tyr | Lys | Ile | Ala | Asp |  |
| 385 |  |  |  |  | 390 |  |  |  |  | 395 |  |  |  |  | 400 |  |

| GTC | GGC | AAG | CAC | ACC | TTG | AAC | GGT | CAA | TAC | CCG | ATT | CCC | GGC | TTC | ACC | 4503 |
|---|---|---|---|---|---|---|---|---|---|---|---|---|---|---|---|---|

| Val | Gly | Lys | His | Thr | Leu | Asn | Gly | Gln | Tyr | Pro | Ile | Pro | Gly | Phe | Thr |
|---|---|---|---|---|---|---|---|---|---|---|---|---|---|---|---|
| | | | | 405 | | | | | 410 | | | | | 415 | |

```
TCC TGAGGATCTG AGGCGCTGAT CGAGGCCGAG GCCACCGCGC GGCCGAGTCG         4556
Ser
CGAATCGCCC GCCGATACTC AGCTTCTCCA TACGTACGGG TGCACACAAG GAGATATTGT   4616
CAAGACCTGT GGATGAGGGT GTTTCAGGCG ACCTCCGTTT CGCTTGATTC GTCGGGCTCA   4676
GCGGGTGAGA TGTCGATGGG TCGTTCGAGC AGCTTGCCTT TGTGGAACAC CGCGCCGGCA   4736
CGGACCAGCG CGACCAGATG GGGGGCGTTG ACCGCCGCCA GCGGGCTTGT GCGGCGTCGA   4796
TCAGCTTGTA GGCCATGGCA ATCCCGCTGC GACGTGACCC AGGGCCCTTG GTGACCTTGG   4856
TTCGCAACCG CACGGTCGCA AACGTCGATT CGATCGGATT CGTAGTGCGC AAGTGGATCC   4916
AGTGCTCGGC CGGGTACCGG TAGAACTCCA GGAGCACGTC GGCGTCGTCG ACGATCTTGG   4976
CGACCGCCTT GGGGTACTTC GCGCCGTAAT CTACCTCGAA GGCCTTGATC GCGACCTGGG   5036
CCTTGTCGAT GTCCTCGGCG TTGTAGATTT CCCGCATCGC CGCGGTCGCA CCTGGATGAG   5096
CCGACTTGGG CAGCGCAGCA AGCACATTGG CCTGCTTGTG AAACCAGCAG CGCTGTTCAC   5156
GGGTATCCGG AAACACCTCC CGCAGTGCCT TCCAGAACCC CAGCGCCCCA TCACCGACGG   5216
CCAGCACCGG GGCGGTCATC CCGCGGCGTC GGCATGAGCG CAGCAGATCA GCCCACGACT   5276
CTGTGGACTC CCGGAACCCA TCGGTGAGCG CGACGAGCTC CTTGCGGCCG TCGGCGCGGA   5336
CGCCGATCAT CACGAGCAAG CACACGCTTCT CCTGCTCCAG GCGGACATTG AGATGGATGC   5396
CGTCGACCCA TAGGTACACG AAATCGGTGC CCGAGAGATC CCGGTCGGCG AAGGCCTTCG   5456
CCTCGTCCTG CCATTGCGCG GTCAGCCGGG TGATCGTCGA GGCCGACAGC CCGGCACCAG   5516
TGCCGAGGAA CTGCTCCAA                                                5535
```

(2) INFORMATION FOR SEQ ID NO:2:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:2:

| Met | Thr | Gln | Gln | Arg | Gln | Met | His | Leu | Ala | Gly | Phe | Phe | Ser | Ala | Gly |
|---|---|---|---|---|---|---|---|---|---|---|---|---|---|---|---|
| 1 | | | | 5 | | | | | 10 | | | | | 15 | |

| Asn | Val | Thr | His | Ala | His | Gly | Ala | Trp | Arg | His | Thr | Asp | Ala | Ser | Asn |
|---|---|---|---|---|---|---|---|---|---|---|---|---|---|---|---|
| | | | | 20 | | | | | 25 | | | | | 30 | |

| Asp | Phe | Leu | Ser | Gly | Lys | Tyr | Tyr | Gln | His | Ile | Ala | Arg | Thr | Leu | Glu |
|---|---|---|---|---|---|---|---|---|---|---|---|---|---|---|---|
| | | | 35 | | | | | 40 | | | | | 45 | | |

| Arg | Gly | Lys | Phe | Asp | Leu | Leu | Phe | Leu | Pro | Asp | Gly | Leu | Ala | Val | Glu |
|---|---|---|---|---|---|---|---|---|---|---|---|---|---|---|---|
| | 50 | | | | | 55 | | | | | 60 | | | | |

| Asp | Ser | Tyr | Gly | Asp | Asn | Leu | Asp | Thr | Gly | Val | Gly | Leu | Gly | Gly | Gln |
|---|---|---|---|---|---|---|---|---|---|---|---|---|---|---|---|
| 65 | | | | | 70 | | | | | 75 | | | | | 80 |

| Gly | Ala | Val | Ala | Leu | Glu | Pro | Ala | Ser | Val | Val | Ala | Thr | Met | Ala | Ala |
|---|---|---|---|---|---|---|---|---|---|---|---|---|---|---|---|
| | | | | 85 | | | | | 90 | | | | | 95 | |

| Val | Thr | Glu | His | Leu | Gly | Leu | Gly | Ala | Thr | Ile | Ser | Ala | Thr | Tyr | Tyr |
|---|---|---|---|---|---|---|---|---|---|---|---|---|---|---|---|
| | | | | 100 | | | | | 105 | | | | | 110 | |

| Pro | Pro | Tyr | His | Val | Ala | Arg | Val | Phe | Ala | Thr | Leu | Asp | Gln | Leu | Ser |
|---|---|---|---|---|---|---|---|---|---|---|---|---|---|---|---|
| | | | 115 | | | | | 120 | | | | | 125 | | |

| Gly | Gly | Arg | Val | Ser | Trp | Asn | Val | Val | Thr | Ser | Leu | Asn | Asp | Ala | Glu |
|---|---|---|---|---|---|---|---|---|---|---|---|---|---|---|---|
| | 130 | | | | | 135 | | | | | 140 | | | | |

| Ala | Arg | Asn | Phe | Gly | Ile | Asn | Gln | His | Leu | Glu | His | Asp | Ala | Arg | Tyr |
|---|---|---|---|---|---|---|---|---|---|---|---|---|---|---|---|

| 145 | | | | | 150 | | | | | 155 | | | | | 160 |
|---|---|---|---|---|---|---|---|---|---|---|---|---|---|---|---|

Asp Arg Ala Asp Glu Phe Leu Glu Ala Val Lys Lys Leu Trp Asn Ser
                    165                   170                 175

Trp Asp Glu Asp Ala Leu Val Leu Asp Lys Ala Ala Gly Val Phe Ala
           180                   185               190

Asp Pro Ala Lys Val His Tyr Val Asp His His Gly Glu Trp Leu Asn
          195                 200               205

Val Arg Gly Pro Leu Gln Val Pro Arg Ser Pro Gln Gly Glu Pro Val
    210                 215               220

Ile Leu Gln Ala Gly Leu Ser Pro Arg Gly Arg Arg Phe Ala Gly Lys
225                 230               235            240

Trp Ala Glu Ala Val Phe Ser Leu Ala Pro Asn Leu Glu Val Met Gln
               245             250            255

Ala Thr Tyr Gln Gly Ile Lys Ala Glu Val Asp Ala Ala Gly Arg Asp
          260                 265               270

Pro Asp Gln Thr Lys Ile Phe Thr Ala Val Met Pro Val Leu Gly Glu
         275                 280              285

Ser Gln Ala Val Ala Gln Glu Arg Leu Glu Tyr Leu Asn Ser Leu Val
    290                 295               300

His Pro Glu Val Gly Leu Ser Thr Leu Ser Ser His Thr Gly Ile Asn
305                 310               315            320

Leu Ala Ala Tyr Pro Leu Asp Thr Pro Ile Lys Asp Ile Leu Arg Asp
               325             330            335

Leu Gln Asp Arg Asn Val Pro Thr Gln Leu His Met Phe Ala Ala Ala
          340                 345              350

Thr His Ser Glu Glu Leu Thr Leu Ala Glu Met Gly Arg Arg Tyr Gly
        355                 360             365

Thr Asn Val Gly Phe Val Pro Gln Trp Ala Gly Thr Gly Glu Gln Ile
       370                 375             380

Ala Asp Glu Leu Ile Arg His Phe Glu Gly Gly Ala Ala Asp Gly Phe
385                 390               395            400

Ile Ile Ser Pro Ala Phe Leu Pro Gly Ser Tyr Asp Glu Phe Val Asp
             405             410            415

Gln Val Val Pro Val Leu Gln Asp Arg Gly Tyr Phe Arg Thr Glu Tyr
         420                425             430

Gln Gly Asn Thr Leu Arg Asp His Leu Gly Leu Arg Val Pro Gln Leu
       435              440              445

Gln Gly Gln Pro Ser
450

( 2 ) INFORMATION FOR SEQ ID NO:3:

( i ) SEQUENCE CHARACTERISTICS:
        ( A ) LENGTH: 417 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Met Thr Leu Ser Pro Glu Lys Gln His Val Arg Pro Arg Asp Ala Ala
1               5                 10              15

Asp Asn Asp Pro Val Ala Val Ala Arg Gly Leu Ala Glu Lys Trp Arg
          20                 25              30

Ala Thr Ala Val Glu Arg Asp Arg Ala Gly Gly Ser Ala Thr Ala Glu
       35                 40              45

```
Arg Glu Asp Leu Arg Ala Ser Ala Leu Leu Ser Leu Leu Val Pro Arg
     50                  55                  60
Glu Tyr Gly Gly Trp Gly Ala Asp Trp Pro Thr Ala Ile Glu Val Val
 65              70                  75                      80
Arg Glu Ile Ala Ala Ala Asp Gly Ser Leu Gly His Leu Phe Gly Tyr
             85                  90                      95
His Leu Thr Asn Ala Pro Met Ile Glu Leu Ile Gly Ser Gln Glu Gln
            100             105             110
Glu Glu His Leu Tyr Thr Gln Ile Ala Gln Asn Asn Trp Trp Thr Gly
        115             120             125
Asn Ala Ser Ser Glu Asn Asn Ser His Val Leu Asp Trp Lys Val Ser
    130             135             140
Ala Thr Pro Thr Glu Asp Gly Gly Tyr Val Leu Asn Gly Thr Lys His
145             150             155                     160
Phe Cys Ser Gly Ala Lys Gly Ser Asp Leu Leu Phe Val Phe Gly Val
                165             170             175
Val Gln Asp Asp Ser Pro Gln Gln Gly Ala Ile Ile Ala Ala Ala Ile
            180             185             190
Pro Thr Ser Arg Ala Gly Val Thr Pro Asn Asp Asp Trp Ala Ala Ile
        195             200             205
Gly Met Arg Gln Thr Asp Ser Gly Ser Thr Asp Phe His Asn Val Lys
    210             215             220
Val Glu Pro Asp Glu Val Leu Gly Ala Pro Asn Ala Phe Val Leu Ala
225             230             235                     240
Phe Ile Gln Ser Glu Arg Gly Ser Leu Phe Ala Pro Ile Ala Gln Leu
                245             250             255
Ile Phe Ala Asn Val Tyr Leu Gly Ile Ala His Gly Ala Leu Asp Ala
            260             265             270
Ala Arg Glu Tyr Thr Arg Thr Gln Ala Arg Pro Trp Thr Pro Ala Gly
        275             280             285
Ile Gln Gln Ala Thr Glu Asp Pro Tyr Thr Ile Arg Ser Tyr Gly Glu
    290             295             300
Phe Thr Ile Ala Leu Gln Gly Ala Asp Ala Ala Ala Arg Glu Ala Ala
305             310             315                     320
His Leu Leu Gln Thr Val Trp Asp Lys Gly Asp Ala Leu Thr Pro Glu
                325             330             335
Asp Arg Gly Glu Leu Met Val Lys Val Ser Gly Val Lys Ala Leu Ala
            340             345             350
Thr Asn Ala Ala Leu Asn Ile Ser Ser Gly Val Phe Glu Val Ile Gly
        355             360             365
Ala Arg Gly Thr His Pro Arg Tyr Gly Phe Asp Arg Phe Trp Arg Asn
    370             375             380
Val Arg Thr His Ser Leu His Asp Pro Val Ser Tyr Lys Ile Ala Asp
385             390             395                     400
Val Gly Lys His Thr Leu Asn Gly Gln Tyr Pro Ile Pro Gly Phe Thr
                405             410             415
Ser
```

( 2 ) INFORMATION FOR SEQ ID NO:4:

( i ) SEQUENCE CHARACTERISTICS:
        ( A ) LENGTH: 5535 base pairs
        ( B ) TYPE: nucleic acid
        ( C ) STRANDEDNESS: double
        ( D ) TOPOLOGY: linear (ii) MOLECULE TYPE: DNA (genomic)

(ix) FEATURE:
(A) NAME/KEY: CDS
(B) LOCATION: 2148..3245

(xi) SEQUENCE DESCRIPTION: SEQ ID NO:4:

| | | | | | | |
|---|---|---|---|---|---|---|
| GCATGCACGT | CGCGCCGACG | CATTTGCGCG | CACGGCTCCG | GGCAGTTCTC | GCGGCGCTGG | 60 |
| AGGCACGGAT | GGGCACCCTC | AACGAACTCA | CCCAAACCAC | GCCGATAGCG | ATCCTCGCCG | 120 |
| AAACCCTCGG | CTACAGCCCT | CAGACATTGG | AAGCTCATGC | GCGACGCATC | CGGATCGACC | 180 |
| TTTGCACGCT | ACGTGGCGAC | GCGGCTGGAC | TGACGCTGGA | GGTCCGACCC | GACGTGTGTG | 240 |
| GTGTAGCGCC | GCTTAACGGG | TGCGCACGGC | GGGACATCGG | CCAGCTGGCT | TGCCCCTCCT | 300 |
| CCGCAGGTAG | TCGACCACCC | CTTCCCGCAG | CGGTCGGAGG | TGATCGACCG | TTAGGGTCAT | 360 |
| TTGCTCGCAG | ATCGGCTGAT | GTTGCCGATC | GACGTGGTCG | ACGGGACACG | CTCGCGATTG | 420 |
| GCATGGCGTC | CGGTGCATAC | ACGACGATCT | AACCAGATCG | ACGGTTTTGA | GCGTCGGTCA | 480 |
| ACGTCGACTC | GATGCGCCGT | GCGAGTGAGA | TCCTTTGTGG | TGCTTGGCTA | TTGACCTCGA | 540 |
| CAAGGATAGA | GATTCGAAGG | ACCTCGGATC | GACCCAAATG | CGGACGGCCG | GCAGCGGCGA | 600 |
| AGGCGGCCAA | GTCATCGGCA | CCGTCACCGT | CACCTTGACC | CGACGTGCCC | CGTGGTTCAA | 660 |
| GGCCTGAATT | TGGCTGGTGG | AGCATTGAAA | TCAGGTGAAG | TTTAACGGTG | GGCACACCCC | 720 |
| GGGGGTGGGG | GTGAGACTGC | TTAGCGACAG | GAATCTAGCC | ATGATTGACA | TTTAAAGGAC | 780 |
| GCATACGCGA | TGACTCAACA | ACGACAAATG | CATCTGGCCG | GTTTCTTCTC | GGCCGGCAAT | 840 |
| GTGACTCATG | CACATGGGGC | GTGGCGGCAC | ACGGACGCGT | CGAATGACTT | TCTGTCGGGG | 900 |
| AAGTACTACC | AACACATCGC | CCGTACTCTG | GAGCGCGGCA | AGTTCGATCT | GTTGTTTCTG | 960 |
| CCTGACGGGT | TGGCCGTCGA | GGACAGCTAC | GGGGACAACC | TGGACACCGG | TGTCGGCCTG | 1020 |
| GGCGGGCAGG | GTGCAGTCGC | CTTGGAGCCG | GCCAGTGTGG | TCGCAACCAT | GGCCGCGGTG | 1080 |
| ACCGAGCACC | TGGGTCTTGG | GGCAACCATT | TCGGCGACCT | ACTATCCCCC | GTATCACGTT | 1140 |
| GCTCGGGTGT | TCGCGACGCT | CGATCAGTTG | TCAGGGGGTC | GGGTGTCCTG | GAACGTCGTC | 1200 |
| ACCTCGCTCA | ACGACGCTGA | AGCGCGCAAC | TTCGGCATTA | ATCAGCATCT | GGAACACGAC | 1260 |
| GCCCGCTATG | ACCGCGCCGA | TGAGTTCTTG | GAAGCGGTCA | AGAAACTCTG | GAACAGCTGG | 1320 |
| GACGAGGACG | CCCTCGTGCT | GGACAAGGCG | GCCGGCGTGT | CGCCGATCC | CGCGAAGGTG | 1380 |
| CACTACGTCG | ATCACCACGG | GGAGTGGCTG | AATGTGCGCG | GACCTCTGCA | GGTACCGCGT | 1440 |
| TCACCTCAGG | GTGAGCCGGT | GATCCTGCAG | GCCGGCCTGT | CGCCCCGGGG | TCGGCGCTTC | 1500 |
| GCCGGGAAGT | GGGCCGAGGC | CGTCTTCAGT | CTTGCACCCA | ACCTCGAGGT | GATGCAGGCC | 1560 |
| ACCTACCAGG | GCATCAAAGC | CGAGGTCGAC | GCTGCGGGGC | GCGATCCCGA | TCAGACGAAA | 1620 |
| ATCTTCACCG | CCGTGATGCC | GGTACTCGGC | GAAAGCCAGG | CGGTGGCACA | GGAACGACTG | 1680 |
| GAATATCTCA | ACAGTCTGGT | CCATCCGGAA | GTGGGACTGT | CGACGCTATC | CAGTCACACC | 1740 |
| GGCATCAACC | TGGCGGCGTA | CCCTCTCGAC | ACTCCGATCA | AGGACATCCT | GCGGGATCTG | 1800 |
| CAGGATCGGA | ATGTCCCGAC | GCAACTGCAC | ATGTTCGCCG | CCGCAACGCA | CAGCGAAGAG | 1860 |
| CTCACGCTGG | CGGAAATGGG | TCGGCGCTAT | GGAACCAACG | TGGGGTTCGT | TCCTCAGTGG | 1920 |
| GCCGGTACCG | GGGAGCAGAT | CGCTGACGAG | CTGATCCGCC | ACTTCGAGGG | CGGCGCCGCG | 1980 |
| GATGGTTTCA | TCATCTCTCC | GGCCTTCCTG | CCGGGCTCCT | ACGACGAGTT | CGTCGACCAG | 2040 |
| GTGGTTCCGG | TTCTGCAGGA | TCGCGGCTAC | TTCCGCACCG | AGTACCAGGG | CAACACTCTG | 2100 |
| CGCGACCACT | TGGGTCTGCG | CGTACCACAA | CTGCAAGGAC | AACCTTC ATG | ACA AGC | 2156 |
| | | | | | Met Thr Ser | |

| | | | | | | | | | | | | | | | | |
|---|---|---|---|---|---|---|---|---|---|---|---|---|---|---|---|---|
| CGC | GTC | GAC | CCC | GCA | AAC | CCC | GGT | TCA | GAA | CTC | GAT | TCC | GCC | ATC | CGC | 2204 |
| Arg | Val | Asp | Pro | Ala | Asn | Pro | Gly | Ser | Glu | Leu | Asp | Ser | Ala | Ile | Arg | |
| | 5 | | | | 10 | | | | | 15 | | | | | | |
| GAC | ACA | CTG | ACC | TAC | AGC | AAC | TGC | CCG | GTA | CCC | AAC | GCT | CTG | CTC | ACG | 2252 |
| Asp | Thr | Leu | Thr | Tyr | Ser | Asn | Cys | Pro | Val | Pro | Asn | Ala | Leu | Leu | Thr | |
| 20 | | | | | 25 | | | | | 30 | | | | | 35 | |
| GCA | TCG | GAA | TCG | GGC | TTC | CTC | GAC | GCC | GCC | GGC | ATC | GAA | CTC | GAC | GTC | 2300 |
| Ala | Ser | Glu | Ser | Gly | Phe | Leu | Asp | Ala | Ala | Gly | Ile | Glu | Leu | Asp | Val | |
| | | | | 40 | | | | | 45 | | | | | 50 | | |
| CTC | AGC | GGC | CAG | CAG | GGC | ACG | GTT | CAT | TTC | ACC | TAC | GAC | CAG | CCT | GCC | 2348 |
| Leu | Ser | Gly | Gln | Gln | Gly | Thr | Val | His | Phe | Thr | Tyr | Asp | Gln | Pro | Ala | |
| | | | | 55 | | | | | 60 | | | | | 65 | | |
| TAC | ACC | CGT | TTT | GGG | GGT | GAG | ATC | CCG | CCA | CTG | CTC | AGC | GAG | GGG | TTG | 2396 |
| Tyr | Thr | Arg | Phe | Gly | Gly | Glu | Ile | Pro | Pro | Leu | Leu | Ser | Glu | Gly | Leu | |
| | | | 70 | | | | | 75 | | | | | 80 | | | |
| CGG | GCA | CCT | GGG | CGC | ACG | CGT | CTA | CTC | GGC | ATC | ACC | CCG | CTC | TTG | GGG | 2444 |
| Arg | Ala | Pro | Gly | Arg | Thr | Arg | Leu | Leu | Gly | Ile | Thr | Pro | Leu | Leu | Gly | |
| | 85 | | | | | 90 | | | | | 95 | | | | | |
| CGC | CAG | GGC | TTC | TTT | GTC | CGC | GAC | GAC | AGC | CCG | ATC | ACA | GCG | GCC | GCC | 2492 |
| Arg | Gln | Gly | Phe | Phe | Val | Arg | Asp | Asp | Ser | Pro | Ile | Thr | Ala | Ala | Ala | |
| 100 | | | | | 105 | | | | | 110 | | | | | 115 | |
| GAC | CTT | GCC | GGA | CGT | CGA | ATC | GGC | GTC | TCG | GCC | TCG | GCA | ATT | CGC | ATC | 2540 |
| Asp | Leu | Ala | Gly | Arg | Arg | Ile | Gly | Val | Ser | Ala | Ser | Ala | Ile | Arg | Ile | |
| | | | | 120 | | | | | 125 | | | | | 130 | | |
| CTG | CGC | GGC | CAG | CTG | GGC | GAC | TAC | CTC | GAG | TTG | GAT | CCC | TGG | CGG | CAA | 2588 |
| Leu | Arg | Gly | Gln | Leu | Gly | Asp | Tyr | Leu | Glu | Leu | Asp | Pro | Trp | Arg | Gln | |
| | | | 135 | | | | | 140 | | | | | 145 | | | |
| ACG | CTG | GTA | GCG | CTG | GGC | TCG | TGG | GAG | GCG | CGC | GCC | TTG | TTG | CAC | ACC | 2636 |
| Thr | Leu | Val | Ala | Leu | Gly | Ser | Trp | Glu | Ala | Arg | Ala | Leu | Leu | His | Thr | |
| | | 150 | | | | | 155 | | | | | 160 | | | | |
| CTT | GAG | CAC | GGT | GAA | CTG | GGT | GTG | GAC | GAC | GTC | GAG | CTG | GTG | CCG | ATC | 2684 |
| Leu | Glu | His | Gly | Glu | Leu | Gly | Val | Asp | Asp | Val | Glu | Leu | Val | Pro | Ile | |
| | 165 | | | | | 170 | | | | | 175 | | | | | |
| AGC | AGT | CCT | GGT | GTC | GAT | GTT | CCC | GCT | GAG | CAG | CTC | GAA | GAA | TCG | GCG | 2732 |
| Ser | Ser | Pro | Gly | Val | Asp | Val | Pro | Ala | Glu | Gln | Leu | Glu | Glu | Ser | Ala | |
| 180 | | | | | 185 | | | | | 190 | | | | | 195 | |
| ACC | GTC | AAG | GGT | GCG | GAC | CTC | TTT | CCC | GAT | GTC | GCC | CGC | GGT | CAG | GCC | 2780 |
| Thr | Val | Lys | Gly | Ala | Asp | Leu | Phe | Pro | Asp | Val | Ala | Arg | Gly | Gln | Ala | |
| | | | 200 | | | | | 205 | | | | | 210 | | | |
| GCG | GTG | TTG | GCC | AGC | GGA | GAC | GTT | GAC | GCC | CTG | TAC | AGT | TGG | CTG | CCC | 2828 |
| Ala | Val | Leu | Ala | Ser | Gly | Asp | Val | Asp | Ala | Leu | Tyr | Ser | Trp | Leu | Pro | |
| | | | | 215 | | | | | 220 | | | | | 225 | | |
| TGG | GCC | GGG | GAG | TTG | CAA | GCC | ACC | GGG | GCC | CGC | CCA | GTG | GTG | GAT | CTC | 2876 |
| Trp | Ala | Gly | Glu | Leu | Gln | Ala | Thr | Gly | Ala | Arg | Pro | Val | Val | Asp | Leu | |
| | | 230 | | | | | 235 | | | | | 240 | | | | |
| GGC | CTC | GAT | GAG | CGC | AAT | GCC | TAC | GCC | AGT | GTG | TGG | ACG | GTC | AGC | AGC | 2924 |
| Gly | Leu | Asp | Glu | Arg | Asn | Ala | Tyr | Ala | Ser | Val | Trp | Thr | Val | Ser | Ser | |
| | 245 | | | | | 250 | | | | | 255 | | | | | |
| GGG | CTG | GTT | CGC | CAG | CGA | CCT | GGC | CTT | GTT | CAA | CGA | CTG | GTC | GAC | GCG | 2972 |
| Gly | Leu | Val | Arg | Gln | Arg | Pro | Gly | Leu | Val | Gln | Arg | Leu | Val | Asp | Ala | |
| 260 | | | | | 265 | | | | | 270 | | | | | 275 | |
| GCC | GTC | GAC | GCC | GGG | CTG | TGG | GCA | CGC | GAT | CAT | TCC | GAC | GCG | GTG | ACC | 3020 |
| Ala | Val | Asp | Ala | Gly | Leu | Trp | Ala | Arg | Asp | His | Ser | Asp | Ala | Val | Thr | |
| | | | | 280 | | | | | 285 | | | | | 290 | | |
| AGC | CTG | CAC | GCC | GCG | AAC | CTG | GGC | GTA | TCG | ACC | GGA | GCA | GTA | GGC | CAG | 3068 |
| Ser | Leu | His | Ala | Ala | Asn | Leu | Gly | Val | Ser | Thr | Gly | Ala | Val | Gly | Gln | |
| | | | 295 | | | | | 300 | | | | | 305 | | | |
| GGC | TTC | GGC | GCC | GAC | TTC | CAG | CAG | CGT | CTG | GTT | CCA | CGC | CTG | GAT | CAC | 3116 |
| Gly | Phe | Gly | Ala | Asp | Phe | Gln | Gln | Arg | Leu | Val | Pro | Arg | Leu | Asp | His | |

|  |  |  |  |  |  |  |  |  |  |  |
|---|---|---|---|---|---|---|---|---|---|---|
|  |  | 310 |  |  |  | 315 |  |  |  | 320 |

```
GAC  GCC  CTC  GCC  CTC  CTG  GAG  CGC  ACA  CAG  CAA  TTC  CTG  CTC  ACC  AAC       3164
Asp  Ala  Leu  Ala  Leu  Leu  Glu  Arg  Thr  Gln  Gln  Phe  Leu  Leu  Thr  Asn
     325                     330                          335

AAC  TTG  CTG  CAG  GAA  CCC  GTC  GCC  CTC  GAT  CAG  TGG  GCG  GCT  CCG  GAA       3212
Asn  Leu  Leu  Gln  Glu  Pro  Val  Ala  Leu  Asp  Gln  Trp  Ala  Ala  Pro  Glu
340                      345                     350                          355

TTT  CTG  AAC  AAC  AGC  CTC  AAT  CGC  CAC  CGA  TAGGAACATC  CGCATGACAC             3262
Phe  Leu  Asn  Asn  Ser  Leu  Asn  Arg  His  Arg
                    360                    365
```

| | | | | |
|---|---|---|---|---|
| TGTCACCTGA | AAAGCAGCAC | GTTCGACCAC | GCGACGCCGC | CGACAACGAT | CCCGTCGCGG | 3322 |
| TTGCCCGTGG | GCTAGCCGAA | AAGTGGCGAG | CCACCGCCGT | CGAGCGTGAT | CGCGCCGGGG | 3382 |
| GTTCGGCAAC | AGCCGAGCGC | GAAGACCTGC | GCGCGAGCGC | GCTGCTGTCG | CTCCTCGTCC | 3442 |
| CGCGCGAATA | CGGCGGCTGG | GGCGCAGACT | GGCCCACCGC | CATCGAGGTC | GTCCGCGAAA | 3502 |
| TCGCGGCAGC | CGATGGATCT | TTGGGACACC | TGTTCGGATA | CCACCTCACC | AACGCCCCGA | 3562 |
| TGATCGAACT | GATCGGCTCG | CAGGAACAAG | AAGAACACCT | GTACACCCAG | ATCGCGCAGA | 3622 |
| ACAACTGGTG | GACCGGAAAT | GCCTCCAGCG | AGAACAACAG | CCACGTGCTG | GACTGGAAGG | 3682 |
| TCAGCGCCAC | CCCGACCGAA | GACGGCGGCT | ACGTGCTCAA | TGGCACGAAG | CACTTCTGCA | 3742 |
| GCGGCGCCAA | GGGGTCGGAC | CTGCTGTTCG | TGTTCGGCGT | CGTCCAGGAT | GATTCTCCGC | 3802 |
| AGCAGGGTGC | GATCATTGCT | GCCGCTATCC | CGACATCGCG | GGCTGGCGTT | ACGCCCAACG | 3862 |
| ACGACTGGGC | CGCCATCGGC | ATGCGGCAGA | CCGACAGCGG | TTCCACGGAC | TTCCACAACG | 3922 |
| TCAAGGTCGA | GCCTGACGAA | GTGCTGGGCG | CGCCCAACGC | CTTCGTTCTC | GCCTTCATAC | 3982 |
| AATCCGAGCG | CGGCAGCCTC | TTCGCGCCCA | TAGCGCAATT | GATCTTCGCC | AACGTCTATC | 4042 |
| TGGGGATCGC | GCACGGCGCA | CTCGATGCCG | CCAGGGAGTA | CACCCGTACC | CAGGCGAGGC | 4102 |
| CCTGGACACC | GGCCGGTATT | CAACAGGCAA | CCGAGGATCC | CTACACCATC | CGCTCCTACG | 4162 |
| GTGAGTTCAC | CATCGCATTG | CAGGGAGCTG | ACGCCGCCGC | CCGTGAAGCG | GCCCACCTGC | 4222 |
| TGCAGACGGT | GTGGGACAAG | GGCGACGCGC | TCACCCCCGA | GGACCGCGGC | GAACTGATGG | 4282 |
| TGAAGGTCTC | GGGAGTCAAA | GCGTTGGCCA | CCAACGCCGC | CCTCAACATC | AGCAGCGGCG | 4342 |
| TCTTCGAGGT | GATCGGCGCG | CGCGGAACAC | ATCCCAGGTA | CGGTTTCGAC | CGCTTCTGGC | 4402 |
| GCAACGTGCG | CACCCACTCC | CTGCACGACC | CGGTGTCCTA | CAAGATCGCC | GACGTCGGCA | 4462 |
| AGCACACCTT | GAACGGTCAA | TACCCGATTC | CCGGCTTCAC | CTCCTGAGGA | TCTGAGGCGC | 4522 |
| TGATCGAGGC | CGAGGCCACC | GCGCGGCCGA | GTCGCGAATC | GCCCGCCGAT | ACTCAGCTTC | 4582 |
| TCCATACGTA | CGGGTGCACA | CAAGGAGATA | TTGTCAAGAC | CTGTGGATGA | GGGTGTTTCA | 4642 |
| GGCGACCTCC | GTTTCGCTTG | ATTCGTCGGG | CTCAGCGGGT | GAGATGTCGA | TGGGTCGTTC | 4702 |
| GAGCAGCTTG | CCTTTGTGGA | ACACCGCGCC | GGCACGGACC | AGCGCGACCA | GATGGGGGGC | 4762 |
| GTTGACCGCC | GCCAGCGGGC | TTGTGCGGCG | TCGATCAGCT | TGTAGGCCAT | GGCAATCCCG | 4822 |
| CTGCGACGTG | ACCCAGGGCC | CTTGGTGACC | TTGGTTCGCA | ACCGCACGGT | CGCAAACGTC | 4882 |
| GATTCGATCG | GATTCGTAGT | GCGCAAGTGG | ATCCAGTGCT | CGGCCGGGTA | CCGGTAGAAC | 4942 |
| TCCAGGAGCA | CGTCGGCGTC | GTCGACGATC | TTGGCGACCG | CCTTGGGGTA | CTTCGCGCCG | 5002 |
| TAATCTACCT | CGAAGGCCTT | GATCGCGACC | TGGGCCTTGT | CGATGTCCTC | GGCGTTGTAG | 5062 |
| ATTTCCCGCA | TCGCCGCGGT | CGCACCTGGA | TGAGCCGACT | TGGGCAGCGC | AGCAAGCACA | 5122 |
| TTGGCCTGCT | TGTGAAACCA | GCAGCGCTGT | TCACGGGTAT | CCGGAAACAC | CTCCCGCAGT | 5182 |
| GCCTTCCAGA | ACCCCAGCGC | CCCATCACCG | ACGGCCAGCA | CCGGGGCGGT | CATCCCGCGG | 5242 |

|                                                                                  |      |
|----------------------------------------------------------------------------------|------|
| CGTCGGCATG AGCGCAGCAG ATCAGCCCAC GACTCTGTGG ACTCCCGGAA CCCATCGGTG                 | 5302 |
| AGCGCGACGA GCTCCTTGCG GCCGTCGGCG CGGACGCCGA TCATCACGAG CAAGCACAGC                 | 5362 |
| TTCTCCTGCT CCAGGCGGAC ATTGAGATGG ATGCCGTCGA CCCATAGGTA CACGAAATCG                 | 5422 |
| GTGCCCGAGA GATCCCGGTC GGCGAAGGCC TTCGCCTCGT CCTGCCATTG CGCGGTCAGC                 | 5482 |
| CGGGTGATCG TCGAGGCCGA CAGCCCGGCA CCAGTGCCGA GGAACTGCTC CAA                       | 5535 |

( 2 ) INFORMATION FOR SEQ ID NO:5:

( i ) SEQUENCE CHARACTERISTICS:
        ( A ) LENGTH: 365 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Thr Ser Arg Val Asp Pro Ala Asn Pro Gly Ser Glu Leu Asp Ser
 1               5                  10                  15
Ala Ile Arg Asp Thr Leu Thr Tyr Ser Asn Cys Pro Val Pro Asn Ala
                20                  25                  30
Leu Leu Thr Ala Ser Glu Ser Gly Phe Leu Asp Ala Ala Gly Ile Glu
                35                  40                  45
Leu Asp Val Leu Ser Gly Gln Gln Gly Thr Val His Phe Thr Tyr Asp
        50                  55                  60
Gln Pro Ala Tyr Thr Arg Phe Gly Gly Glu Ile Pro Pro Leu Leu Ser
65                  70                  75                  80
Glu Gly Leu Arg Ala Pro Gly Arg Thr Arg Leu Leu Gly Ile Thr Pro
                85                  90                  95
Leu Leu Gly Arg Gln Gly Phe Phe Val Arg Asp Asp Ser Pro Ile Thr
            100                 105                 110
Ala Ala Ala Asp Leu Ala Gly Arg Arg Ile Gly Val Ser Ala Ser Ala
            115                 120                 125
Ile Arg Ile Leu Arg Gly Gln Leu Gly Asp Tyr Leu Glu Leu Asp Pro
        130                 135                 140
Trp Arg Gln Thr Leu Val Ala Leu Gly Ser Trp Glu Ala Arg Ala Leu
145                 150                 155                 160
Leu His Thr Leu Glu His Gly Glu Leu Gly Val Asp Asp Val Glu Leu
                165                 170                 175
Val Pro Ile Ser Ser Pro Gly Val Asp Val Pro Ala Glu Gln Leu Glu
            180                 185                 190
Glu Ser Ala Thr Val Lys Gly Ala Asp Leu Phe Pro Asp Val Ala Arg
            195                 200                 205
Gly Gln Ala Ala Val Leu Ala Ser Gly Asp Val Asp Ala Leu Tyr Ser
        210                 215                 220
Trp Leu Pro Trp Ala Gly Glu Leu Gln Ala Thr Gly Ala Arg Pro Val
225                 230                 235                 240
Val Asp Leu Gly Leu Asp Glu Arg Asn Ala Tyr Ala Ser Val Trp Thr
                245                 250                 255
Val Ser Ser Gly Leu Val Arg Gln Arg Pro Gly Leu Val Gln Arg Leu
            260                 265                 270
Val Asp Ala Ala Val Asp Ala Gly Leu Trp Ala Arg Asp His Ser Asp
        275                 280                 285
Ala Val Thr Ser Leu His Ala Ala Asn Leu Gly Val Ser Thr Gly Ala
        290                 295                 300
Val Gly Gln Gly Phe Gly Ala Asp Phe Gln Gln Arg Leu Val Pro Arg
```

| 305 | | | | 310 | | | | 315 | | | | 320 | |
|---|---|---|---|---|---|---|---|---|---|---|---|---|---|

Leu Asp His Asp Ala Leu Ala Leu Leu Glu Arg Thr Gln Gln Phe Leu
                    325                     330                     335

Leu Thr Asn Asn Leu Leu Gln Glu Pro Val Ala Leu Asp Gln Trp Ala
                340                     345                 350

Ala Pro Glu Phe Leu Asn Asn Ser Leu Asn Arg His Arg
            355                 360                 365

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTTTTCCCAG TCACGAC                          17

(2) INFORMATION FOR SEQ ID NO:7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AACAGCTATG ACCATG                           16

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCGAATTCCG CACCGAGTAC C                    21

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATCCATATGC GCACTACGAA TCC                  23

(2) INFORMATION FOR SEQ ID NO:10:

(i) SEQUENCE CHARACTERISTICS:
        (A) LENGTH: 50 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:10:

GGAATTCTAG ACATATGAGG AACAGACCAT GACTCAACAA CGACAAATGC    50

( 2 ) INFORMATION FOR SEQ ID NO:11:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGAATTCTAG AATCAGGGGT CGACGCGGCT TGTCATG    37

( 2 ) INFORMATION FOR SEQ ID NO:12:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGAATTCAGA TCTCATATGA GGAAACAGAC CATGACAAGC CGCGTCGACC    50

( 2 ) INFORMATION FOR SEQ ID NO:13:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CGAATTCAGA TCTAATTCCT ATCGGTGGCG ATTGAGGC    38

( 2 ) INFORMATION FOR SEQ ID NO:14:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GGAATTCTTA ACATATGAGG AAACAGACCA TGACACTGTC ACCTGA    46

( 2 ) INFORMATION FOR SEQ ID NO:15:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CGAATTCTTA ATCAGCGCCT CAGATCCTCA G    31

( 2 ) INFORMATION FOR SEQ ID NO:16:

( i ) SEQUENCE CHARACTERISTICS:
        ( A ) LENGTH: 116 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

```
CATATGCATT TAAAGGACGC ATACGCGATG ACTCAACAAC GACAATGCAT CTGGCCGGGT      60

ATACGTAAAT TTCCTGCGTA TGCGCTACTG AGTTGTTGCT GTTACGTAGA CCGGCC        116
```

RECOMBINANT DNA ENCODING A DESULFURIZATION BIOCATALYST

This application is a division of application Ser. No. 08/304,081 filed Sep. 1, 1994 which is a divisional of 08/089,755 filed Jul. 9, 1993 now U.S. Pat. No. 5,356,801 which is a continuation-in-part of 07/911,845, now abandoned filed Jul. 10, 1992.

BACKGROUND

Sulfur contaminants in fossil fuels can create problems in refinery processes which can be costly to rectify. The sulfur contaminants that occur in fossil fuels fall into either of the following general classes: mineralized (inorganic, e.g., pyritic) sulfur and organic sulfur (sulfur that is covalently bound to carbonaceous molecules, referred to as organosulfur compounds). The presence of sulfur has been correlated with corrosion of pipeline, pumping and refining equipment, and with premature breakdown of combustion engines. Sulfur also poisons many catalysts which are used in the refining of fossil fuels. Moreover, the atmospheric emission of sulfur combustion products, such as sulfur dioxide, leads to the form of acid deposition known as acid rain. Acid rain has lasting deleterious effects on aquatic and forest ecosystems, as well as on agricultural areas located downwind of combustion facilities. Monticello, D. J. and W. R. Finnerty, (1985) *Ann. Rev. Microbiol.* 39:371–389. Regulations such as the Clean Air Act of 1964 require the removal of sulfur, either pre- or post-combustion, from virtually all coal- and petroleum-based fuels. Conformity with such legislation has become increasingly problematic due to the rising need to utilize lower grade, higher-sulfur fossil fuels as clean-burning, low-sulfur petroleum reserves become depleted, as well as the progressive reductions in sulfur emissions required by regulatory authorities. Monticello, D. J. and J. J. Kilbane, "Practical Considerations in Biodesulfurization of Petroleum", *IGT's 3d Intl. Symp. on Gas, Oil, Coal, and Env. Biotech.*, (Dec. 3–5, 1990) New Orleans, La.

One technique which is currently employed for the pre-combustion removal of organic sulfur from liquid fossil fuels, e.g., petroleum, is hydrodesulfurization (HDS). HDS is suitable for the desulfurization of fossil fuels wherein organosulfur compounds account for a significant, e.g., a major, proportion of all sulfur contaminants present. HDS is thus useful for treating crude oil or bitumen, petroleum distillate fractions or refining intermediates, liquid motor fuels, and the like. HDS is more particularly described in Shih, S. S. et al., "Deep Desulfurization of Distillate Components", Abstract No. 264B AIChE Chicago Annual Meeting, presented Nov. 12, 1990, (complete text available upon request from the American Institute of Chemical Engineers); Gary, J. H. and G. E. Handwerk, (1975) *Petroleum Refining: Technology and Economics*, Marcel Dekker, Inc., New York, pp. 114–120, and Speight, J. G., (1981) *The Desulfurization of Heavy Oils and Residue*, Marcel Dekker, Inc., New York, pp. 119–127. HDS is based on the reductive, conversion of organic sulfur into hydrogen sulfide ($H_2S$) in the presence of a metal catalyst. HDS is carried out under conditions of elevated temperature and pressure. The hydrogen sulfide produced as a result of HDS is a corrosive gaseous substance, which is stripped from the fossil fuel by known techniques. Elevated or persistent levels of hydrogen sulfide are known to poison (inactivate) the HDS catalyst, complicating the desulfurization of liquid fossil fuels that are high in sulfur.

Organic sulfur in both coal and petroleum fossil fuels is present in a myriad of compounds, some of which are termed labile in that they can readily be desulfurized, others of which are termed refractory in that they do not easily yield to conventional desulfurization treatment, e.g., by HDS. Shih, S.S. et al. Frequently, then, even HDS-treated fossil fuels must be post-combustively desulfurized using an apparatus such as a flue scrubber. Flue scrubbers are expensive to install and difficult to maintain, especially for small combustion facilities. Moreover, of the sulfur-generated problems noted above, the use of flue scrubbers in conjunction with HDS is directed to addressing environmental acid deposition, rather than other sulfur-associated problems, such as corrosion of machinery and poisoning of catalysts.

Recognizing these and other shortcomings of HDS, many investigators have pursued the development of microbial desulfurization (MDS). MDS is generally described as the harnessing of metabolic processes of suitable bacteria to the desulfurization of fossil fuels. Thus, MDS typically involves mild (e.g., ambient or physiological) conditions, and does not involve the extremes of temperature and pressure required for HDS. It is also generally considered advantageous that biological desulfurizing agents can renew or replenish themselves under suitable conditions. Microbial desulfurization technology is reviewed in Monticello and Finnerty (1985), 39 *Ann. Rev. Microbiol.* 371–389 and Bhadra et al. (1987), 5 *Biotech. Adv.* 1–27. Hartdegan et al. (1984), 5 *Chem. Eng. Progress* 63–67 and Kilbane (1989), 7 *Trends Biotechnol.* (No. 4) 97–101 provide additional commentary on developments in the field.

Several investigators have reported mutagenizing naturally-occurring bacteria into mutant strains with the acquired capability of breaking down, i.e., catabolizing, dibenzothiophene (DBT). Hartdegan, F. J. et al., (May 1984) *Chem. Eng. Progress* 63–67. DBT is representative of the class of organic sulfur molecules found in fossil fuels from which it is most difficult to remove sulfur by HDS. Most of the reported mutant microorganisms act upon DBT nonspecifically, by cleaving carbon-carbon bonds, thereby releasing sulfur in the form of small organic breakdown products. One consequence of this microbial action is that the fuel value of a fossil fuel so treated is degraded. Isbister and Doyle, however, reported the derivation of a mutant strain of Pseudomonas which appeared to be capable of selectively liberating sulfur from DBT, thereby preserving the fuel value of treated fossil fuels. U.S. Pat. No. 4,562,156.

Kilbane recently reported the mutagenesis of a mixed bacterial culture, producing a bacterial consortium which appeared capable of selectively liberating sulfur from DBT by an oxidative pathway. *Resour. Cons. Recycl.* 3:69–79 (1990). A strain of Rhodococcus was subsequently isolated from the consortium. This strain, which has been deposited with the American Type Culture collection under the terms of the Budapest Treaty as ATCC No. 53968 and also referred to as IGTS8, is a source of biocatalytic activity as described herein. Microorganisms of the ATCC No. 53968 strain liberate sulfur from forms of organic sulfur known to be present in fossil fuels, including DBT, by the selective, oxidative cleavage of carbon-sulfur bonds in organic sulfur molecules. Kilbane has described the isolation and characteristics of this strain in detail in U.S. Pat. No. 5,104,801.

SUMMARY OF THE INVENTION

This invention relates in one aspect to a deoxyribonucleic acid (DNA) molecule containing one or more genes encoding one or more enzymes that, singly or in concert with each other, act as a biocatalyst that desulfurizes a fossil fuel that contains organic sulfur molecules. The DNA molecule of the present invention can be purified and isolated from a natural source, or can be a fragment or portion of a recombinant DNA molecule that is, e.g., integrated into the genome of a non-human host organism. The gene or genes of the present invention can be obtained from, e.g., a strain of *Rhodococcus rhodochrous* microorganisms having suitable biocatalytic activity. That is, the gene or genes of the present invention can be obtained from a non-human organism, e.g., a microorganism, that expresses one or more enzymes that, singly or in concert with each other, act as a desulfurizing biocatalyst. Biocatalysis, as described more fully below, is the selective oxidative cleavage of carbon-sulfur bonds in organosulfur compounds. The present invention is particularly useful for the desulfurization of fossil fuels that contain organosulfur compounds, e.g., DBT.

The invention further relates to recombinant DNA vectors, recombinant DNA plasmids and non-human organisms that contain foreign (recombinant, heterologous) DNA encoding a biocatalyst capable of desulfurizing a fossil fuel which contains organosulfur compounds. Such organisms are referred to herein as host organisms.

The invention described herein thus encompasses ribonucleic acid (RNA) transcripts of the gene or genes of the present invention, as well as polypeptide expression product(s) of the gene or genes of the present invention. The present polypeptide expression products, after such post-translational processing and/or folding as is necessary, and in conjunction with any coenzymes, cofactors or coreactants as are necessary, form one or more protein biocatalysts (enzymes) that, singly or in concert with each other, catalyze (promote, direct or facilitate) the removal of sulfur from organosulfur compounds that are found in fossil fuels. This is accomplished by the selective, oxidative cleavage of carbon-sulfur bonds in said compounds. The biocatalyst of the present invention can be a non-human host organism, viable (e.g., cultured) or non-viable (e.g., heat-killed) containing the DNA of the present invention and expressing one or more enzymes encoded therein, or it can be a cell-free preparation derived from said organism and containing said one or more biocatalytic enzymes.

In another aspect, the present invention relates to a method of desulfurizing a fossil fuel using the above mentioned non-human organism, said organism expressing a desulfurizing biocatalyst. Alternatively, the present invention relates to a method of desulfurizing a fossil fuel using a biocatalyst preparation comprising one or more enzymes isolated from said organism. The process involves: 1) contacting said organism or biocatalyst preparation obtained therefrom with a fossil fuel that contains organic sulfur, such that a mixture is formed; and 2) incubating the mixture for a sufficient time for the biocatalyst expressed by or prepared from the organism to desulfurize the fossil fuel. The biocatalytically treated fossil fuel obtained following incubation has significantly reduced levels of organosulfur compounds, compared to a sample of the corresponding untreated fossil fuel.

In yet another aspect, the invention relates to nucleic acid probes which hybridize to the recombinant DNA of the present invention.

In still other aspects, the present invention relates to the production of new non-human organisms containing the recombinant DNA of the present invention and preferably expressing the biocatalyst encoded therein. Availability of the recombinant DNA of this invention greatly simplifies and facilitates the production and purification of biocatalysts for desulfurizing a fossil fuel. Costly and time consuming procedures involved in the purification of biocatalysts can be reduced, eliminating the need to generate the biocatalyst from one or more non-human organisms in which it is naturally present or has been produced by mutagenesis. More specifically, non-human host organisms can be generated which express the gene or genes of the present invention at elevated levels. In addition, the invention described herein furthers the discovery of genes encoding desulfurization biocatalysts in additional non-human organisms. This objective can be accomplished using the nucleic acid probes of the present invention to screen DNA libraries prepared from one or more additional non-human organisms in whom biocatalytic function is known or suspected to be present. Any genes present in such organisms and encoding desulfurization biocatalysts or components thereof can be replicated at large scale using known techniques, such as polymerase chain reaction (PCR). PCR advantageously eliminates the need to grow the non-human organisms, e.g., in culture, in order to obtain large amounts of the DNA of interest.

DETAILED DESCRIPTION OF THE PREFERRED EMBODIMENT

Figure 1:
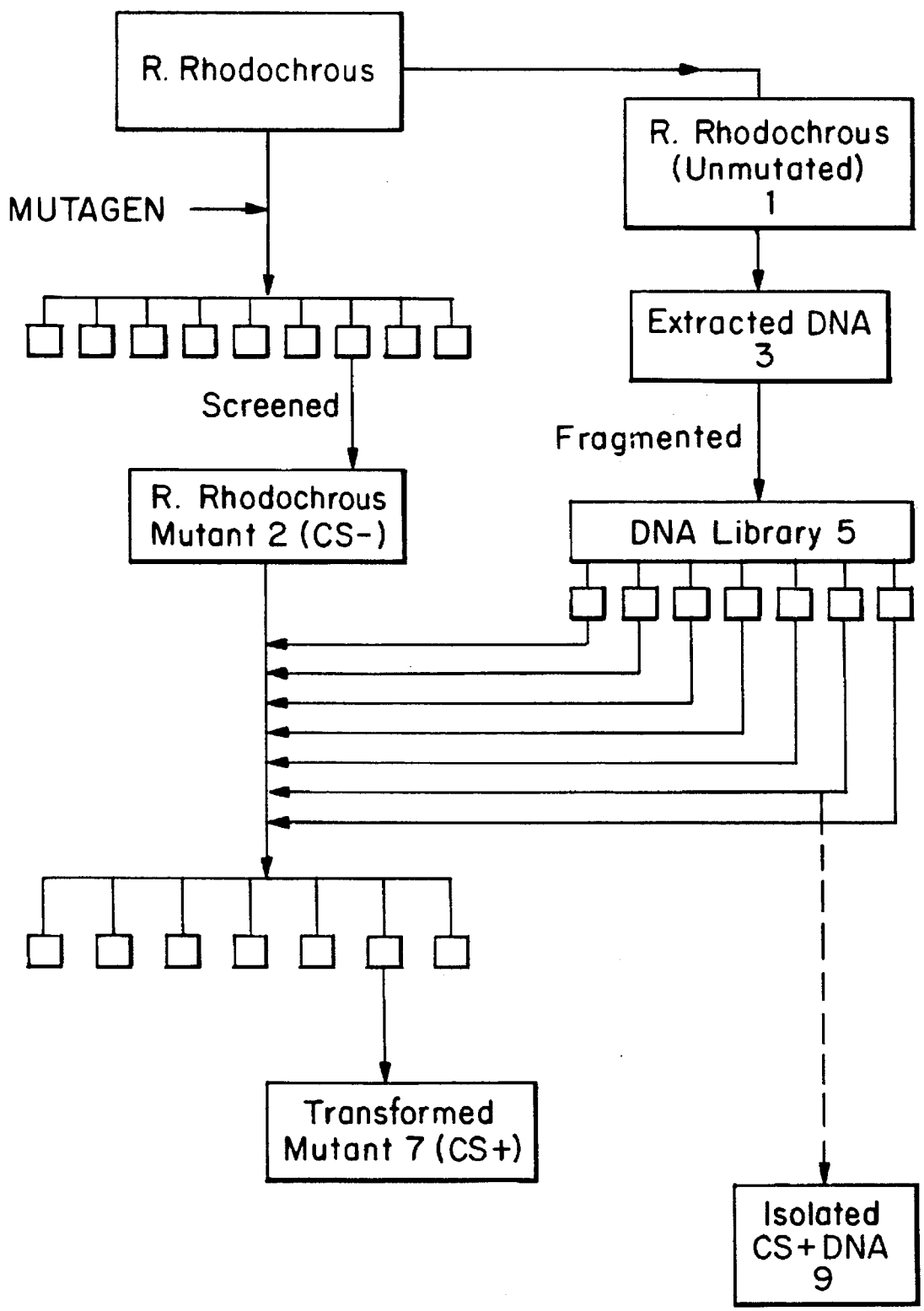
FIG. 1 is a flow diagram schematic illustrating a stepwise procedure for the isolation of the recombinant DNA of the present invention.

In the petroleum extraction and refining arts, the term "organic sulfur" is generally understood as referring to organic molecules having a hydrocarbon framework to which one or more sulfur atoms (called heteroatoms) are covalently joined. These sulfur atoms can be joined directly to the hydrocarbon framework, e.g., by one or more carbon-sulfur bonds, or can be present in a substituent joined to the hydrocarbon framework of the molecule, e.g., a sulfonyl group (which contains a carbon-oxygen-sulfur covalent linkage). The general class of organic molecules having one or more sulfur heteroatoms are sometimes referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked to adjacent carbon atoms in the hydrocarbon framework by aromatic carbon-sulfur bonds are referred to as "sulfur-bearing heterocycles". The sulfur that is present in many types of sulfur-bearing heterocycles is referred to as "thiophenic sulfur" in view of the five-membered aromatic ring in which the sulfur heteroatom is present. The simplest such sulfur-bearing heterocycle is thiophene, which has the composition $C_4H_4S$.

Sulfur-bearing heterocycles are known to be stable to conventional desulfurization treatments, such as HDS. For this reason, they are said to be refractory or recalcitrant to HDS treatment. Sulfur-bearing heterocycles can have relatively simple or relatively complex chemical structures. In complex heterocycles, multiple condensed aromatic rings, one or more of which can be heterocyclic, are present. The difficulty of desulfurization increases with the structural complexity of the molecule. Shih et al. That is, refractory behavior is most accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzylic rings. Much of the residual post-HDS organic sulfur in fossil fuel refining intermediates and combustible products is thiophenic sulfur. The majority of this residual thiophenic sulfur is present in DBT and derivatives thereof having one or more alkyl or aryl radicals attached to one or more carbon atoms present in one or both flanking benzylic rings. Such DBT derivatives are said to be "decorated" with these radicals. DBT itself is accepted in the relevant arts as a model compound illustrative of the behavior of the class of compounds encompassing DBT and alkyl- and/or aryl-decorated derivatives thereof in reactions involving thiophenic sulfur. Monticello and Finnerty (1985), Microbial desulfurization of fossil fuels, 39 *Annual Reviews in Microbiology* 371–389, at 372–373. DBT and radical-decorated derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom. Id. Another characteristic of DBT and radical-decorated derivatives thereof is that, following a release of fossil fuel into the environment, these sulfur-bearing heterocycles persist for long periods of time without significant biodegradation. Gundlach et al. (1983), 221 *Science* 122–129. Thus, most prevalent naturally occurring microorganisms do not effectively metabolize and break down sulfur-bearing heterocycles.

A fossil fuel that is suitable for desulfurization treatment according to the present invention is one that contains organic sulfur. Such a fossil fuel is referred to as a "substrate fossil fuel". Substrate fossil fuels that are rich in thiophenic sulfur (wherein a significant fraction of the total organic sulfur is thiophenic sulfur, present in sulfur-bearing heterocycles, e.g., DBT) are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization (biocatalysis or BDS) is the excision (liberation or removal) of sulfur from organosulfur compounds, including refractory organosulfur compounds such as sulfur-bearing heterocycles, as a result of the selective, oxidative cleavage of carbon-sulfur bonds in said compounds by a biocatalyst. BDS treatment yields the desulfurized combustible hydrocarbon framework of the former refractory organosulfur compound, along with inorganic sulfur—substances which can be readily separated from each other by known techniques such as fractional distillation or water extraction. For example, DBT is converted into hydroxybiphenyl or dihydroxybiphenyl, or a mixture thereof, when subjected to BDS treatment. BDS is carried out by a biocatalyst comprising one or more non-human organisms (e.g., microorganisms) that functionally express one or more enzymes that direct, singly or in concert with each other, the removal of sulfur from organosulfur compounds, including sulfur-bearing heterocycles, by the selective cleavage of carbon-sulfur bonds in said compounds; one or more enzymes obtained from such microorganisms; or a mixture of such microorganisms and enzymes. Organisms that exhibit biocatalytic activity are referred to herein as being CS+ or Dsz+. Organisms that lack biocatalytic activity are referred to herein as being CS– or Dsz–.

As summarized above, the invention described herein relates in one aspect to a DNA molecule or fragment thereof containing a gene or genes which encode a biocatalyst capable of desulfurizing a fossil fuel that contains organosulfur compounds. The present DNA molecule or fragment thereof can be purified and isolated DNA obtained from, e.g., a natural source, or can be recombinant (heterologous or foreign) DNA that is, e.g., present in a non-human host organism. The following discussion, which is not to be construed as limiting on the invention in any way but is presented for purposes of illustration, recounts the isolation of DNA encoding a desulfurizing biocatalyst from a strain of Rhodococcus Sp., ATCC No. 53968, that is known to express suitable biocatalytic activity. This preferred strain of Rhodococcus is disclosed in U.S. Pat. No. 5,104,801 (issued 1992), the teachings of which are incorporated herein by reference, and has been referred to in the literature as IGTS8. IGTS8 was developed by investigators at the Institute of Gas Technology in Chicago Ill. Other organisms that are known to express suitable biocatalytic activity and thus are viewed as suitable sources of the DNA of the present invention include the strain of Bacillus sphaericus described in U.S. Pat. No. 5,002,888 and deposited with the American Type Culture Collection as ATCC No. 53969 and the Corynebacterium strain described in Omori et al. (1992), Desulfurization of dibenzothiophene by Corynebacterium sp. strain SY1, 58 *Appl. Env. Microbiol.* (No. 3) 911–915. The isolation of the DNA of the present invention from the ATCC No. 53968 microorganism is schematically depicted in FIG. 1, and will now be described.

Mutant strains of Rhodococcus that are incapable of cleaving carbon-sulfur bonds (CS– or Dsz–), are produced by exposing a strain of *R. rhodochrous*, e.g., ATCC No. 53968, that exhibits biocatalytic activity (that is CS+ or Dsz+), to a mutagen under appropriate conditions that are known to or readily ascertainable by those skilled in the art. Suitable mutagens include radiation, e.g., ultraviolet radiation, and chemical mutagens, e.g., N-methyl-N'-nitrosoguanidine (NTG), hydroxylamine, ethylmethanesulphonate (EMS) and nitrous acid. Mutants thus formed are allowed to grow in an appropriate medium and screened for carbon-sulfur bond cleavage activity. Mutants identified as lacking carbon-sulfur bond cleavage activity are termed CS–. Any method of screening which allows for an accurate detection of carbon-sulfur bond cleavage activity is suitable in the method of the present invention. Suitable methods of screening for this activity include exposing the different mutants to carbon-sulfur bond containing molecules (e.g., DBT) and measuring carbon-sulfur bond cleavage. In a preferred embodiment, the mutants are exposed to DBT, such that the breakdown product, hydroxybiphenyl (HBP), which fluoresces under short wave ultraviolet light, is produced. HBP can also be detected colorimetrically through its blue reaction product with Gibbs' reagent. Other methods include gas and liquid chromatography, infrared and nuclear magnetic resonance spectrometry. See Kodama, et al., Applied and Environmental Microbiology, pages 911–915 (1992) and Kilbane and Bielaga, Final Report D.O.E. Contract No. DE-AC22-88PC8891 (1991). Once CS– mutants are identified and isolated, clones thereof are propagated using standard techniques and subjected to further analysis.

Concurrent with the mutagenesis of the above-described culture of the CS+ organism, *R. rhodochrous*, a second culture of the same CS+ organism (1) is maintained in culture. CS+ organism DNA (3) is extracted from this culture of *R. rhodochrous*. Various methods of DNA extraction are suitable for isolating the DNA of this organism. Suitable methods include phenol and chloroform extraction. See Maniatis et al., *Molecular Cloning, A Laboratory Manual*, 2d, Cold Spring Harbor Laboratory Press, page 16.54 (1989), herein referred to as Maniatis et al.

Once the DNA is extracted from *R. rhodochrous* 1, the DNA (3) is cut into fragments of various kilobase lengths, which collectively make up DNA library 5. Various methods of fragmenting the DNA of *R. rhodochrous* to purify DNA therefrom, including the DNA of the present invention, can be used, e.g., enzymatic and mechanical methods. Any four-base recognition restriction endonuclease such as TaqI or Sau 3A is suitable for fragmenting the DNA. Suitable methods of fragmenting DNA can be found in Maniatis et al.

The various DNA fragments are inserted into several CS– mutant clones of *R. rhodochrous* (2), with the purpose of isolating the fragment of DNA that encodes the biocatalyst of the present invention. The transformation of a previously CS– mutant cell to a Cs+ transformed cell is evidence that the inserted DNA fragment encodes a biocatalyst. Any method of inserting DNA into *R. rhodochrous* which allows for the uptake and expression of said fragment is suitable. In a preferred embodiment, electroporation is used to introduce the DNA fragment into *R. rhodochrous*. See Maniatis et al.

Once transformed, CS+ mutant *R. rhodochrous* 7 has been produced and identified, DNA fragment 9 encoding the CS+ biocatalyst can be identified and isolated. The encoded biocatalyst can then be produced using the isolated DNA in various methods that are well known and readily available to those skilled in the art. In addition, the isolated DNA can be sequenced and replicated by known techniques, e.g., the techniques described in Maniatis et al.

As noted previously, the above-described method for isolating the DNA of the present invention can be applied to CS+ organisms other than *R. rhodochrous* microorganisms, e.g., of the strain ATCC No. 53968. Thus, *Bacillus sphaericus* ATCC No. 53969 or Corynebacterium sp. SY1 can be used as the source organism for the DNA of the present invention. Furthermore, once isolated, the DNA of the present invention can be transfected into a non-human host organism other than a CS– mutant of the source organism. Thus, the DNA of the present invention can be transfected into, e.g., a suitable strain of *Escherichia coli* bacteria. Other types of non-human host organism can also be used, including unicellular organisms (e.g., yeast) and cells established in culture from multicellular organisms.

Other methods of isolating the DNA of the present invention, include variations on the rationale described above and depicted in FIG. 1. For example, it would be possible to randomly insert a CS– DNA plasmid into clones of a CS+ strain of *R. rhodochrous*. DNA encoding a CS+ biocatalyst could then be identified by screening for clones that have been transformed from CS+ to CS–.

The recombinant DNA molecule or fragment thereof of the present invention is intended to encompass any DNA resulting from the insertion into its chain, by chemical or biological means, of one or more genes encoding a biocatalyst capable of selectively cleaving carbon-sulfur bonds, said gene not originally present in that chain. Recombinant DNA includes any DNA created by procedures using restriction nucleases, nucleic acid hybridization, DNA cloning, DNA sequencing or any combination of the preceding. Methods of construction can be found in Maniatis et al., and in other methods known by those skilled in the art.

Procedures for the construction of the DNA plasmids or vectors of the present invention include those described in Maniatis et al. and other methods known by those skilled in the art. Suitable plasmid vectors include pRF-29 and pRR-6 depicted in FIGS. 2 and 3, respectively. The terms "DNA plasmid" and "vector" are intended to encompass any replication competent plasmid or vector capable of having foreign or exogenous DNA inserted into it by chemical or biological means and subsequently, when transfected into an appropriate non-human host organism, of expressing the product of the foreign or exogenous DNA insert (i.e., of expressing the biocatalyst of the present invention). In addition, the plasmid or vector must be receptive to the insertion of a DNA molecule or fragment thereof containing the gene or genes of the present invention, said gene or genes encoding a biocatalyst that selectively cleaves carbon-sulfur bonds in organosulfur compounds. Procedures for the construction of DNA plasmid vectors include those described in Maniatis et al. and others known by those skilled in the art.

The plasmids of the present invention include any DNA fragment containing a gene or genes encoding a biocatalyst that selectively cleaves carbon-sulfur bonds in organo-sulfur compounds. The term "plasmid" is intended to encompass any DNA fragment. The DNA fragment should be transmittable to a host microorganism by transformation or conjugation. Procedures for the construction or extraction of DNA plasmids include those described in Maniatis et al. and others known by those skilled in the art.

The transformed non-human host organisms of the present invention can be created by various methods by those skilled in the art. For example, transfection electroporation as explained by Maniatis et al. can be used. By the term "non-human host organism" is intended any non-human organism capable of the uptake and expression of foreign, exogenous or recombinant DNA, i.e., DNA not originally a part of the organism's nuclear material.

The method of desulfurizing a fossil fuel of the present invention involves two aspects. First, a host organism or biocatalytic preparation obtained therefrom is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon-sulfur bonds in organo-sulfur compounds, thereby producing a desulfurized fossil fuel. In one embodiment, an aqueous emulsion is produced with an aqueous culture of the organism and the fossil fuel, allowing the organism to propagate in the emulsion while the expressed biocatalyst cleaves carbon-sulfur bonds.

Variables such as temperature, mixing rate and rate of desulfurization will vary according to the organism used. The parameters can be determined through no more than routine experimentation.

Several suitable techniques for monitoring the rate and extent of desulfurization are well-known and readily available to those skilled in the art. Baseline and timecourse samples can be collected from the incubation mixture, and prepared for a determination of the residual organic sulfur in the fossil fuel. The disappearance of sulfur from organo-sulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

The nucleic acid probes of the present invention include any nuclear material capable of hybridizing to at least a portion of the DNA of the present invention. The term "nucleic acid probe" includes any nuclear material capable of hybridizing to DNA.

The invention will now be further illustrated by the following specific Examples, which are not to be viewed as limiting in any way.

EXAMPLE 1.

Isolation of DNA Encoding a Desulfurization Active Biocatalyst

As used herein, the term "Dsz+" refers to the ability of an organism to utilize thiophenic compounds such as dibenzothiophene (DBT) as the sole source of sulfur by the selective cleavage of carbon-sulfur bonds therein. Rhodococcus strain IGTS8 demonstrates the Dsz+ phenotype. The term "Dsz–" refers to an organism's inability to utilize said thiophenic compounds as a sole source of sulfur by the selective cleavage of carbon-sulfur bonds therein.

Materials

Figure 2:
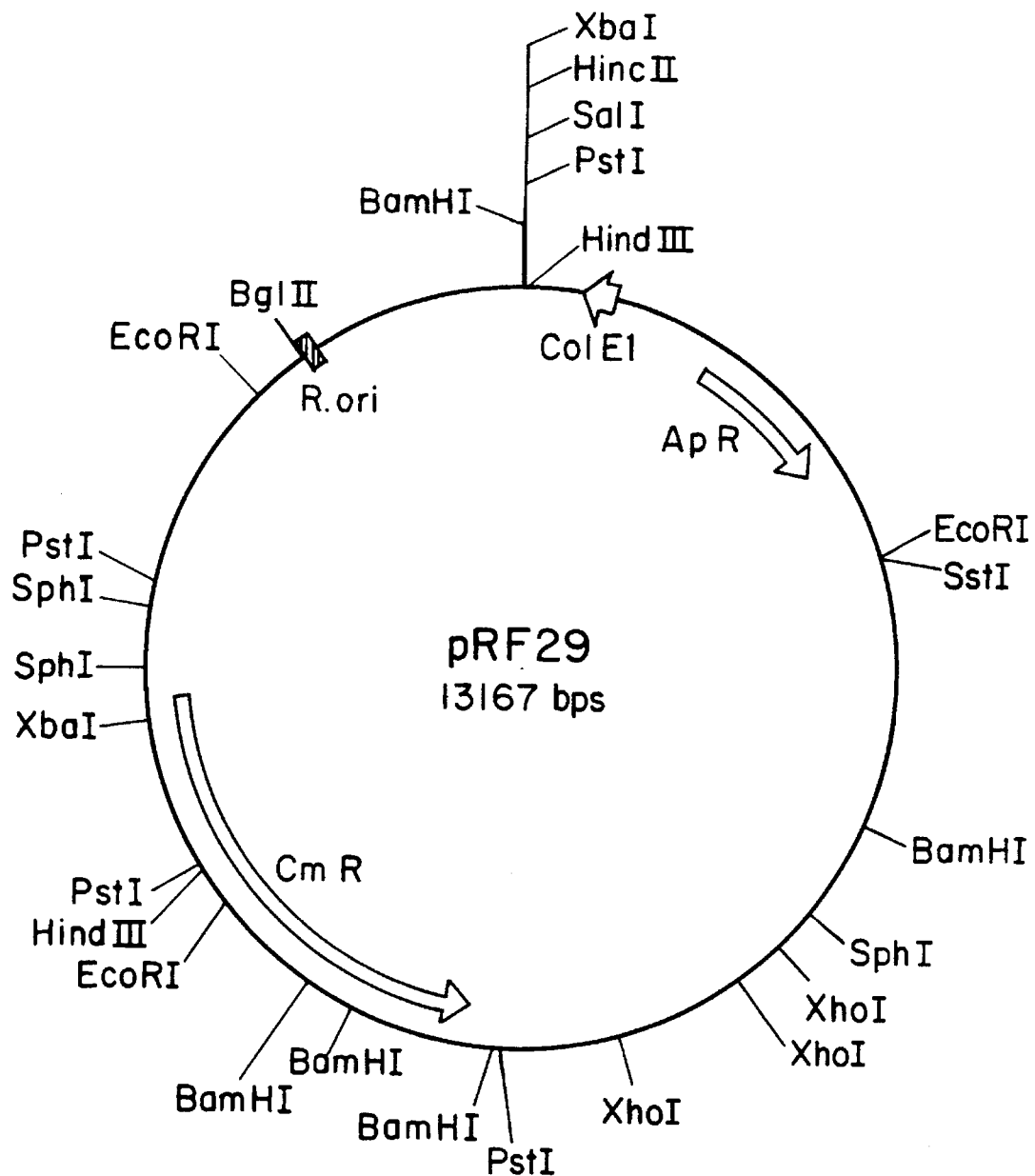
FIG. 2 is a schematic illustration of the *Rhodococcus rhodochrous* replication competent and chloramphenicol resistant vector pRF29, said vector having been derived from *Rhodococcus fascians*.
Figure 3:
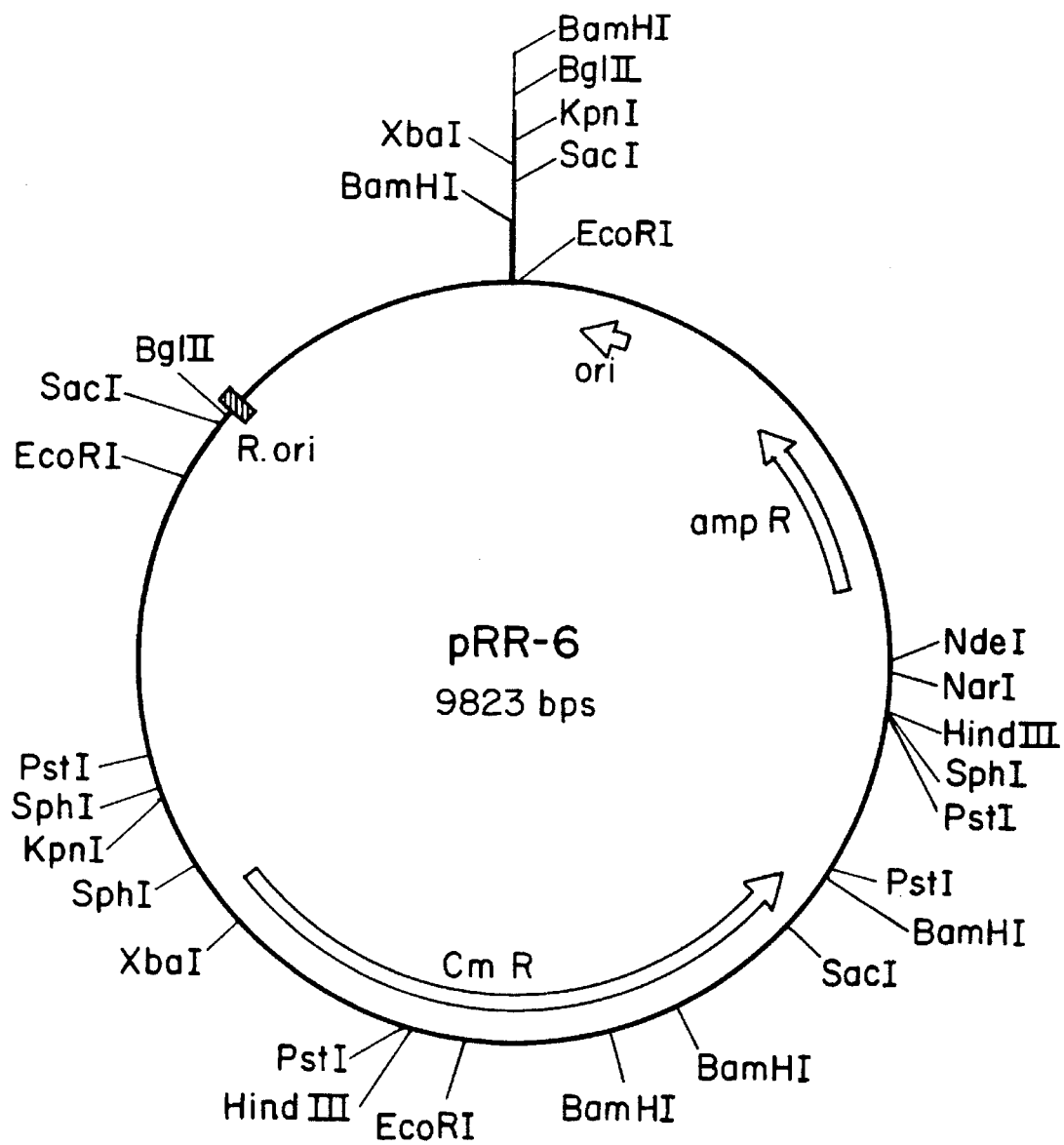
FIG. 3 is a schematic illustration of the *Rhodococcus rhodochrous* replication competent and chloramphenicol resistant vector pRR-6.

Bacterial strains and plasmids
Rhodococcus strain IGTS8 (ATCC No. 53968), obtained from the Institute of Gas Technology (Chicago, Ill.), was used as a parent strain for production of mutant strains which have lost the desulfurization phenotype (Dsz–). Strain IGTS8 was also used for isolation of DNA fragments capable of complementing said mutants to produce Dsz+ mutants therefrom. Rhodococcus vector pRF-29 was obtained from the Institute of Gas Technology. The construction of pRF-29 is described in Desomer, et al. (1990), Transformation of Rhodococcus fascians by High-Voltage Electroporation and Development of *R. fascians* Cloning Vectors, *Applied and Environmental Microbiology* 2818–2825. The structure of pRF-29 is schematically depicted in FIG. 2.

*Escherichia coli* strain JM109 was used as a host in transformation with plasmid constructs derived from the plasmids pUC18 and pUC19 (Bethesda Research Laboratories, Bethesda, Md.).

Enzymes and Reagents
Restriction endonucleases were purchased from Bethesda Research Laboratories (BRL) and New England Biolabs (Beverly, Mass.). T4 ligase and the Klenow fragment of *E. coli* DNA polymerase I were purchased from BRL. HK™ Phosphatase was purchased from Epicentre Technologies (Madison, Wis.). All enzymes were used in accordance with manufacturers recommendations. Enzyme assay substrates Dibenzothiophene (DBT), Dibenzothiophene 5-oxide (DBT sulfoxide) and Dibenzothiphene sulfone (DBT sulfone) were purchased from Aldrich (Milwaukee, Wis.). Gibb's Reagent, 2,6-dicholoroquinone-4-chloroimide, was purchased from Sigma (St. Louis, Mo.). Chemical mutagen N-methyl-N'-nitro-N-nitrosoguanidine (NTG) was also purchased from Sigma.

Growth Media and Conditions
*E. coli* JM109 was grown in L-broth (Difco, Detroit, Mich.). Transformants were selected on L-plates supplemented with 1.5% agar and containing 125 µg/ml ampicillin. *E. coli* strains were grown at 37° C. Rhodococcus strains were maintained on Rhodococcus Media (RM) composed per liter of: 8.0 g Nutrient Broth (Difco), 0.5 g yeast extract, 10.0 g glucose. Transformants of Rhodococcus strains were selected on RM plates supplemented with 1.5% agar and containing 25 µg/ml chloramphenicol. For expression of the Dsz+ phenotype, Rhodococcus strains were grown in Basal Salts Media (BSM) composed per liter of: 2.44 g $KH_2PO_4$, 5.57 g $Na_2HPO_4$ 2.0 g $NH_4Cl$, 0.2 g $MgCl_2.6H_2O$, 0.001 g $CaCl_2.2H_2O$, 0.001 g $FeCl_3.6H_2O$, 0.004 g $MnCl_2.4H_2O$, 6.4 ml glycerol. Optionally, BSM can be supplemented with 5.0 g/liter glucose. Rhodococcus strains were grown at 30° C.

Methods

Sulfur Bioavailability Assay
The sulfur bioavailability assay, described in U.S. Pat. No. 5,104,801, examines an organism's ability to liberate organically bound sulfur from substrates (e.g., DBT, DBT sulfoxide, DBT sulfone) for use as the sole source of sulfur for growth. In the assay, BSM, which contains no sulfur, is supplemented with one or more sulfur containing substrates, e.g., DBT. The organism's ability to liberate sulfur therefrom is measured by its ability to grow with proper incubation, as monitored by optical density at 600 nm.

Gibbs Assay for 2-Hydroxybiphenyl
The oxidative product of DBT, DBT sulfoxide and DBT sulfone incubated with strain IGTS8 is 2-hydroxybiphenyl (2-HBP). The Gibbs assay colorimetrically quantitates the amount of 2-HBP produced from DBT and its above-mentioned oxidative derivatives. The assay measures 2-HBP produced in culture supernatants after incubation with DBT. The media must be adjusted to pH 8.0 before the Gibb's reagent is added. Gibb's Reagent, 2,6-dicholoroquinone-4- chloroimide (10 mg/ml in ethanol), is added to culture supernatants at 1:100 (v/v). Color development is measured as absorbance at 610nm after a 30 minute incubation at room temperature.

HPLC Assay for 2-Hydroxybiphenyl

2-HBP production cultures incubated with DBT can also be detected by HPLC using instrumentation available from Waters, Millipore Corporation, Milford, Mass. Reagent alcohol is added to culture broth at 1:1 (v/v) in order to solubilize all remaining DBT and 2-HBP. Samples are agitated for 5 min at 220 rpm. Extracted broth samples are removed and centrifuged to remove cellular mass. Clarified supernatants are then analyzed by HPLC with the following conditions:

| Column: | Waters 4µ Phenyl Novapak | |
|---|---|---|
| Detection Parameters: | DBT | 233 nm, 1.0 AUFS |
| | 2-HBP | 248 nm, 0.2 AUFS |
| Quantitative Detection Limits: | DBT | 10–250 µM |
| | 2-HBP | 6–60 µM |
| Mobile Phase: | Isocratic 70% Acetonitrile 1.5 ml/min | |
| Retention times: | DBT | 4.5 minutes |
| | 2-HBP | 2.9 minutes |

IGTS8 Mutagenesis

In order to generate mutant strains of *R. rhodochrous* which did not metabolize DBT (Dsz– mutants), biocatalyst source strain IGTS8 (Dsz+) was subjected to mutagenesis by short-wave UV light and to chemical mutagenesis with N-methyl-N'-nitro-N-nitrosoguanidine (NTG). With UV exposure mutagenesis, a kill rate of greater than 99% was targeted. Continuously stirred *R. rhodochrous* cells at an optical density ($A_{660}$) of 0.3 were subjected to UV exposure from a Mineralight Lamp Model UVG-254 (Ultra-violet Products, Inc., San Gabriel, Calif.) at a distance of 10 cm for 55 to 65 seconds to obtain this kill rate (97.9–99.9%). For NTG mutagenesis, cell suspensions were treated with 500 µg/ml NTG for a duration determined to achieve a kill rate of 30%–50%. Combination mutagenesis utilizing both NTG and UV was also done. For these an overall kill rate of greater than 99.9% was used. Colonies surviving mutagenesis were picked onto RM plates and screened for the Dsz– phenotype as described below.

Screening Example A: Initially, a DBT-spray plate screen was used to select Dsz– mutants. Mutant colonies were replica plated onto Basal Salts Media (BSM) electrophoretic-grade agarose plates which contained no added sulfur. Colonies were allowed to grow at 30° C. for 24hr. The plates were then sprayed with an even coating of 10% DBT dissolved in ether and incubated at 30° C. for 90 minutes. The plates were then wiped clean and observed under short-wave UV light. The observed end product of DBT metabolism, 2-hydroxybiphenyl (2-HBP) fluoresces under short-wave UV light. Colonies that produce 2-HBP are thus identified by fluorescent spots on the agarose. Colonies that do not produce 2-HBP (that are Dsz–) do not produce fluorescent spots.

Screening Example B: A simpler variation of screening involved replica plating surviving mutagenized colonies to BSM agarose plates supplemented with 1.2 ml/liter of a saturated ethanol solution of DBT. After 24 hours, production of 2-HBP can be visualized under UV illumination as above.

Mutants which did not appear to produce 2-HBP by the above-described screening methods were examined with the sulfur bioavailability assay, with DBT as the sole source of sulfur. Growth of potential mutants was examined in 1.25 ml liquid fermentations in BSM plus DBT media dispensed in 24-well plates (Falcon). After a one day incubation at 30° C., 2-HBP production was monitored by the Gibbs colorimetric assay. Strains which continue to demonstrate the Dsz– phenotype were incubated in larger volumes of BSM plus DBT and analyzed for 2-HBP or intermediates by the HPLC method. Because BSM is a defined minimal medium, a duplicate control culture which contained supplemental inorganic sulfur was grown in order to distinguish true Dsz– mutants from auxotrophic mutants. Mutants which failed to grow in both the control and experimental media were assumed to be auxotrophic mutants.

Of 1970 individually analyzed potential mutants, two were identified as Dsz–. One, mutant, GPE-362, was generated by NTG mutagenesis. The other, CPE-648, was generated by combination NTG/UV mutagenesis. Both GPE-362 and CPE-648 grow slowly in sulfur bioavailability assays, presumably from trace amounts of sulfur on the glassware or in the media components. However, no detectable amounts of 2-HBP were produced by either mutant after an extended incubation of 6 to 10 days with DBT, as assessed with either the Gibbs assay or the HPLC assay. Thus, independently produced Rhodococcus IGTS8 mutants GPE-362 and CPE-648 were Dsz– organisms.

Vector Construction

Vector constructs were derived from Rhodococcus and confer chloramphenicol resistance. All constructs were developed in *E. coli* strain JM109. Transformation of JM109 was carried out with the Gene Pulsar (Bio-Rad Laboratories, Richmond, Calif.) according to manufacturer's recommendations. Plasmid isolation from JM109 was performed by standard methods (Birnboim and Doly (1979), A rapid alkaline extraction procedure for screening recombinant plasmid DNA, 7 *Nucleic Acids Res.* 1513–1523; Maniatis et al. (1982), *Molecular Cloning: A Laboratory Manual* (Cold Spring Harbor Laboratory Press). Transformants containing correct vector constructs were identified by restriction analysis.

Vector Construct A: pRR-6 (FIG. 3) contains the Rhodococcus origin of replication and Chloramphenicol resistance marker ($Cm^R$). The ori and $Cm^R$ have been removed from pRF-29 as a 6.9 kb XhoI/Xba (partial) fragment. The ends were made blunt with Klenow and ligated to SalI/XbaI cut pKF39. pKF39 is pUC18 with the SmaI site replaced with a BglII site. A unique NarI site is available for cloning in pRR-6. NarI ends are compatible with 4-base recognition endonuclease TaqI.

Transformation of Rhodococcus

Transformation of IGTS8 and Dsz– mutants thereof can be achieved by electroporation. The following conditions were used in all transformations of Rhodococcus. Cells were grown in RM to mid-log phase and harvested by centrifugation (5000×g), then washed three times in cold, deionized, distilled water and concentrated 50-fold in 10% glycerol. The resulting cell concentrate could be used for electroporation directly or stored at −80° C.

Electroporations were carried out with the Gene Pulser (Bio-Rad) apparatus. 100 µl cells were mixed with transformation DNA in a 2-mm gapped electrocuvette (Bio-Rad) and subjected to a 2.5 kV pulse via the pulse controller (25 µF capacitor, 200 Ω external resistance). Pulsed cells were mixed with 400µ RM and incubated for 4 hours at 30° C. with regular agitation. Cells were then plated to RM supplemented with proper antibiotic.

When IGTS8 was transformed with pRF-29, chloramphenicol resistant colonies were cleanly selected at a frequency of $10^5$–$10^6$/µg DNA on plates containing 25 µg/ml chloramphenicol.

Small Scale Plasmid Preparation from Rhodococcus

A single colony of Rhodococcus was used to inoculate 2 to 7 ml of RM plus 25 µg/ml chloramphenicol. The culture was incubated for two days at 30° C. with shaking. Cells were pelleted by centrifugation and resuspended in 300 µl sucrose buffer (20% sucrose, 0.05M Tris-Cl pH 8.0, 0.01M EDTA 0.05M NaCl, 10 mg/ml lysozyme) and incubated at 37° C. for 1 hour. 300 µl Potassium acetate-acetate solution, pH 4.8 (60 ml 5M KOAc, 11.5 ml Glacial acetic acid, 28.5 ml dH$_2$O), was added and the mixture was gently mixed by inversion. The mixture was placed on ice for 5 minutes and then cellular debris was pelleted by centrifugation. 500 µl supernatant was removed to a fresh tube to which RNAse was added, to 0.05 µg/µl and incubated for 20 minutes at 37° C. The sample was then phenol:-chloroform extracted and the aqueous layer was precipitated at −80° C. with an equal volume of isopropanol. DNA was pelleted by centrifugation and resuspended in 0.3M NaOAc pH 8.0. DNA was precipitated again at −80° C. with an equal volume of isopropanol. DNA was pelleted by centrifugation and resuspended in 0.3M NaOAc pH 8.0. DNA was precipitated again at −80° C. with two volumes of 95% EtOH. Pelleted DNA was washed with 70% EtOH and resuspended in 50 µl TE (Tris EDTA).

Isolation of Genomic DNA from Rhodococcus Strain IGTS8

IGTS8 genomic DNA was isolated as described. 20 ml RM was inoculated with a single colony of IGTS8 and incubated at 30° C. for 48 hours with shaking at 220 rpm. Cells were harvested by centrifugation (5000×g). Cells were resuspended in 10 ml TE (10 mM Tris Base, 1 mM EDTA) with 100 mg lysozyme and incubated for 30 minutes at 30° C. Cells were lysed by adding 1 ml of 20% sodium dodecyl sulfate (SDS). 10 ml of TE-saturated phenol and 1.5 ml 5 M NaCl were added immediately and the mixture was gently agitated for 20 minutes at room temperature. Phenol was removed by centrifugation, and the aqueous layer was extracted twice with an equal volume of chloroform. An equal volume of isopropanol was added to the aqueous layer to precipitate the DNA. DNA was spooled onto a pasteur pipette and redissolved in TE. DNA was then RNased with 20 µg/ml RNA for 1 hour at 37° C. The sample was made to a final concentration of 100 mM NaCl and 0.4% SDS and proteased with 100 µg/ml protease K. The sample was then extracted with phenol and chloroform and precipitated with isopropanol as before. The purified genomic DNA, which included the DNA of the present invention, was resuspended in TE.

Construction of Plasmid Library of IGTS8

Genomic DNA from the Dsz+ source organism (IGTS8) was cut with TaqI in order to produce fragments 0.5–23 kb in length. Cut DNA was electrophoresed through 0.8% low melting temperature agarose and DNA fragments greater than 5 kb in length were isolated and purified by standard methods (Maniatis, T. et al. (1982), *Molecular Cloning: A Laboratory Manual* (Cold Spring Harbor Laboratory Press)). Vector pRR-6 was cut with NarI to completion. The vector ends were dephosphorylated with HK™ phosphatase to prevent religation of the vector. The size-fractioning genomic DNA was ligated to cut and dephosphorylated pRR-6.

Molecular Complementation of Dsz− Mutant Strain CPE-648

Plasmid library ligations (above) were used to transform Dsz− mutant strain CPE-648 by electroporation as described. Negative control transformations of CPE-648, which did not contain DNA (mock transformations), were also performed. After the four hour incubation in RM, the cells were spun out of suspension by centrifugation and the supernatant was removed. The cells were resuspended in BSM with no sulfur. These cells were used to inoculate 250 ml of BSM supplemented with 300 µl of a saturated ethanol solution of DBT. By this procedure, clones which are capable of complementing the Dsz− mutation will be selected by the sulfur bioavailability assay. Strains containing the complementing sequences (i.e., the DNA of the present invention) will successfully remove the sulfur from DBT and grow preferentially.

After 6 days incubation at 30° C., the cultures were assayed for 2-HBP by HPLC. Accumulation of 2-HBP was detected in experimental cultures while no accumulation of 2-HBP was detected in control cultures. The culture producing 2-HBP was spread onto RM plates supplemented with chloramphenicol to obtain single colonies that were harboring plasmids. These plates were replica-plated to BSM agarose plates supplemented with 1.2 ml/liter of a saturated ethanol solution of DBT. After 24 hours incubation at 30° C., 2-HBP could be detected around some individual colonies under short wave UV illumination. These colonies presumably harbored plasmids which complemented the Dsz− mutant by restoring the former Dsz+ phenotype.

Characterization of Clones Complementing Dsz− Mutant CPE-648

Two independent plasmid libraries successfully complemented mutant CPE-648 to Dsz+ as described above.

Figure 4:
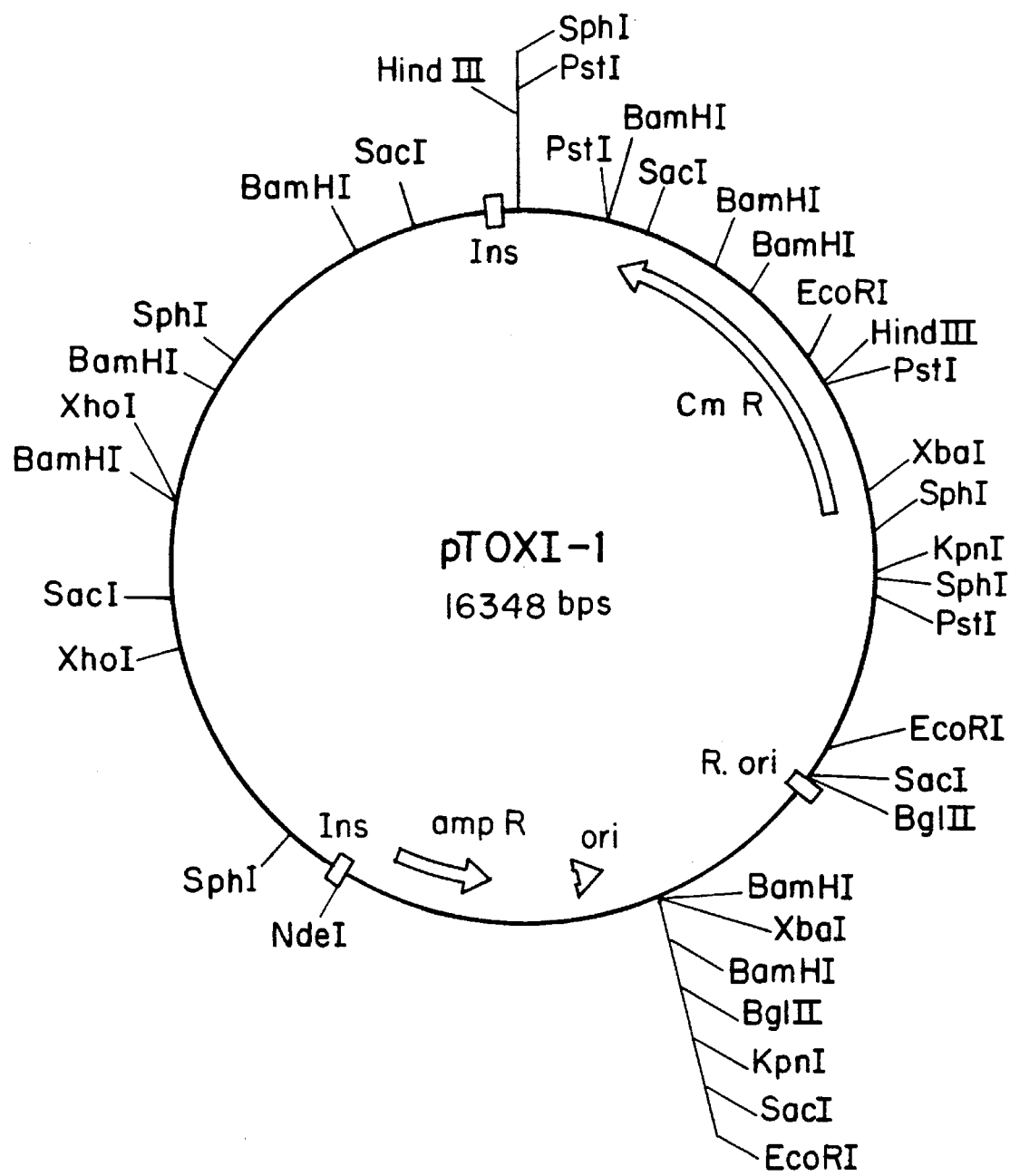
FIG. 4 is a schematic illustration of the restriction map for DNA plasmid pTOXI-1 encoding a biocatalyst capable of carbon-sulfur bond cleavage.

Plasmid DNA was isolated from single colonies which demonstrated 2-HBP production on BSM plus DBT plates (above) from cultures transformed with each of the two libraries. This plasmid DNA was used to transform *E. coli* strain JM109. Plasmid DNA was isolated and cut with restriction endonucleases in order to build a restriction map of the clones. Each of the two libraries yielded a single complementing clone. By restriction pattern similarities, the two clones appear to have overlapping sequences. These clones have been designated pTOXI-1 (FIG. 4) and pTOXI-2, respectively. pTOXI-1 contains an insert of approximately 6.6 kb. pTOXI-2 contains an insert of approximately 16.8 kb.

Complementation of Dsz− Mutant GPE-362

Dsz− mutant GPE-362 was transformed with plasmids pTOXI-1 and pTOXI-2. As a control, GPE-362 was also transformed with vector pRR-6. Transformants containing plasmid DNA were selected on RM plus chloramphenicol plates. $Cm^R$ colonies were transferred to BSM agarose plates supplemented with DBT. After 24 hr. incubation at 30° C., 2-HBP production could be seen around colonies containing either pTOXI-1 or pTOXI-2 by short wave UV illumination. No 2-HBP could be detected around colonies containing only vector pRR-6.

Overexpression of the $Dsz^+$ Trait Upon Reintroduction of Cloned DNA

Plasmids pTOXI-1 and pTOXI-2 were transformed into Dsz− mutant strain CPE-648. Transformants containing plasmid DNA were selected on RM plus chloramphenicol plates. The specific activity of individual clones was examined by the following protocol.

Single colonies of CPE-648 containing either pTOXI-1 or pTOXI-2 were used to inoculate 25 ml RM plus 25 µg/ml chloramphenicol in a 250 ml flask. As a positive control, parent strain IGTS8 was also grown in 25 ml RM. After 48 hours of growth at 30° C., 225 rpm shaking, 2.5 ml of the cultures were crossed into 25 ml BSM supplemented with 0.7 mM DMSO. Cultures were incubated for an additional 40 hours at 30° C. The optical density of each culture was measured at 600 nm against an appropriate blank. DBT was added to a final concentration of 150 µM and the cultures were incubated for 3 hours at 30° C. An equal volume of Reagent Alcohol (Baxter, McGaw Park, Ill.) was then added to each culture to solubilize any remaining DBT or 2-HBP. A 1 ml sample was removed and cellular debris removed by centrifugation. The supernatant was analyzed for 2-HBP by the HPLC assay described above. The specific activity is calculated as mg of 2-HBP per liter/hours of incubation/ $OD_{600}$. The results of the above assay is listed in Table 1.

TABLE 1

Biocatalytic Desulfurization Activity of Transformed Mutants

| STRAIN | $OD_{600}$ | 2-HBP (mg/l) | Specific Activity (mg/l/hr/$OD_{600}$) |
| --- | --- | --- | --- |
| IGTS8 | 2.89 | 3.94 | 0.45 |
| GPE-362 | 1.53 | 0.00 | 0.00 |
| CPE-648 | 4.10 | 0.00 | 0.00 |
| CPE648 (pTOXI-1) | 3.84 | 15.84 | 1.37 |
| CPE648 (pTOXI-2) | 2.88 | 5.74 | 0.66 |

EXAMPLE 2

DNA Sequencing of a Desulfurization Active Biocatalyst by the DiDeoxy Method from Plasmid pTOXI-1

Materials

Bacterial strains and plasmids

Plasmid pTOXI-1 was used as the original source of DNA for sequencing. *Escherichia coli* strain JM109 was used as a host for subcloning and plasmid maintenance. Plasmids pUC18 and pUC19 were purchased from Bethesda Research Laboratories (Bethesda, Md.).

Enzymes and Reagents

Restriction endonucleases were purchased from Bethesda Research Laboratories (BRL) and New England Biolabs (Beverly, Mass.). T4 ligase was purchased from BRL. A Sequenase Version 2.0 DNA sequencing kit was purchased from United States Biochemical Corporation (Cleveland, Ohio). All enzymes and kits were used in accordance with manufacturer's recommendations.

Growth Media and conditions

*E. coli* strain JM109 harboring plasmids was grown in L-broth (Difco) containing 100 µg/ml ampicillin. Transformants were selected on L-plates supplemented with 1.5% agar and containing 100 µg/ml ampicillin. *E. coli* strains were grown at 37° C.

Methods

Plasmid DNA preparation from *E. coli*

Plasmid DNA was prepared from *E. coli* via lysis by SDS (Maniatis, et al.). The DNA was further purified through a polyethylene glycol precipitation before use in sequencing reactions.

Plasmid Subcloning

Figure 5:
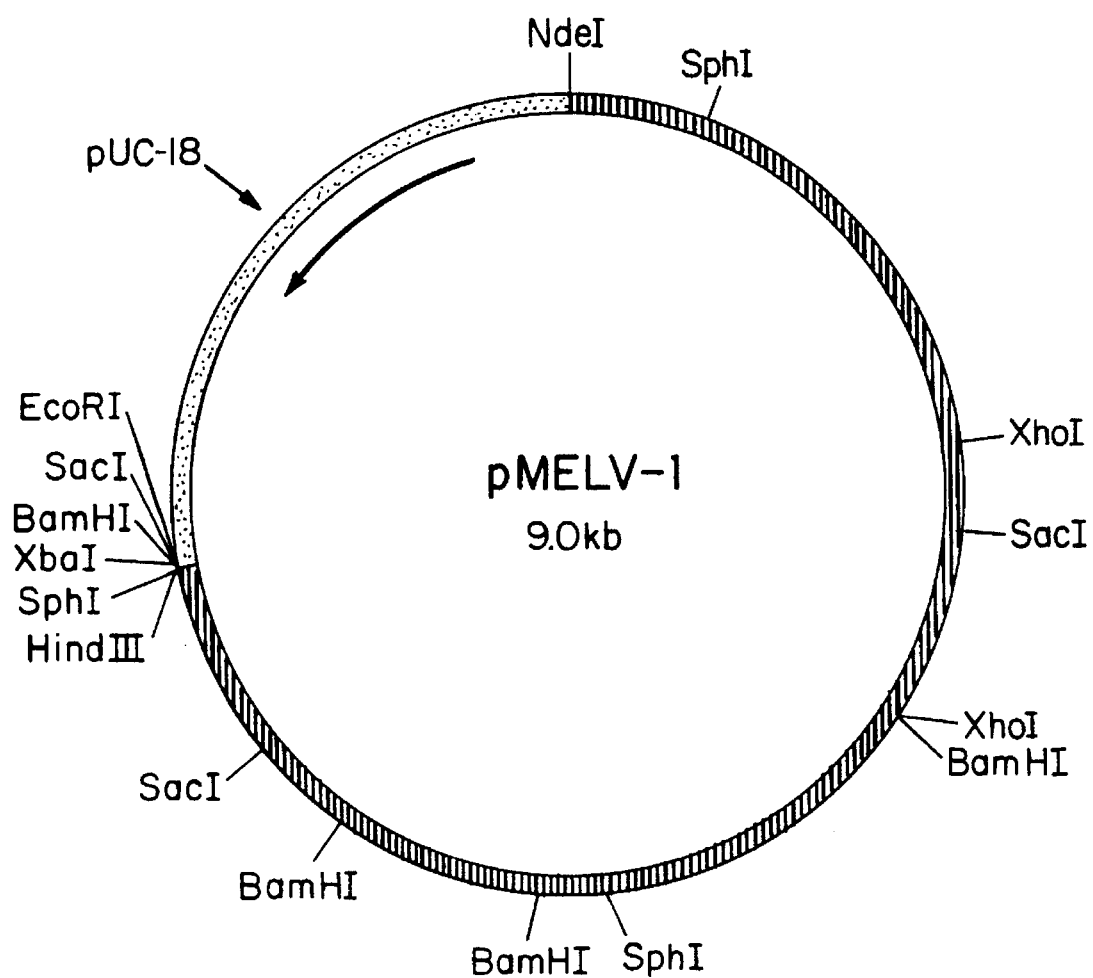
FIG. 5 is a schematic illustration of the restriction map for subclone pMELV-1, derived from plasmid pTOXI-1.
Figure 6:
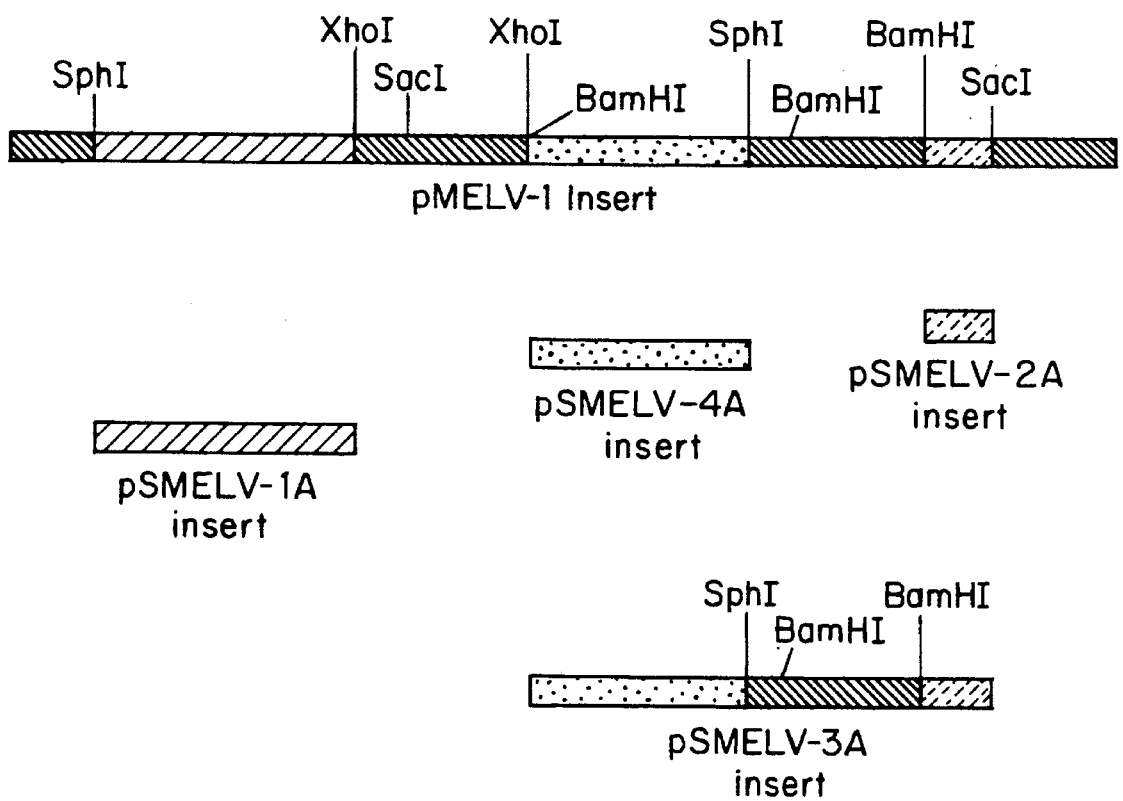
FIG. 6 is a schematic illustration of the restriction map for pMELV-1 and fragments thereof present as inserts in subclones pSMELV-1A, pSMELV-2A, pSMELV-3A and pSMELV-4A.

The following subclones of pTOXI-1 were generated by standard techniques to aid in DNA sequencing:

a) pMELV-1 (FIG. 5) was derived by isolating the 6.7 kb HindIII/NdeI fragment from pTOXI-1 (shown in FIG. 4) and ligating it to pUC-18 cut with HindIII/NdeI. JM109 cells harboring pMELV-1 were identified by plasmid isolation and restriction endonuclease analysis (Maniatis, et al.).

b) pSMELV-1A (FIG. 6) contains the 1.6 kb SphI/XhoI fragment of pMELV-1 subcloned into pUC-18.

c) pSMELV-2A (FIG. 6) contains the 0.7 kb BamHI/SacI fragment of pMELV-1 subcloned into pUC-18.

d) pSMELV-3A (FIG. 6) contains the 3.5 kb SacI/XhoI fragment of pMELV-1 subcloned into pUC-18.

e) pSMELV-4A (FIG. 6) contains the 1.5 kb SphI/BamHI fragment of pMELV-1 subcloned into pUC-18.

Dideoxy Sequencing from Plasmid DNA a) Denaturation. Prior to sequencing reactions, plasmid DNA must be denatured. This was accomplished by treatment with NaOH. The denatured DNA is then recovered by addition of salt and EtOH precipitation. Preferably, 2–5 µg of denatured plasmid DNA is used in each sequencing reaction. See manufacturer's recommendations with Sequenase Version 2.0 DNA sequencing kit (United States Biochemical Corporation).

b) Dideoxy sequencing. Chain termination dideoxy sequencing with Sequenase 2.0 was performed as described by the manufacturer (U.S. Biochemical Corporation). Sequencing of the cluster was initiated by priming subclones pMELV-1A, pMELV-2A, pMELV-3A, pMELV-4A with the "-40 Universal Primer" defined as:

5'-GTTTTCCCAGTCACGAC-3'(SEQ ID NO:6) and the "Reverse Primer" defined as: 5'-AACAGCTATGAC-CATG-3'(SEQ ID NO:7). The sequence was extended by synthesizing overlapping oligonucleotides to previously read sequence using the Gene Assembler Plus (Pharmacia, Piscataway, N.J.). The synthesized oligonucleotides were used as primers for continuing sequence reactions. Plasmid pMELV-1 was used as the template for all of the remaining sequences. DNA sequence was read from both strands of the plasmid clone to increase fidelity.

EXAMPLE 3

Complementation Cloning of a Desulfurization Active Biocatalyst from a Cosmid Library; Transfection of Biocatalyst DNA into an *R. fascians* Host Organism Materials and Methods Bacterial strains, media and reagents Rhodococcus sp. strain IGTS8, obtained from the Institute of Gas Technology (Chicago, Ill.) was used. UV1 is a mutant of IGTS8 that is unable to desulfurize DBT, described herein. *R. fascians* D188-5 (Desomer, et al., *J. Bacteriol.*, 170:2401–2405, 1988) and *R. rhodochrous* ATCC13808 (type strain from ATCC) do not metabolize DBT. *E. coli* XL1-Blue (from Stratagene Cloning System, La Jolla, Calif.) is recA1 lac thi endA1 gyrA96 hsdR17 supE44 relA1 [F' proAB lacI$^q$ lacZ$\Delta$M15 Tn10]. *E. coli* CS109 is W1485 thi supE F$^-$. *E. coli* S17-1 is a derivative of *E. coli* 294 and is recA thi pro hsdR$^-$ res$^-$ mod$^+$ [RP4-2-Tc::Mu-Km::Tn7] (Simon, et al., Plasmid vectors for the genetic analysis and manipulation of rhizobia and other gram-negative bacteria, p. 640–659. In A. Weissbach, and H. Weissbach (eds.), Methods in enzymology, vol 118, Academic Press, Inc., Orlando, 1986).

Pseudomonas minimal salts medium (PMS) was prepared according to Giurard and Snell (Biochemical factors in growth, p. 79–111. In P. Gerhardt, R. G. E. Murray, R. N. Costilow, E. W. Nester, W. A. Wood, N. R. Krieg, and G. B. Phillips (eds.), Manual of methods for general bacteriology, American Society for Microbiology, Washington, D.C., 1981) and contained 0.2% glycerol, 40 mM phosphate buffer (pH 6.8), 2% Hutner's mineral base, and 0.1% $(NH_4)_2SO_4$.

PMS medium lacking sulfate was prepared with chloride salts in place of sulfate salts. Luria broth (LB) was 1% bactotryptone, 0.5% yeast extract, and 1% NaCl. All liquid medium incubations were performed with shaking in water baths (New Brunswick Scientific, Edison, N.J.). Ampicillin (50 µg/ml) and tetracycline (12.5 µg/ml) were included as selective agents when required. Dibenzothiophene (DBT) was purchased from Fluka Chemical Corporation of Ronkonkoma, N.Y. DBT-sulfoxide was from ICN Biochemicals of Irvine, Calif., and DBT-sulfone was obtained from Aldrich Chemical Company of Milwaukee, Wis. Agarose was obtained from BRL.

Plasmid vectors pLAFR5 (Keen, et al., *Gene* 70:191–197, 1988) and pRF29 (Desomer, et al., 1988) served as sources of the Rhodococcus plasmid origin of replication.

Cosmid library construction

High molecular weight DNA was isolated from IGTS8 by the method of Consevage et al, (*J. Bacteriol.*, 162:138–146, 1985), except that cell lysis was accomplished in TE (10 mM Tris-HCl, 1 mM EDTA, pH 8.0) containing lysozyme (5 mg/ml) and SDS (2%). The DNA was partially digested with Sau3AI and fragments of approximately 20 kb were isolated after centrifugation through a sodium chloride gradient (Frischauf, et al,, *Digestion of DNA: size fractionation*, p. 183–189. In S. L. Berge, and A. R. Kimmel (eds.), Methods in Enzymology, vol 152, Academic Press, Inc, San Diego, Calif., 1987). These fragments were ligated into the BamHI site of pLAFR5 using standard procedures. In vitro packaging was performed using Gigapack Plus (Stratagene). Packaged cosmids were transduced into *E. coli* S17-1.

DBT spray plate assay

A spray plate assay for the identification of bacteria capable of modifying dibenzothiophene (DBT) was originally described by Kiyohara et al, (*Appl. Environ. Microbiol.*, 43:454–457, 1982) and modified by Krawiec (Bacterial desulfurization of thiophenes: screening techniques and some speculations regarding the biochemical and genetic bases, p. 103–114. In G. E. Pierce (ed.), Developments in Industrial Microbiology, vol 31, Society for Industrial Microbiology, Columbus, Ohio, 1990). The assay was further modified for use with IGTS8 as follows. Cells from individual IGTS8 colonies were transferred to LB plates as small (0.5 cm) patches and were incubated at 30° C. for 24 to 36 h. Large amounts of cells from these patches were transferred onto PMS-1% agarose plates that lacked a source of sulfur. These plates were immediately sprayed with a 0.1% DBT solution in ethyl ether. The PMS-DBT plates were incubated at 30° C. for a minimum of 18 hours and fluorescent products around the patches were detected by viewing under short-wave (254 nm) UV illumination.

Sulfur bioavailability assay

IGTS8 was incubated in PMS medium at 30° C. for 24 to 48 h, the cells were pelleted by centrifugation, followed by two washes with sulfur-free PMS. Washed cells were inoculated into PMS that contained, as a sole source of sulfur, a 0.2% concentration of one of the following: DBT, DBT-sulfoxide, or DBT-sulfone. The inoculum was adjusted so that the beginning absorbance at 600 nm ($A_{600}$) was 0.02. The culture was incubated at 30° C. and growth was monitored at $A_{600}$. For cultures incubated with DBT, the supernatant was viewed at various intervals under short wave UV light to check for production of fluorescent products. 800 ohms and were immediately diluted with 1 ml of LB containing 0.5M sucrose. The cells were incubated at 30° C. for 1 h, plated on LB agar plates plus appropriate antibiotics, and incubated at 30° C. until colonies developed. When the plasmid carried the pRF29 Rhodococcus plasmid origin of replication, colonies were visible after 48 h. In the absence of the pRF29 origin, colonies appeared after 4 to 5 days.

*R. fascians* D188-5 was transformed by electroporation in a similar manner but, due to its slower growth rate, it was incubated in LB overnight until it reached an $A_{600}$ of ~2.0. The cells were washed and resuspended in distilled water instead of sucrose. The Pulse Controller was set at 400 ohms and the recovery period after electroporation was in LB for 4 h before plating onto selective media. Successful transformation of *R. fascians* D188-5 with *E. coli* plasmids required that the DNA be methylated in vitro beforehand, using the CpG methylase, SssI (New England Biolabs, Inc., Beverly, Mass.).

Gas chromatography and mass spectroscopy

Cells were incubated overnight in LB medium at 30° C. and 100 µl was used to inoculate 50 ml of PMS minimal medium. The culture was incubated at 30° C. for 4 days, washed twice with sulfur-free PMS and the pelleted cells were inoculated into 50 ml of PMS that contained 0.1% DBT as the sole source of sulfur. These cells were incubated at 30° C. for 24 h and the supernatant was stored frozen at −20° C. For assays involving *R. fascians* D188-5, incubation times were increased 2 to 3-fold. Each sample supernatant (~50 ml) was thawed and residual insoluble material was removed by centrifugation. The cleared supernatant was acidified When cloning from a foreign bacterial genus into *E. coli*, not all genes are expressed nor are all protein products active. To assure that cloned desulfurization genes would be expressed in the host cell, a mutant of IGTS8 that could no longer desulfurize DBT was isolated. Using this mutant as a cloning recipient would insure that the cellular environment was appropriate for gene expression and protein function, thereby allowing screening for cloned desulfurization genes by complementation.

IGTS8 was mutagenized by exposure to UV light, and 1000 survivors were screened for the ability to produce a UV fluorescent product in the DBT spray plate assay. Three potential desulfurization negative mutants were identified and then re-evaluated in the sulfur bioavailability assay. Two mutants (designated UV1 and UV23) could not use DBT or DBT-sulfone as sole sources of sulfur and thus appeared to be Dsz–. When grown in the presence of DBT, mutant UV1 could not metabolize DBT to 2-HBP or to any other potential intermediate, as measured by GC/MS analysis. Therefore, strain UV1 was considered to be Dsz– and was used as the host for complementation studies to identify clones that carried desulfurization genes.

Cosmid cloning of desulfurization genes

DNA from Dsz+ source organism IGTS8 was used to construct a library in the cosmid vector, pLAFR5. This library was transduced into *E. coli* S17-1 and plasmids were isolated from approximately 25,000 colonies. These cosmids were electroporated into UV1, a Dsz– mutant of IGTS8, with an efficiency of ~300 transformants/µg DNA. Various numbers of UV1 transformants were pooled and incubated for 18 hours at 30° C., after which the cells were washed twice and resuspended in sulfate-free PMS. Approximately $7 \times 10^8$ pooled cells were inoculated into 100 ml of PMS with DBT as the sole source of sulfur. A predicted product of the DBT desulfurization reaction is 2-HBP, which is fluorescent when exposed to UV light. Therefore, batch cultures were grown at 30° C. and the supernatants were observed for fluorescence. Approximately 3300 UV1 transformants were screened in four separate batches. In one batch (representing ~600 transformants) a UV fluorescent product appeared in the supernatant after five days' incubation. Individual colonies were isolated and twelve of these continued to produce a fluorescent product when exposed to DBT.

Attempts to recover cosmid DNA from these isolates failed, so Southern hybridizations were performed to determine if the cosmids had become integrated into the chromosome of strain UV1. Chromosomal DNA was isolated from seven transformants and digested with EcoRI. After agarose electrophoresis and blotting, the fragments were hybridized with $^{32}$P-labelled probes derived from pLAFR5. In all transformants tested, pLAFR5 probes hybridized to a DNA fragment ~20 kb in size. Vector derived probes did not hybridize to the control IGTS8 genome. Therefore, the desulfurization positive cosmid clones had apparently integrated into the chromosome of strain UV1.

Since the plasmids had integrated into the chromosome, the genomic DNA connected to either side of the plasmid cloning site must represent IGTS8 sequences that were able to complement the Dsz– mutation in strain UV1. (This would be true regardless of whether the mode of integration was by homologous or illegitimate recombination.) Sequences were recovered that flanked the inserted plasmid from three desulfurization positive transformants by digesting genomic preparations with EcoRI or BamHI. These enzymes cut pLAFR5 once in the polylinker region so that an intact sequence of pLAFR5 could be recovered, linked to a neighboring chromosomal fragment from IGTS8. The digested DNA was ligated to itself (at a concentration of ~20 ng/μl) and was transformed into E. coli S17-1. Sixteen tetracycline resistant colonies were obtained, seven from the BamHI digestion and nine from the EcoRI digestion. Restriction enzyme analysis revealed that all the EcoRI-rescued clones contained a 2.1 kb fragment of IGTS8 DNA. The BamHI-rescued clones contained a 1.65 kb fragment from IGTS8.

The 2.1 kb IGTS8 DNA from the EcoRI rescue experiment was used as a template to make labelled DNA probes, which were hybridized to colony lifts of the original, intact cosmid library in E. coli. Of 5000 colonies, 17 hybridized with the IGTS8 probes. Cosmid DNA was isolated from each clone and transformed into strain UV1. Three of the seventeen DNA preparations complemented the Dsz– phenotype.

A restriction map for this region was constructed, using EcoRI and HindIII. Probes from the 2.1 kb IGTS8 DNA hybridized to the 4.5 kb EcoRI fragment. All cosmid clones that conferred the Dsz+ phenotype contained the entire 4.5 kb EcoRI fragment and portions of the 4.5 kb EcoRI-HindIII and 18 kb EcoRI, fragments. These results indicated that the desulfurization genes lay within a 15 kb region.

Subcloning the desulfurization genes

The 4.5 kb EcoRI and the 4.5 kb EcoRI-HindIII fragments were subcloned into pLAFR5, but neither fragment complemented the Dsz– mutation of strain UV1. The 9.0 kb EcoRI fragment from GE1-H, the 15.0 kb EcoRI-HindIII fragment from GE1-C, and the 18 kb EcoRI fragment from GE1-K were subcloned into pLAFR5 to yield the plasmids pSAD60-28, pSAD48-12, and pSAD56-6, respectively. When transformed into UV1, all three produced UV fluorescent products from DBT in the spray plate assay, consistent with the localization of the Dsz+ phenotype as determined by restriction mapping. Construction of additional subclones from this region narrowed the location of the relevant genes to a 6.5 kb BstBI fragment.

Nature of the mutation in strain UV1

Genomic blots of EcoRI digested IGTS8 and UV1 DNA were hybridized with probes produced from the 2.1 kb EcoRI-rescued fragment of IGTS8. No hybridization was detected to UV1 DNA, indicating that the UV1 mutation is a large deletion and not a simple point mutation.

A Rhodococcus plasmid origin of replication increases transformation of UV1

Electroporation of UV1 with pSAD48-12 typically resulted in a low transformation efficiency (~550/ μg DNA) and only about 50% of the transformants exhibited the Dsz+ phenotype (presumably because DNA had been lost or re-arranged during recombination with the chromosome). To improve the transformation efficiency, a 4.5 kb HindIII fragment from pRF29 was cloned into the HindIII site of pSAD48-12, resulting in pSAD74-12. This 4.5 kb fragment contains a Rhodococcus plasmid origin of replication, which allowed pSAD74-12 to replicate as a plasmid in strain UV1. This clone transformed UV1 with an efficiency of greater than $10^4$ transformants/μg DNA. Nearly 100% of these transformants exhibited the Dsz+ phenotype. Unfortunately, the yield of plasmid prepared directly from UV1 was so poor that DNA from minipreparations could not be visualized on agarose gels. However, plasmid isolated from UV1 could be used to transform E. coli S17-1, from which large amounts of the plasmid were prepared.

The Dsz+ phenotype is not expressed in E. coli S17-1

E. coli S17-1 was transformed with pSAD48-12 and desulfurization activity was measured with the spray plate assay. No positive colonies were identified. It was possible that the E. coli polymerase could not recognize the IGTS8 promoter(s) in pSAD48-12, so the IGTS8 DNA was placed under control of the E. coli lac promoter. The 15 kb EcoRI-HindIII IGTS8 fragment from pSAD48-12 was subcloned into the pBluescript vectors, SK$^-$ and KS$^-$, so that the IGTS8 fragment was cloned in both orientations with respect to the lac promoter. Neither clone expressed the Dsz+ phenotype in E. coli XL1-Blue. It is not yet known whether this stems from poor transcription or translation of the cloned genes or whether the overproduced proteins are inactive in E. coli S17-1.

The Dsz+ gene or genes are expressed in R. fascians

Since the cloned genes were either not expressed or produced inactive proteins in E. coli, efforts were initiated to express the genes in other Rhodococcus species. R. fascians D188-5 exhibited no desulfurization in the DBT spray plate assay or in the sulfur bioavailability assay. Initial attempts to transform R. fascians with the desulfurization positive plasmid, pSAD74-12 were unsuccessful. Other Rhodococcus species are known to have endogenous restriction systems that cleave DNA at SalI-like restriction sites. Since pSAD74-12 contained multiple SalI recognition sequences, CpG methylase, SssI, was used to methylate pSAD74-12 in vitro. With methylated pSAD74-12 DNA, transformants of R. fascians D188-5 were obtained with an efficiency of about $7 \times 10^3$ transformants/μg DNA. These transformants displayed the Dsz+ phenotype in the spray plate assay and GC analysis of liquid medium supernatant revealed the formation of 2-HBP from DBT.

Efforts to transform pSAD74-12 into a second species, R. rhodochrous ATCC13808 were ineffective, despite the use of unmethylated or CpG-methylated plasmid. It is possible that the electroporation conditions for ATCC13808 were not optimal, though a wide range of conditions was tested. It seems more likely that ATCC13808 has a restriction system that is not inhibited by CpG methylation.

2-HBP is the major desulfurization product

The predominant metabolite produced from DBT by R. rhodochrous IGTS8 is 2-HBP, with small amounts of 2'-hydroxybiphenyl-2-sulfinic acid (DBT-sultine) and 2'-hydroxybiphenyl-2-sulfonic acid (DBT-sultone) also identified by GC/MS analysis. These products were also produced by IGTS8 in this work (Table 2). Neither R. fascians D188-5 nor Dsz– mutant UV1 produced these products from DBT. However, when R. fascians D188-5 was transformed with plasmid pSAD74-12 and when the UV1 mutant was transformed with plasmid pSAD104-10, these bacteria produced products from DBT that were identical to those identified for IGTS8 (Table 2). In particular, 2-HBP was produced in large quantities, indicating that carbon-sulfur bond specific desulfurization of DBT was mediated by products of genes cloned from IGTS8.

One subclone, pSAD90-11, carried a DNA fragment that was supposedly identical to that cloned into pSAD104-10, but the two plasmids differed in the results they produced when introduced into UV1. In the plate assay, the surface film of DBT disappeared from the vicinity of colonies that contained pSAD104-10, producing a clear zone, and a fluorescent halo appeared around those colonies. On the other hand, when cells contained pSAD90-1, no fluorescent products were produced but a zone of DBT clearing did form around each colony. GC/MS analysis showed that no 2-HBP was produced by cells containing pSAD90-11, but that a significant amount of DBT-sultone did accumulate (Table 2). The sultone does not accumulate in the parent strain, UV1. These observations imply that when the 9.0 kb EcoRI fragment was subcloned into pSAD90-11 the DNA was damaged so as to inactivate the gene(s) encoding the enzyme(s) that convert the sultone to 2-HBP. This suggests that at least two enzymes are involved in desulfurization and that the sultone may be an intermediate in the pathway. This result is consistent with the kinds of metabolites detected in the original isolate, IGTS8.

TABLE 2

Metabolites produced from DBT by Rhodococcus species transformed with subclones derived from IGTS8.

| | Rhodococcus species (plasmid) | | | |
| --- | --- | --- | --- | --- |
| Metabolite[a] | IGTS8 | UV1 (pSAD104-10)[b] | UV1 (pSAD90-11)[c] | R. fascians D188-5 (pSAD-74-12)[d] |
| DBT | ++++[e] | ++++[e] | ++++ | ++ |
| DBTO | + | 0 | 0 | 0 |
| DBTO$_2$ | 0 | 0 | 0 | 0 |
| DBT-sultone | + | ++ | ++ | + |
| DBT-sultine | 0 or trace | 0 | trace | + |
| 2-HBP | +++++ | +++++ | 0 | +++ |

[a]Products are: DBT, dibenzothiophene; DBTO, dibenzothiophene 5-oxide (sulfoxide); DBTO$_2$, dibenzothiophene 5,5-dioxide (sulfone); DBT-sultone, 2'-hydroxybiphenyl-2-sulfonic acid (detected as dibenz[c,e][1,2]-oxathiin 6,6-dioxide); DBT-sultine, 2'-hydroxybiphenyl-2-sulfinic acid (detected as dibenz[c,e][1,2]-oxathiin 6-oxide); dibenzothiophene sulfone; 2-HBP, 2-hydroxybiphenyl (Krawiec, pg. 103–114. In G. E. Pierce (ed.), Developments in Industrial Microbiology, vol 31, Society for Industrial Microbiology, Columbus, Ohio, 1990).
[b]9.0 kb EcoRI DNA fragment from IGTS8 subcloned into pLAFR5, plus the origin of replication from pRF29.
[c]Mutated 9.0 kb EcoRI DNA fragment from IGTS8 subcloned into pLAFR5, plus the origin of replication from pRF29.
[d]15.0 kb EcoRI-HindIII DNA fragment from IGTS8 subcloned into pLAFR5, plus the origin of replication from pRF29.
[e]Presence of metabolites is reported in relative amounts from very large amounts (+++++) to very small (+), i.e., trace amounts.

IGTS8 cannot use DBT-sulfoxide as a sulfur source

IGTS8 was incubated in minimal medium with one of the following as the sole source of sulfur: DBT, DBT-sulfoxide, or DBT-sulfone. IGTS8 was incapable of utilizing the sulfur supplied by DBT-sulfoxide but grew well in the presence of DBT or DBT-sulfone. DBT-sulfoxide was not toxic to cells when grown in a rich medium (LB). Therefore, either IGTS8 cannot transport or otherwise act on DBT-sulfoxide, or else DBT-sulfoxide is not a true intermediate of the desulfurization pathway.

EXAMPLE 4

DNA Sequencing of a 9763 Nucleotide
EcoRI-Sau3AI Fragment Containing the Gene or
Genes for the Deuslfurization Biocatalyst of IGTS8
by the Method of Sanger et at.

A 9763 nucleotide EcoRI-Sau3AI fragment containing the gene or genes responsible for the Dsz+ phenotype was isolated from the IGTS8 source organism. The DNA sequence of this fragment was determined from both strands of DNA using the dideoxy chain-termination method of Sanger et al. (1977), DNA sequencing with chain-termination inhibitors, 74 Proc. Natl. Acad. Sci. USA 5463–5467, a modified T7 DNA polymerase (USB) and [α-$^{35}$S]-dCTP (Amersham). Deletion clones for DNA sequencing were constructed in pBluescript (Stratagene) using exonuclease III and the methods of Henikoff (1984), Unidirectional digestion with exonuclease III creates targeted breakpoints for DNA sequencing, 28 Gene 351–359.

Sequences from 141 individual deletion clones were used to reconstruct the entire 9763 nucleotide fragment. Computerized sequence assembly was performed using DNA InspectorII (Textco, Hanover, N.H.). The DNA sequence was determined independently for each strand of DNA, but the entire 9763 nucleotide fragment was not completely sequenced on both strands. The sequence determined from one strand of DNA covered 95% of the 9763 nucleotide sequence. On the other DNA strand, 96% of the sequence was determined. The sequence was determined from at least two independent deletion clones for the entire 9763 nucleotide fragment.

EXAMPLE 5

Figure 7:
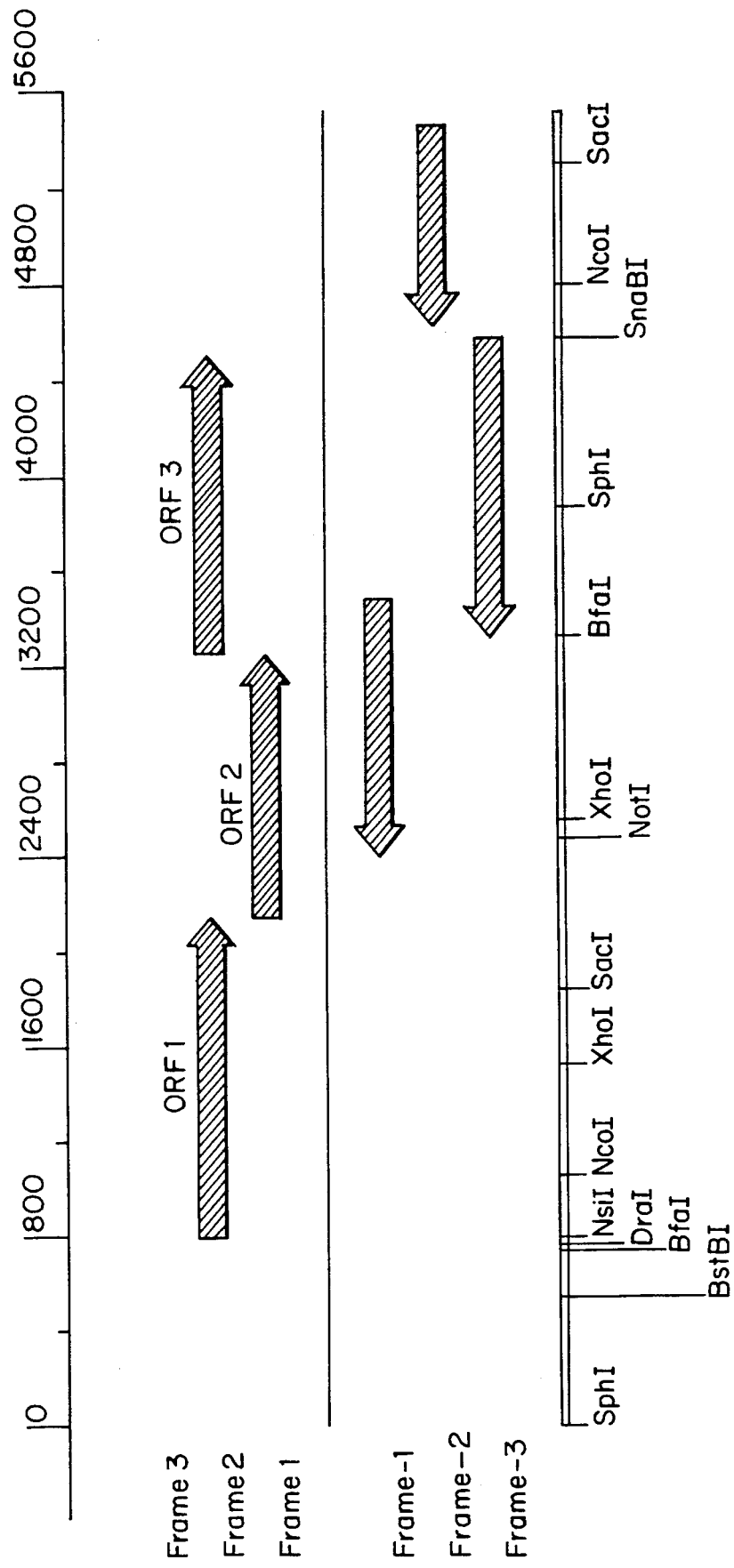
FIG. 7 is a schematic illustration of the predicted locations within the sequence of pTOXI-1 of three nearly contiguous open reading frames (ORFs; specifically, ORF 1, ORF 2 and ORF 3) encoding polypeptide expression products responsible for the Dsz+ phenotype.
Figure 8A:
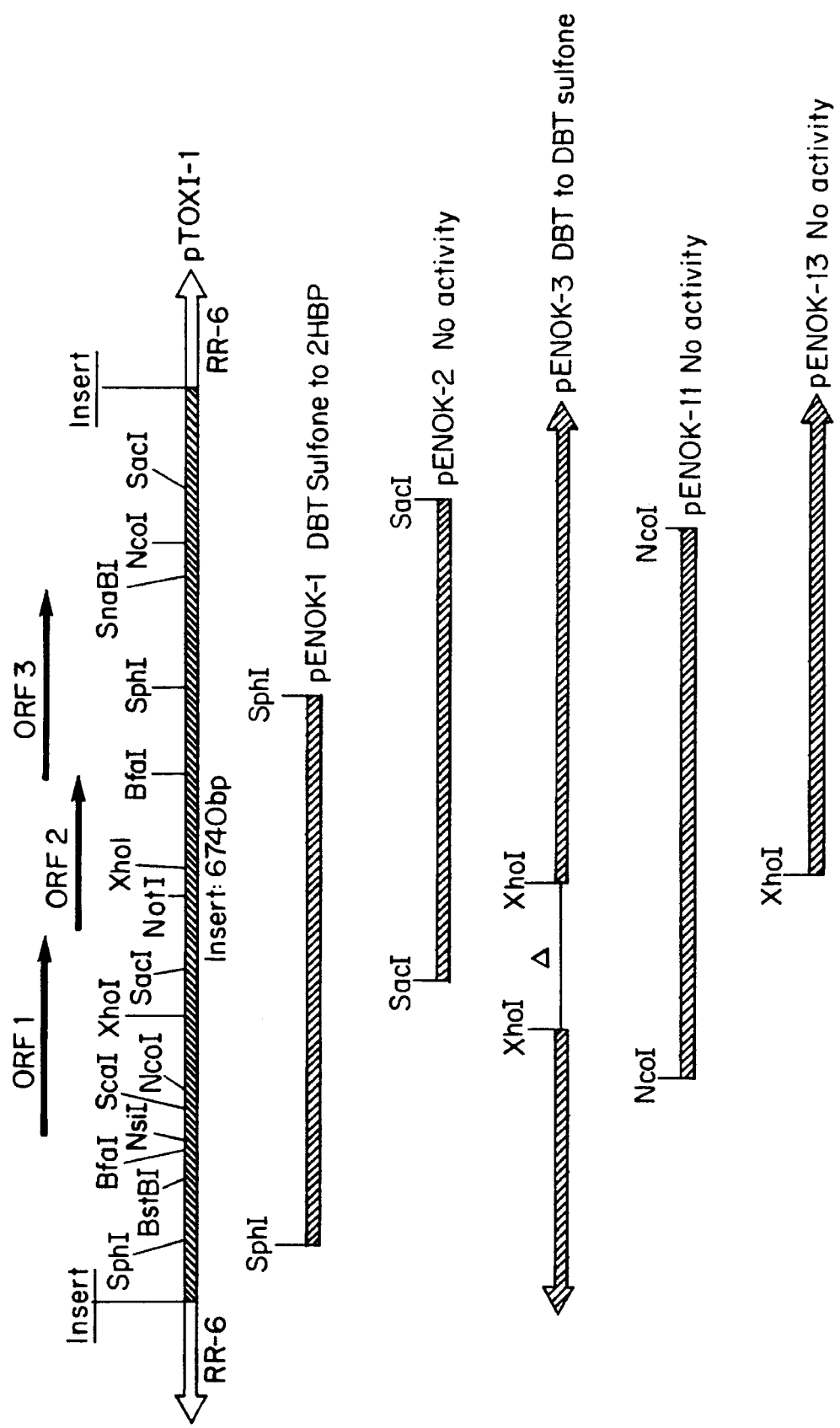
FIGS. 8A and 8B are a schematic illustration of the restriction map of pTOXI-1 and fragments thereof present as inserts in subclones pENOK-1, pENOK-2, pENOK-3, pENOK-11, pENOK-13, pENOK-16, pENOK-18, pENOK-Nsi, pENOK-19 AND pENOK-20.
Figure 8B:
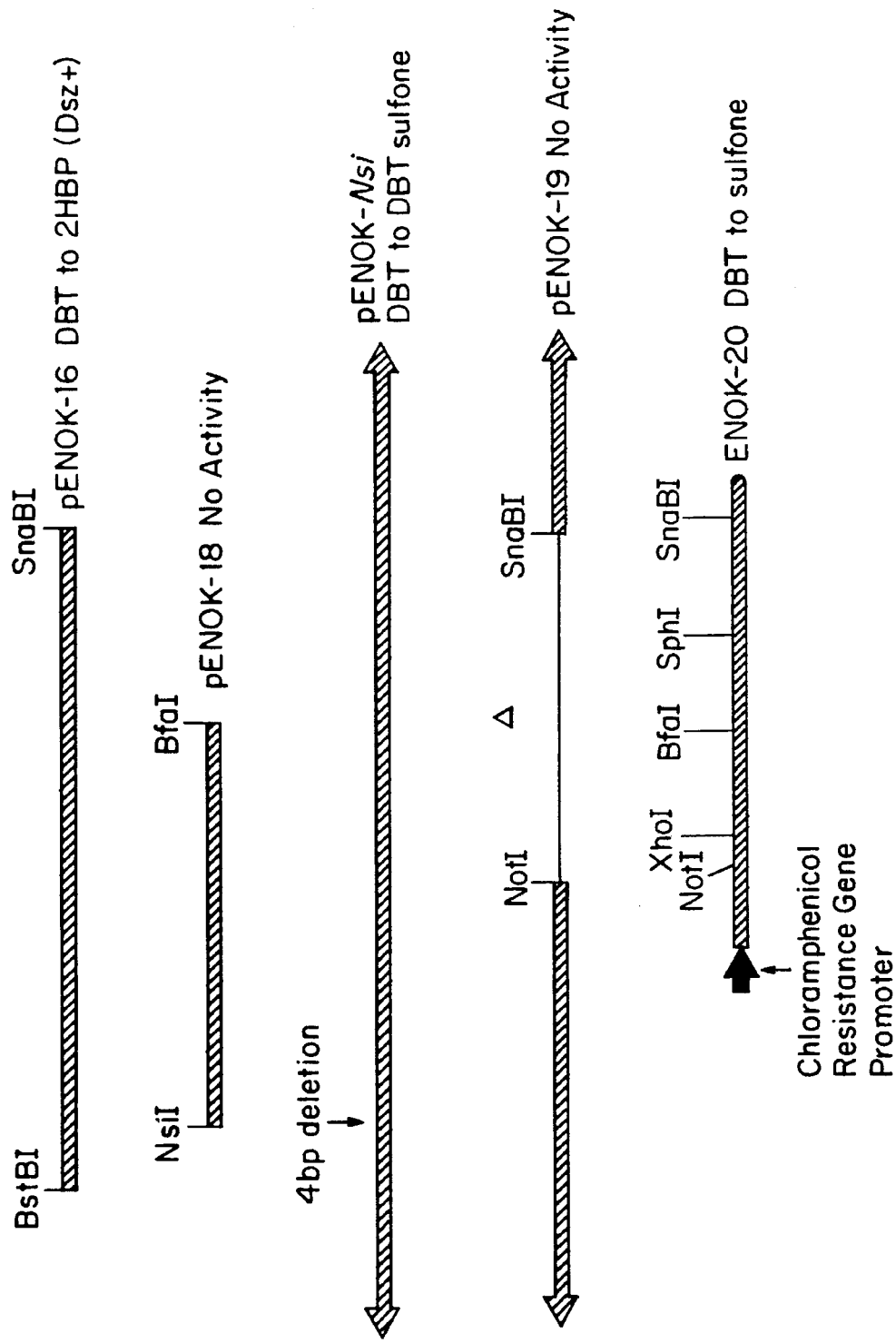

Further Resolution of the Sequence of pTOXI-1
and Open Reading Frames (ORFs) Encoded
therein; Dsz+ Promoter Engineering; Expression of
the Dsz+ Phenotype in a Heterologous Host
Organism; Maxicell Analysis of Desulfurization
Gene Expression Products Organization of the desulfurization cluster Sequencing of pTOXI-1, the results of which are set forth below in the Sequence Listing, predicted three nearly contiguous open reading frames (ORFs) on one strand of the clone (FIG. 7). The sizes of each ORF are predicated as 1359 bases (bps 786–2144) for ORF 1, 1095 bases (bps 2144–238) for ORF 2 and 1251 bases (bps 3252–4502) for ORF 3. Subclone analysis described below has revealed that ORFs 1, 2 and 3 are required for the conversion of DBT to 2-HBP and that all of the genes encoded by these ORFs are transcribed on a single transcript as an operon. All subclones described below are maintained in E. coli - Rhodococcus shuttle vector pRR-6. Activity of each subclone was determined by growing transformants of Dsz– strain CPE-648 in a rich media (RM) for 48 hours. 1 ml of the culture was used to inoculate 25 ml BSM supplemented with greater than 100 μM DBT or DBT-sulfone. Cultures were assayed for desulfurization products after 48–120 hours. A diagram of each of the subcloned fragments is shown in FIGS. 8A and 8B.

In subsequent studies, the subclones were grown in rich media with chloramphenicol, then crossed into BSM supplemented with 100 μM of either DBT or DBT-sulfone. Cultures were shaken at 30° C. for 2–5 days and assayed for desulfurization products by HPLC.

A. pENOK-1: A subclone was constructed which contains the 4.0 kb SphI fragment of pTOXI-1. This fragment spans ORFs 1 and 2 but truncates ORF 3. Analysis of pENOK-1 containing transformants revealed the production of no products when incubated with DBT. However these transformants were capable of producing 2-HBP from DBT-sulfone.

B. pENOK-2: A subclone which contains the 3.6 kb SacI fragment of pTOXI-1 was constructed. This fragment contains ORFs 2 and 3 but truncates ORF 1. Analysis of pENOK-2 transformants revealed no production of any desulfurization products from either DBT or DBT-sulfone. The lack of any activity detectable from either ORFs 2 or 3 suggests that the ORFs are arranged as an operon with transcription mediated from a single upstream promoter. Presumable, this promoter has been removed in this subclone.

C. pENOK-3: A 1.1 kb XhoI deletion mutation of pTOXI-1 was constructed. Both ORFs 1 and 2 are truncated. ORF 3 remains intact. Transformants harboring pENOK-3 show production of DBT-sulfone from DBT. No production of 2-HBP is detected from either DBT or DBT-sulfone. It should also be noted that at the nucleotide level, a deletion of this type would not result in a polar mutation. The sequence predicts an in-frame splicing of ORFs 1 and 2 which would produce a hybrid protein that is presumably inactive. However, by avoiding stop codons, the putative single mRNA transcript remains protected by ribosomes allowing for translation of ORF 3. The ability of the ORF-3 product to produce DBT-sulfone from DBT demonstrates that DBT-sulfone is a true intermediate in the carbon-sulfur bond specific biocatalytic desulfurization pathway of IGTS8.

D. pENOK-11: The 3.4 kb NcoI fragment from pTOXI-1 was subcloned into a unique NcoI site of pRR-6. This fragment contains all of ORFs 2 and 3 but truncates the 5'end of ORF1. Transformants with pENOK-11 demonstrated no desulfurizing-specific enzymatic activity towards DBT or DBT-sulfone. This indicates essential coding regions bordering this fragment. This is consistent with the predication that the entire cluster is expressed on a single transcript as discussed for subclone pENOK-2. Again, the promoter for gene transcription is not present in this subclone. Sub-clone pENOK-13 (below) corroborates this prediction.

E. pENOK-13: A subclone of pTOXI-1 was constructed which had a 2.6 kb SphI-XhoI deletion. This subclone only contains an intact ORF 3. ORF 1 is lost completely and ORF 2 is truncated. This subclone showed no desulfurizing-specific enzymatic activity towards DBT or DBT-sulfone. This result should be compared with the phenotype of pENOK-3 which demonstrated production of DBT-sulfone from DBT. Because pENOK-13 differs from pENOK-3 by the additional deletion of the smaller SphI/XhoI fragment, this would indicate an element in the 1.6 kb SphI/XhoI fragment which is essential for gene expression. Because sequencing has revealed no significant ORF's contained in this region, it is postulated that a promoter element may be present in this region.

F. pENOK-16: A subclone of pTOXI-1 was designed which eliminates nearly all unnecessary sequences from the desulfurization cluster. This construct contains the 4 kb BstBI-SnaBI which presumably contains all essential sequence for complete desulfurization in that in contains all of ORFs 1, 2 and 3 as well as 234 bases of upstream sequence. The 3' SnaBI site lies 80 base pairs beyond the termination of ORF 3. CPE-648 harboring this plasmid was capable of converting DBT and DBT-sulfone to 2-HBP. pENOK-16 thus represents the smallest amount of the cluster yet observed which demonstrates the complete desulfurization phenotype.

G. pENOK-18: This subclone contains a NsiI-BfaI fragment of pTOXI-1. The NsiI site is 23 bp down-stream of the predicted start site of ORF 1. CPE-648 harboring this subclone lacks desulfurization activity on both DBT and DBT-sulfone. This subclone most likely eliminates the promoter region and truncates the first structural gene.

H. pENOK-Nsi: To help further elucidate the start site of ORF 1, a subclone was made in which a 4 bp deletion is introduced at the unique NsiI site which is 23 bp downstream of the predicted start site of ORF1. The mutation was generated by cutting with NsiI and blunting the ends with T4 DNA Polymerase. If the NsiI site is within the first structural gene this frameshift mutation would cause an early stop signal in ORF 1. Transformants of pENOK-Nsi were capable of producing DBT-sulfone from DBT. However, no production of 2-HBP was detected indicating that the mutation had disrupted an essential structural gene.

In subsequent studies, due to the clear expression of the ORF-3 encoded oxidase, in this clone, it was considered likely that the ORF-2 product would also be expressed. Accordingly, ORF-2 alone is incapable of further metabolism of DBT-sulfone.

I. pENOK-19: A subclone of pTOXI-1 was constructed which contains a deletion from the NotI site, which is in the earlier part of ORF 2, to the SnaBI which is after ORF 3. This subclone should demonstrate the activity of ORF 1 alone. CPE648 transformants harboring this subclone displayed no enzymatic activity towards DBT or DBT-sulfone.

The results of pENOK-Nsi and pENOK-19, taken together, suggest that the ORF-I and ORF-2 products must be simultaneously expressed in order to further metabolize DBT-sulfone.

J. pENOK-20: In order to evaluate the function of ORFs 2 and 3 separately from ORF 1, DNA spanning ORFs 2 and 3 was amplified by the Polymerase Chain Reaction (PCR). Primers RAP-1 (5'-GCGAATTCCGCACCGAGTACC-3'(SEQ ID NO:8), bps 2062-2082) and RAP-2 (5'-ATC-CATATGCGCACTACGAATCC-3'(SEQ ID NO:9), bps 4908-4886) were synthesized with the Applied Biosystems 392 DNA/RNA Synthesizer. Nucleotides in bold were altered from the template sequence in order to create restriction sites for subcloning; thus primer RAP-1 contains an EcoRI site, and primer RAP-2 contains an NdeI site. Amplification was carried out with the GeneAmp Kit (Perkin Elmer Cetus) which utilizes the Taq polymerase and the Perkin Elmer Cetus 9600 Thermocycler. Parameters were as follows:

| Template: | pMELV-1 Plasmid DNA | | 0.2 or 2.0 ng |
|---|---|---|---|
| Primers: | RAP-1 | | 0.5 or 0.2 μM |
| | RAP-2 | | 0.5 or 0.2 μM |
| Cycles: | 1x @ | 96° C. | 2 min |
| | 25x @ | 96° C. | 30 sec |
| | | 52° C. | 30 sec |
| | | 72° C. | 2 min |

Amplification yielded the predicted 2846 bp fragment. In order to express the amplified fragment harboring ORFs 2 and 3, it was ligated to the XbaI/EcoRI fragment of the chloramphenicol resistance gene promoter from *Rhodococcus fascians* (Desomer et al.: Molecular Microbiology (1992) 6 (16), 2377–2385) to give plasmid pOTTO-1. Ultimately, a blunt end ligation was used for the subcloning of the amplified product due to the fact that ligation using the engineered restriction sites was unsuccessful. This fusion was ligated to shuttle-vector pRR-6 to produce plasmid pENOK-20. CPE648 transformants of pENOK-20 were grown in the presence of DBT and 25 μg/ml chloramphenicol for promoter induction. All transformants converted DBT to DBT-sulfone presumably through the activity of the ORF 3 as demonstrated in subclone pENOK-3. The inability to further process DBT-sulfone with the presence of ORF 2 suggests that the product of ORF 2 alone is incapable of using DBT-sulfone as a substrate. This is consistant with results obtained from pENOK-Nsi, and suggests that ORF-2 alone is incapable of using DBT-sulfone as a substrate.

Assignment of Gene Products of ORFs 1, 2 and 3

Based on the foregoing subclone analyses, functions have been tentatively assigned to each of the ORFs present within the pTOXI-1 sequence. ORF 3 can be identified as responsible for an oxidase capable of conversion of DBT to DBT-sulfone. Subclone pENOK-3 demonstrates this activity very clearly. ORFs 1 and 2 appear to be responsible for conversion of DBT-sulfone to 2-HBP. This aryl sulfatase activity is evidenced in subclone pENOK-1. However subclones pENOK-19 and pENOK-20 indicate that neither ORF 1 nor ORF 2 is capable of any conversion of the intermediate DBT-sulfone. This suggests that the protein products of ORFs 1 and 2 work together to cleave both of the carbon-sulfur bonds. Presumably, this is achieved through a heterodimer arrangement of the proteins, or through a regulatory function of one protein on the other. The results of parallel investigations, presented in Example 3, suggested that ORF-1 encodes an enzyme that converts DBT-sulfone to DBT-sultone. Lengthy incubations of CPE-648 harboring pENOK-19 (intact native promoter and ORF-I) have shown neither the depletion of DBT-sulfone nor the production of any new products. This is contrary to indications derived from Example 3.

Alternative Promoter Screening

Increasing the specific activity of desulfurization is a significant objective of the studies described herein. One approach to accomplishing this goal is to replace the original promoter with one that can produce both higher and constitutive expression of the desulfurization gene cluster. Because there are so few reported and characterized Rhodococcus promoters, random genomic libraries have been prepared and screened for promoter activity in two systems. In one, the reporter is the chloramphenicol resistance gene used in the above-discussed plasmid constructions. In the other, the desulfurization cluster itself is used as a reporter.

Promoter Screening Example A. Chloramphenicol Resistance Reporter.

As also described below, partially digested Rhodococcus genomic DNA has been cloned upstream of a promoterless chloramphenicol resistance gene. The resulting libraries were then transformed into Rhodococcus which are subjected to chloramphenicol selection. Four apparent promoter elements were rescued by pRHODOPRO-2, although plasmid could be isolated from only one of these, possibly due to vector instability. The stable plasmid RP2-2A has been subjected to sequence analysis. Technical problems have been observed with restriction enzyme treatment of the NarI cloning site used in these vectors. Unfortunately, the NarI enzyme demonstrates severe site-selectivity and does not appear to digest the vector well. New vectors have been constructed in order to alleviate this problem, although a lack of convenient and unique restriction sites slowed the progress of these studies. A recent observation on the Rhodococcus replication origin will aid in constructing a more effective promoter probe, as discussed below.

Figure 9:
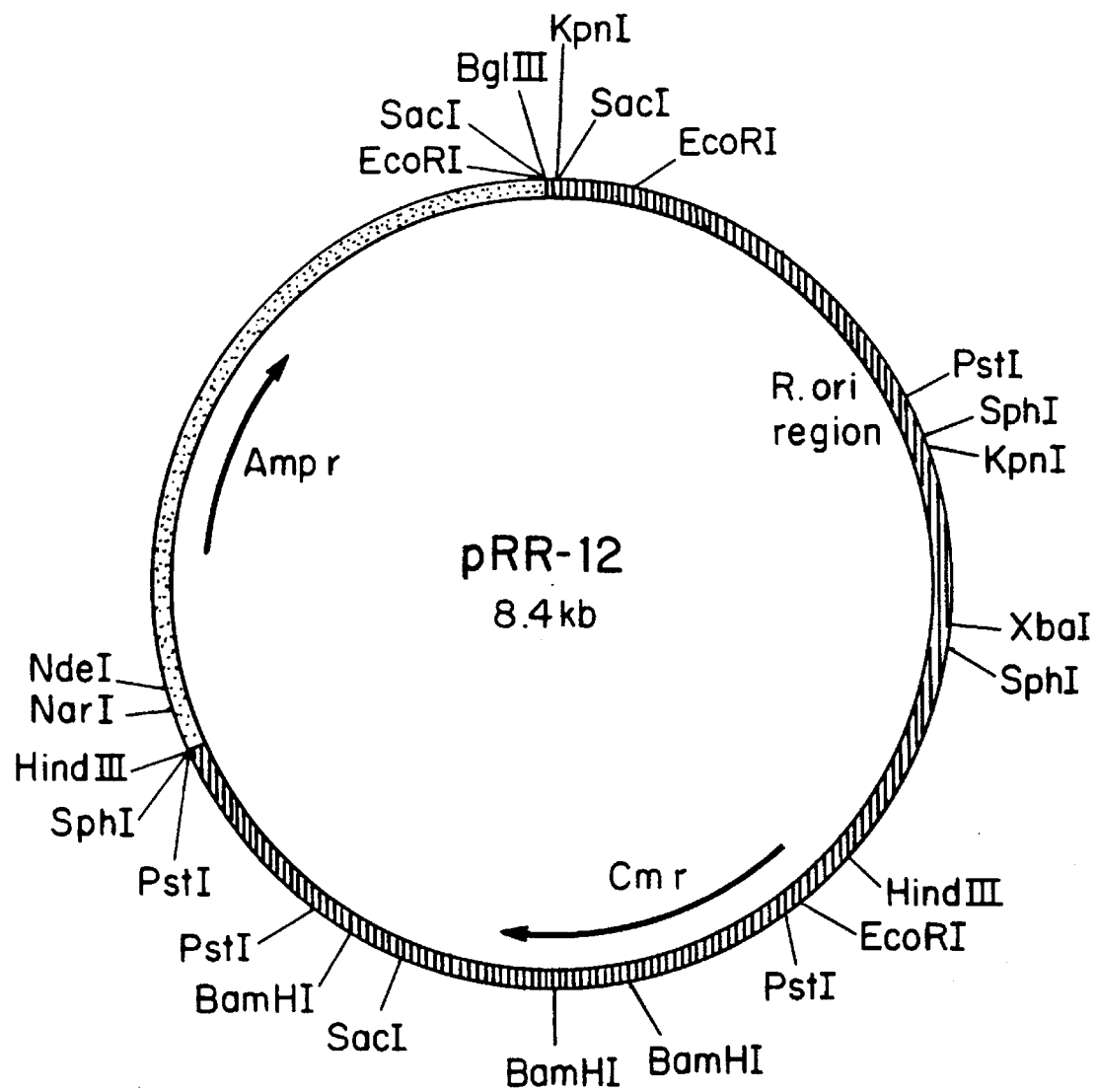
FIG. 9 is a schematic illustration of the restriction map of pRR-12.

Recently, the 1.4 kb BglII fragment was removed from pRR-6, and the ends were blunted and religated to produce pRR-12 (FIG. 9), which contains no BglII sites. Desomer et al. (Molecular Microbiology (1992) 6 (16), 2377–2385) reported that this region was needed for plasmid replication. Thus, it was surprising that this construct was capable of producing Cm$^r$ transformants, indicating that this region was not essential for plasmid replication in the strain of organisms used for the present studies. This observation forms the conceptual basis for construction of a vector that will utilize a synthesized BglII site for cloning the random genomic fragments. BglII accepts DNA digested by Sau3A, an effective and frequent cutter of IGTS8 DNA. These constructs are expected to allow for the production of better, more representative random genomic libraries.

Promoter Screening Example B: Desulfurization Cluster Reporter.

Figures 10, 10A:
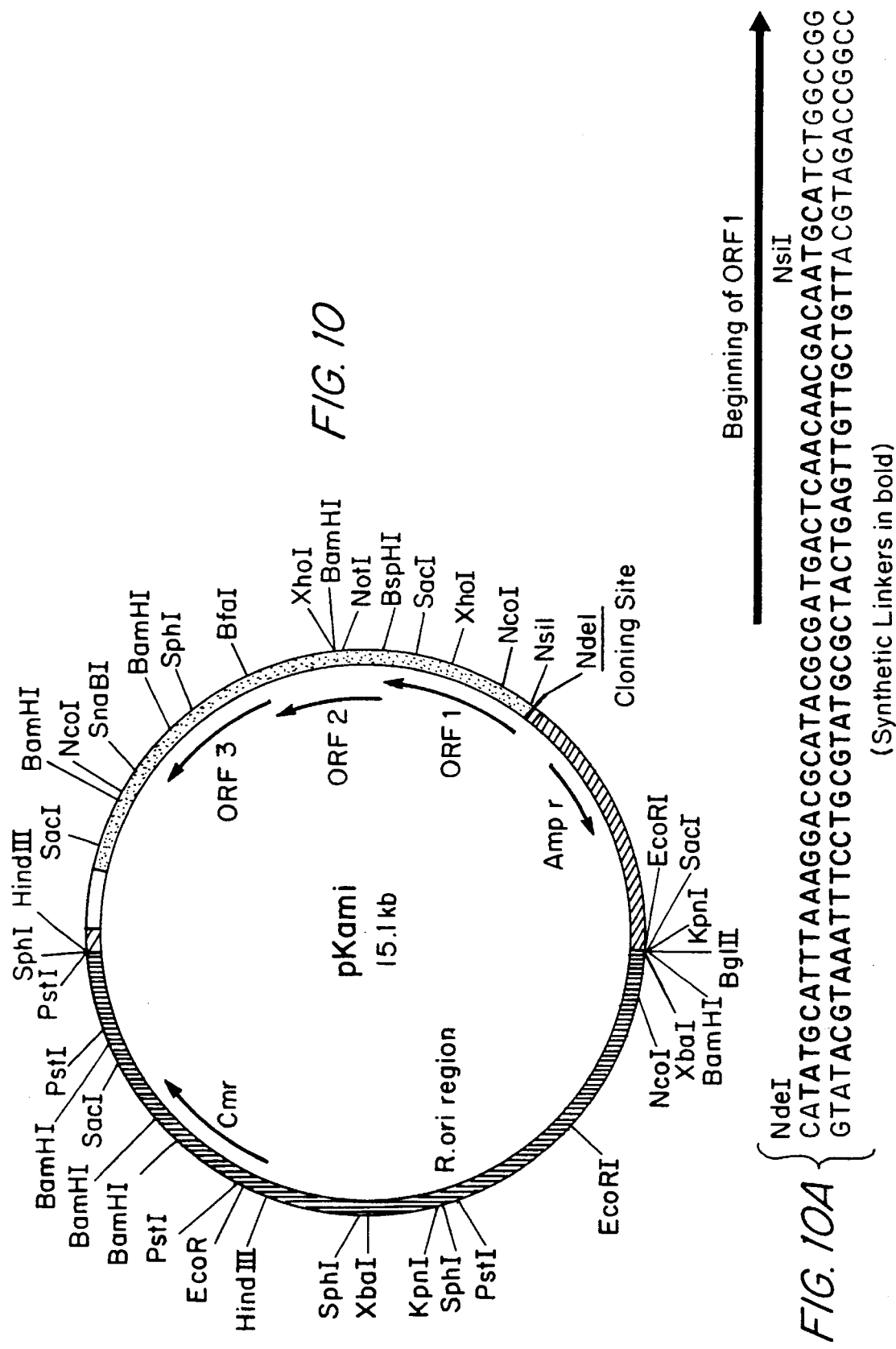
FIG. 10 is a schematic illustration of the restriction map of vector pKAMI. In the inset (FIG. 10A, SEQ. ID NO: 16), the engineered cloning site present in pKAMI is shown in detail.

Vector pKAMI has been used as a second direct "shotgun" approach to finding a suitable alternative promoter (FIG. 10). An NdeI site was engineered upstream of the promoterless Dsz cluster to serve as the site of insertion of random genomic DNA (from strains GPE-362, CPE-648 and IGTS8) fractionated by NdeI and the compatible 4bp cutters MseI and BfaI. Originally, this ligation mixture was directly transformed into GPE-362 cells, which were then used en masse to inoculate 250 ml BSM+DBT. These efforts were undertaken with the goal of amplifying a superior Dsz+ strain due to its ability to utilize DBT as the sole source of sulfur. To date, 14 transformations of this type have been done. Of these, all but 2 have resulted in producing Dsz+ cultures. Eleven individual clones have been isolated and characterized. These are capable of low-level (0.6–1.0 mg/L 2-HBP/OD$_{600}$/hr), constitutive expression of the desulfurization trait. Restriction analysis of plasmids isolated from these eleven has revealed that all but one (KB4-3) are simple rearrangements of the pKAMI backbone resulting in gratuitous expression from vector borne promoters. Many of the rescued plasmids show identical restriction patterns although originating from separate ligations, suggesting an inherent vector instability. It appears as if, with this type of selection, rearrangements of pKAMI that utilize a vector promoter sequence are strongly selected.

The above-described selection procedure has thus given way to a promoter screen geared to minimize the plasmid rearrangement. In this procedure, the pKAMI/genomic library is first amplified in E. coli, then the individual JM109 colonies are pooled together. The plasmids are extracted, and used to transform Dsz– strain GPE-362. Instead of using en masse enrichment, the GPE362 transformations are plated to Rich Media+ chloramphenicol for selection of plasmid containing cells. Resulting colonies are replica-plated to BSM agarose+DBT plates, then checked for desulfurization activity by UV fluorescence production. Over 7,000 GPE-362 transformants have been screened in this fashion. Thirty-six have been isolated from these which produce UV fluorescence on BSM+DBT plates. Current efforts focus on the identification and characterization of the engineered plasmids borne by these 36 transformants.

Alternative Promotor Engineering

The close physical arrangement of the three ORFs of pTOXI-1 does not provide sufficient space for promoters for either ORFs 2 or 3. This fact, coupled with the results of the subclone analysis in which intact ORFs 2 and 3 provided no activity (see pENOK-2, pENOK-11, and pENOK-13), suggested that this cluster of genes is organized as an operon with only one promoter for expression of the three genes. Given that the desulfurization trait of IGTS8 is repressed by sulfate (Kilbane and Bielaga, Final Report D.O.E. Contract No. DE-AC22-88PC8891 (1991), it is possible that the operon promoter is tightly controlled by sulfur levels. With the elucidation of the molecular arrangement of the desulfurization cluster, alternative promoters can be rationally engineered to eliminate the sulfur repression, increase expression of the desulfurization genes and thereby increase the specific activity of the $Dsz^+$ trait.

Examples of potential alternative promoters include other known and described promoters such as the chloramphenicol resistance gene promoter from *Rhodococcus fascians* (Desomer et al.: Molecular Microbiology (1992) 6 (16), 2377–2385), the nitrile hydratase gene promoter from *Rhodococcus rhodochrous* (Kobayashi, et al.: Biochimica et Biophysica Acta, 1129 (1991) 23–33), or other strong promoters isolated from Rhodococcus sp. by "shot-gun" promoter probing. Other potential alternative promoters include those from other Gram positive organisms such as Corynebacterium, Bacillus, Streptomyces, and the like.

Figure 11:
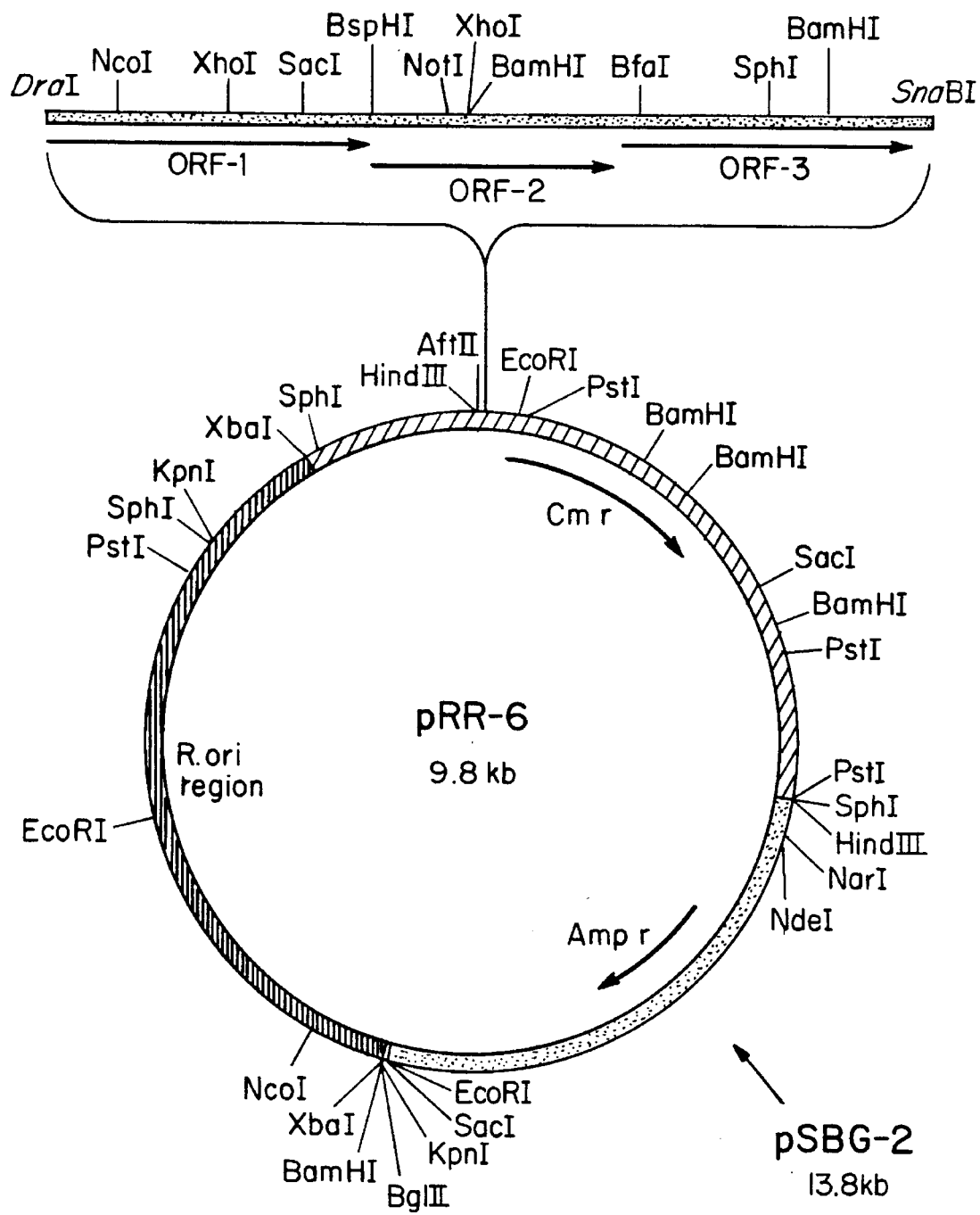
FIG. 11 is a schematic illustration of the restriction map of pSBG-2, in which expression of a promoterless Dsz gene cluster from pTOXI-1 is driven by the chloramphenicol resistance promoter.

Promoter Engineering Example A: Expression from the chloramphenicol resistance gene promoter from *Rhodococcus fascians*.

pSBG-2 (FIG. 11). The promoterless desulfurization cluster was isolated from pTOXI-1 as a 4.0 kb DraI/SnaBI fragment and ligated to a unique blunted AflII site of pRR-6. This ligation inserted the cluster down-stream of the chloramphenicol resistance gene promoter and upstream of the resistance structural gene. Thus, messenger RNA (mRNA) transcription should proceed through the Dsz gene cluster and proceed on to the resistance gene. However, original selections of transformants on chloramphenicol did not yield transformants, suggesting poor transcriptional read-through. Dsz+ transformants harboring the plasmid were selected first through sulfur bioavailability assays and secondarily on chloramphenicol plates. Unlike IGTS8, pSBG-2 transformants are capable of converting DBT to 2-HBP in BSM media supplemented with 20 mM $Na_2SO_4$, which demonstrates the removal of sulfate repression by promoter replacement. Specific activity of transformants was measured between 0.9 and 1.7 mg 2-HBP/1/$OD_{600}$/hr for a 16 hr culture in a rich media (RM) supplemented with 25 μg/ml chloramphenicol.

pSBG-3. The Rhodococcus origin of replication was removed from pSBG-2 by elimination of the 4.0 kb XbaI fragment. Without the origin, transformation is obtainable only through integration. CPE-648 transformants with this plasmid were selected on RM+ chloramphenicol and replica-plated onto BSM+DBT plates. Colonies were obtained which produced 2-HBP, as detected by fluorescence after 18 hr of incubation at 30° C.

Individual expression of each ORF

Recently, studies have been initiated to express the three ORFs separately, each engineered with an alternative promoter. These studies are expected to elucidate the following: First, any potential rate limiting steps in the desulfurization process will be identified and overcome. Potential polarity effects of operon expression, i.e. poorer expression of down-stream ORFs 2 and 3, may be causing such rate limitations. Also, given the unresolved issue of the individual functions of ORFs 1 and 2, these studies are expected to demonstrate reconstitution of DBT-sulfone to 2-HBP conversion by the separate expression of ORFs 1 and 2.

All ORFs were isolated through PCR amplification and subsequent subcloning. A typical Shine-Dalgarno sequence and a unique cloning site for alternative promoters has been engineered upstream of each ORF. Stop codons in all reading frames have been engineered down-stream of each ORF to prevent read-through. Additionally, convenient flanking restriction sites for mobilization of the promoter/ORF fusions have been added to each primer. The primers used for amplification of each ORF are listed below. In-frame stop codons are marked with an asterik (*). Sequences identical to pTOXI-I template DNA are shown in bold.

ORF1UP, SEQ ID NO: 10:

```
            XbaI
5'-GGAATTCTAGACATATGAGGAACAGACCATGACTCAACAACGACAAATGC-3'
    EcoRI      NdeI              Start
```

ORF1DOWN, SEQ ID NO: 11:

```
                          Stop XbaI
3'-GTACTGTTCGGCGCAGCTGGGGACTAAGATCTTAAGC-5'
   Stop*                  Stop    EcoRI
```

ORF2UP, SEQ ID NO: 12:

```
            BglII
5'-GGAATTCAGATCTCATATGAGGAAACAGACCATGACAAGCCGCGTCGACC-3'
    EcoRI      NdeI              Start
```

ORF2DOWN, SEQ ID NO: 13:

```
                        StopBglII
3'-CGGAGTTAGCGGTGGCTATCCTTAATCTAGACTTAAGC-5'
                   Stop*   Stop    BglII
```

ORF3UP, SEQ ID NO: 14:

```
           MseI
5'-GGAATTCTTAACATATGAGGAAACAGACCATGACACTGTCACCTGA-3'
   EcoRI       NdeI              Start
```

ORF3DOWN, SEQ ID NO: 15:

-continued

```
                         MseI
3'-GACTCCTAGACTCCGCGACTAATTCTTAAGC-5'
   Stop*   Stop       Stop    EcoRI
```

Cycling parameters were: 1 × 96° C. 2.0 min
25 × 96° C. 30 sec
50° C. 30 sec
72° C. 1.0 min Each ORF has been successfully amplified and subcloned into pUC-19 NdeI as EcoRI fragments. Alternative promoters will be ligated into the unique NdeI sites, and the fusions will be moved to Rhodococcus-*E. coli* shuttle vector pRR-6 for expression in Rhodococcus.

Heterologous Expression of the Dsz+ Trait

In order to determine whether plasmid pTOXI-1 contained all of the genetic material necessary for the Dsz+ trait, heterologous expression of pTOXI-1 was attempted in *Rhodococcus fascians*, a related organism which does not metabolize DBT (Dsz−) and in *E. coli*, a non-related organism which is also Dsz−.

A. *Rhodococcus fascians* (ATCC 12974), a Dsz− strain, was transformed with pTOXI-1. A single transformant demonstrated UV fluorescence on BSM+DBT plates, and further analysis by HPLC clearly indicated production of 2-HBP when DBT was provided as a substrate. Thus pTOXI-1 contains sufficient information to convert a heterologous Dsz− strain to the Dsz+ phenotype.

B. *E. coli* strain JM109 was also transformed with pTOXI-1 and was incubated with each of the substrates DBT and DBT-sulfone in either a minimal media (BSM) or a rich media (Luria Broth). In no case was production of 2-HBP observed by HPLC analysis. The inability of *E. coli* to express the desulfurization genes was not unexpected as gram positive genes are not universally expressible in *E. coli* without promoter replacement.

In order to replace the promoter of the desulfurization cluster, a 4.0 kb DraI/SnaBI fragment was isolated from pTOXI-1. This fragment contains all of the necessary structural genes but lacks the promoter sequences. This promoterless desulfurization cluster was ligated to *E. coli* expression vector pDR540 (Pharmacia, Piscataway, N.J.) cut with BamHI and ends made blunt with Klenow. The construction fuses the tac promoter to the desulfurization cluster. The tac promoter is under control of the lactose repressor and is repressed in a lacI$^q$ host such as JM109. Expression from the tac promoter is inducible by the addition of isopropyl β-D-thiogalactopyranoside (IPTG). Transformants of JM109 harboring pDRDsz grown in Luria Broth at 30° C. demonstrate the Dsz+ phenotype when incubated with DBT and induced with IPTG. A specific activity as high as 1.69 mg 2HBP/1/OD$_{600}$/hr has been observed with pDRDsz. Activity is greatly diminished when transformants are grown at 37° C. The highest level of activity has been observed at 1 hr post induction.

The above-described expression of the Dsz+ trait in both a related and non-related heterologous host indicates that pTOXI-1 carries all of the genetic information required for conversion of DBT to 2-HBP.

Successful expression in *E. coli* provided a workable system in which the proteins encoded by the desulfurization cluster could be identified and characterized. Total protein from Dsz+ cells of JM109 (pDRDsz) was isolated and examined on denaturing acrylamide gels. No novel bands could be detected with Coomassie stain. Cellular fractionation of proteins into periplasmic, cytosolic and membrane components were also analyzed by Coomassie stained gels. Again, no novel bands were detected. Without any purification, the newly expressed proteins were apparently levels too low to easily detect and resolve from background.

Maxicell Analysis of *E. coli* harboring pDRDsz

Proteins encoded by genes on plasmid DNA can be specifically radiolabeled in UV-irradiated cells of *E. coli* (Sancar, et al. Journal of Bacteriology. 1979, p. 692–693). This technique is known as Maxicell Analysis. Briefly, a recA strain of *E. coli* e.g. JM109 which harbors a plasmid is grown in M9CA medium (Maniatis et al.) to a density of $2 \times 10^8$ cells/ml. Continuously stirred cells were then subjected to UV exposure from a Mineralight Lamp Model UVG-254 (Ultro-vilet Products, Inc., San Gabriel, Calif.) at a distance of 10 cm for a fluence rate of 0.5 Joules.m$^{-2}$s$^{-1}$. Cells were exposed for either 60, 90 or 120 seconds. The cells were then incubated at 37° C. for 16 hours after which they were then washed with M9 buffer and suspended in minimal medium lacking sulfate. After 1 hour of starvation at 37° C., [$^{35}$S]methionine (>1000 Ci/mmol) (NEN Research Products, Boston, Mass.) was added at a final concentration of 5 μCi/ml and incubation was continued for 1 hour. Cells were collected by centrifugation and proteins isolated through a boiled cell procedure (Maniatis, et al.). Proteins were separated on an acrylamide gel. After the run, the gel was dried and subjected to autoradiography for 3 days.

Maxicells of JM109 harboring vector pDR540 showed only vector marker galactokinase protein. Maxicells of JM109 harboring vector pDRDsz showed the presence of three novel protein bands of sizes which correlated well with the predicted molecular weights of the three proteins responsible for the Dsz+ trait, as predicted by open reading frame analysis (see Table 3).

TABLE 3

| Open Reading Frame | Predicted Size (kDa) | Measured Size (kDa) |
|---|---|---|
| ORF-1 | 49.5 | 49.5 |
| ORF-2 | 38.9 | 33.0 |
| ORF-3 | 45.1 | 45.0 |

Data obtained from Maxicell analysis thus indicated that the three predicted open reading frames of pTOXI-1 encode three structural genes which constitute the desulfurization phenotype.

The relative intensity of the three novel bands is reflective of both the number of methionine residues and the level of translation for each of the proteins. Clearly, ORF-2 with only 1Met gives the faintest band. In addition to the incorporation of only a single Met residue, *E. coli* may process the single terminal methionine, further reducing the amount of labelled protein. Therefore, the low intensity of the ORF-2 band most likely does not strictly suggest a low level of protein translation.

Interestingly, the ORF furthest from the promoter (ORF-3) appears to be present at levels comparable to ORF-1, indicating no polar effects in this operon when expressed in *E. coli*. It is expected that more significant information regarding protein levels will be obtained from a similar Maxicell analysis of a Rhodococcus sp. host containing plasmid pTOXI-I. Additionally, the presence of an ORF-I/ORF-2 heterodimer, postulated above, may be observable under non-denaturing conditions.

As required by 37 C.F.R. Section 1.821(f), Applicant's Attorney hereby states that the content of the "Sequence Listing" in this specification in paper form and the content of the computer-readable form (diskette) of the "Sequence Listing" are the same.

Equivalents

Those skilled in the art will recognize, or be able to ascertain using no more than routine experimentation, many equivalents to the specific embodiments of the invention described herein. These and all other such equivalents are intended to be encompassed by the following claims.

We claim:

1. A purified protein having the amino acid sequence for ORF-1 (SEQ ID NO:2) or an enzymatically active fragment thereof.

2. A purified protein having the amino acid sequence for ORF-2 (SEQ ID NO: 3) or an enzymatically active fragment thereof.

3. A purified protein having the amino acid sequence for ORF-3 (SEQ ID NO: 5) or an enzymatically active fragment thereof.

4. A purified protein having an amino acid sequence selected from the group consisting of ORF-1 (SEQ ID NO: 2), ORF-2 (SEQ ID NO: 3) and ORF-3 (SEQ ID NO: 5) and an enzymatically active fragment thereof.

5. A protein having the amino acid sequence for ORF-1 (SEQ ID NO: 2) wherein the protein is substantially free of other Rhodococcal proteins.

6. A protein having the amino acid sequence for ORF-2 (SEQ ID NO: 3) wherein the protein is substantially free of other Rhodococcal proteins.

7. A protein having the amino acid sequence for ORF-3 (SEQ ID NO: 5) wherein the protein is substantially free of other Rhodococcal proteins.

8. A protein having an amino acid sequence selected from the group consisting of ORF-1 (SEQ ID NO: 2), ORF-2 (SEQ ID NO: 3) and ORF-3 (SEQ ID NO: 5) and an enzymatically active fragment thereof, wherein the protein is substantially free of other Rhodococcal proteins.

* * * * *